United States Patent [19]

Fujio et al.

[11] Patent Number: 5,213,571

[45] Date of Patent: May 25, 1993

[54] LITHOLYSIS APPARATUS PROVIDED WITH SAFE STOP FUNCTION

[75] Inventors: Koji Fujio; Naomi Sekino, both of Hachioji, Japan

[73] Assignee: Olympus Optical Co., Ltd., Tokyo, Japan

[21] Appl. No.: 557,850

[22] Filed: Jul. 26, 1990

[30] Foreign Application Priority Data

| Jul. 27, 1989 | [JP] | Japan | 1-195766 |
| Oct. 11, 1989 | [JP] | Japan | 1-265460 |
| Jan. 10, 1990 | [JP] | Japan | 2-4005 |

[51] Int. Cl.$^5$ ............................................. A61M 1/00
[52] U.S. Cl. ........................................ 604/31; 604/22
[58] Field of Search .................... 604/22, 27, 31, 43

[56] References Cited

U.S. PATENT DOCUMENTS

| 3,860,000 | 1/1975 | Wootten et al. | 604/31 |
| 4,275,726 | 6/1981 | Schael | 604/31 |
| 4,655,744 | 4/1987 | Thistle et al. | |
| 4,759,349 | 7/1988 | Betz et al. | 604/27 |
| 4,922,902 | 5/1990 | Wuchinich et al. | 604/22 |
| 4,994,026 | 2/1991 | Fecondini | 604/31 |
| 5,011,471 | 4/1991 | Miyazaki et al. | 604/22 |
| 5,058,570 | 10/1991 | Idemoto et al. | 604/22 |

Primary Examiner—Gene Mancene
Assistant Examiner—Todd E. Manahan
Attorney, Agent, or Firm—Armstrong & Kubovcik

[57] ABSTRACT

A treatment apparatus for removing a coagulum such as a calculus or the like produced in an organism by dissolving it comprises irrigation with a medical fluid by using an irrigation pump and suction of the medical fluid by using a suction pump. In this apparatus, when a switch for stopping treatment is operated, the apparatus is not immediately stopped, but the apparatus is stopped after the medical fluid introduced into the organism has been completely discharged so that no medical fluid harmful to the organism remains in the organism.

25 Claims, 33 Drawing Sheets

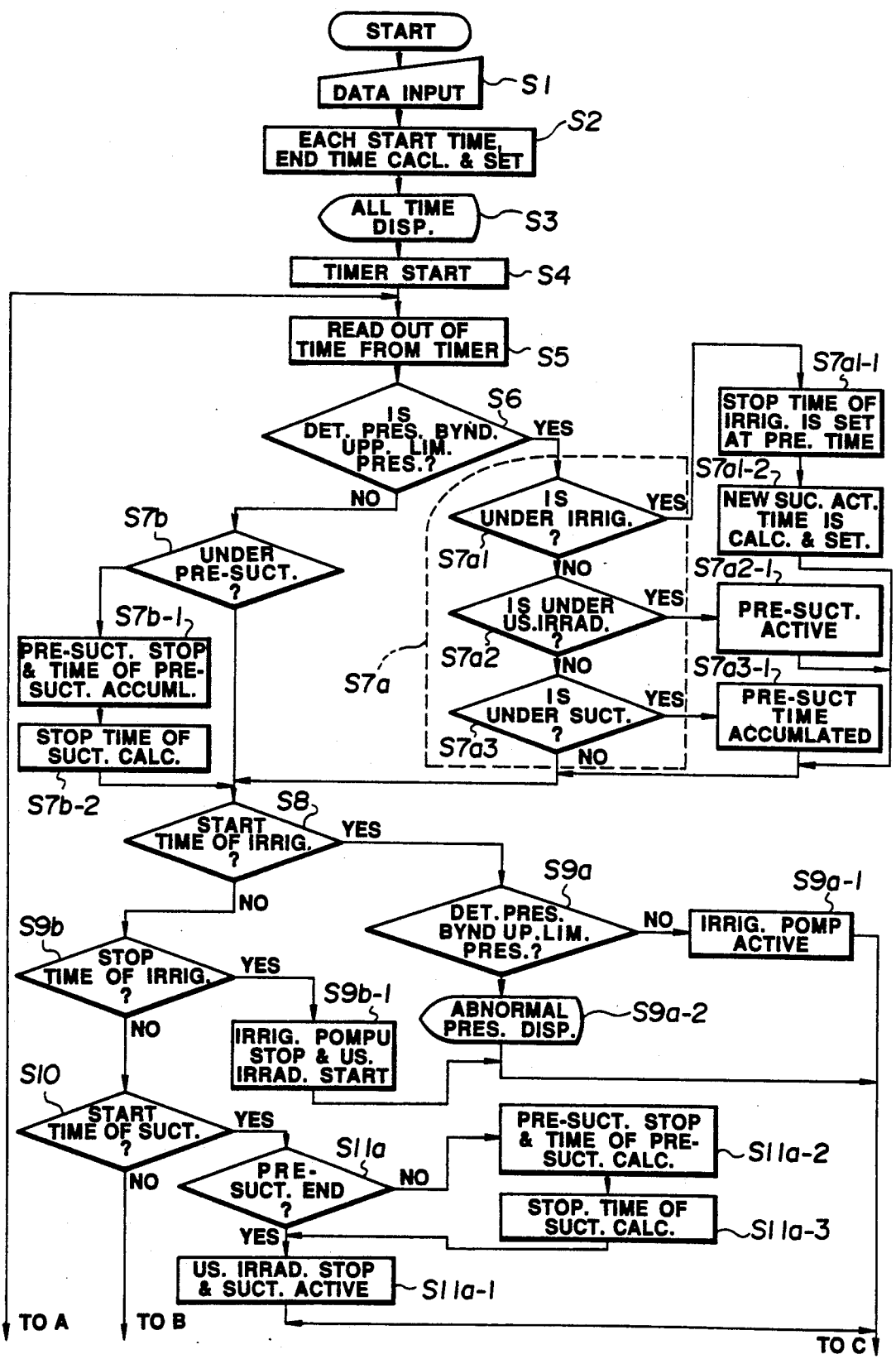

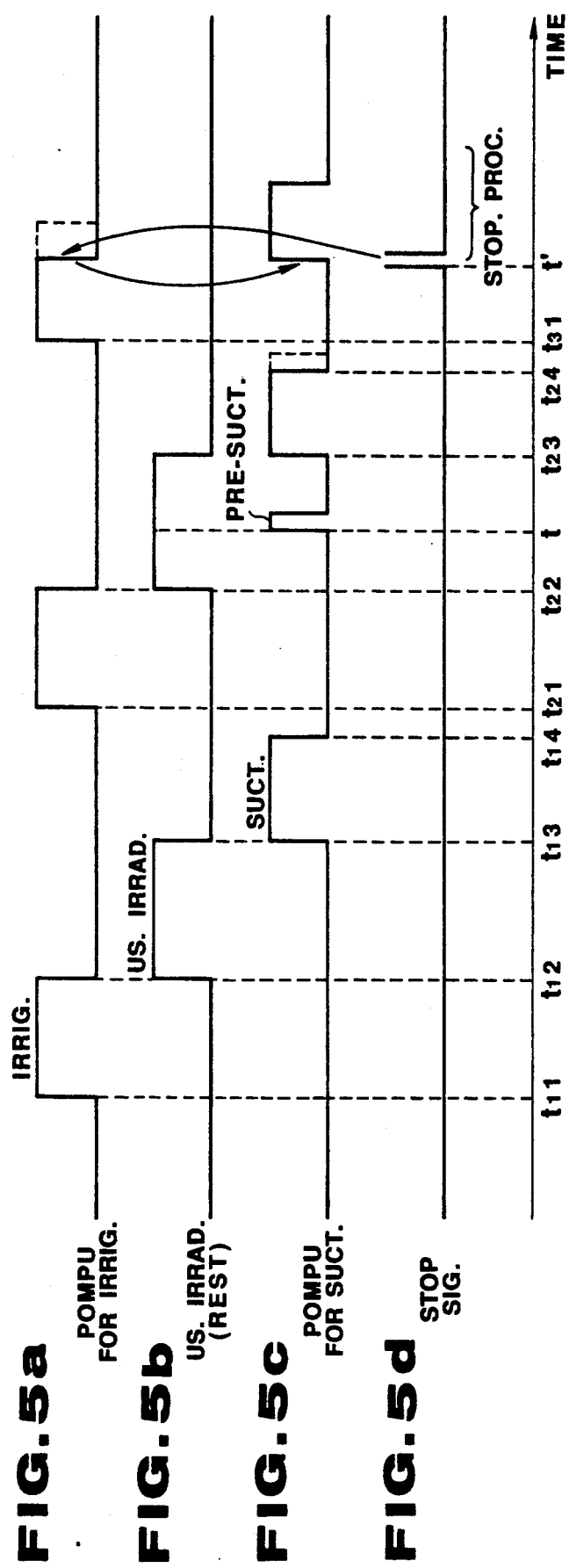

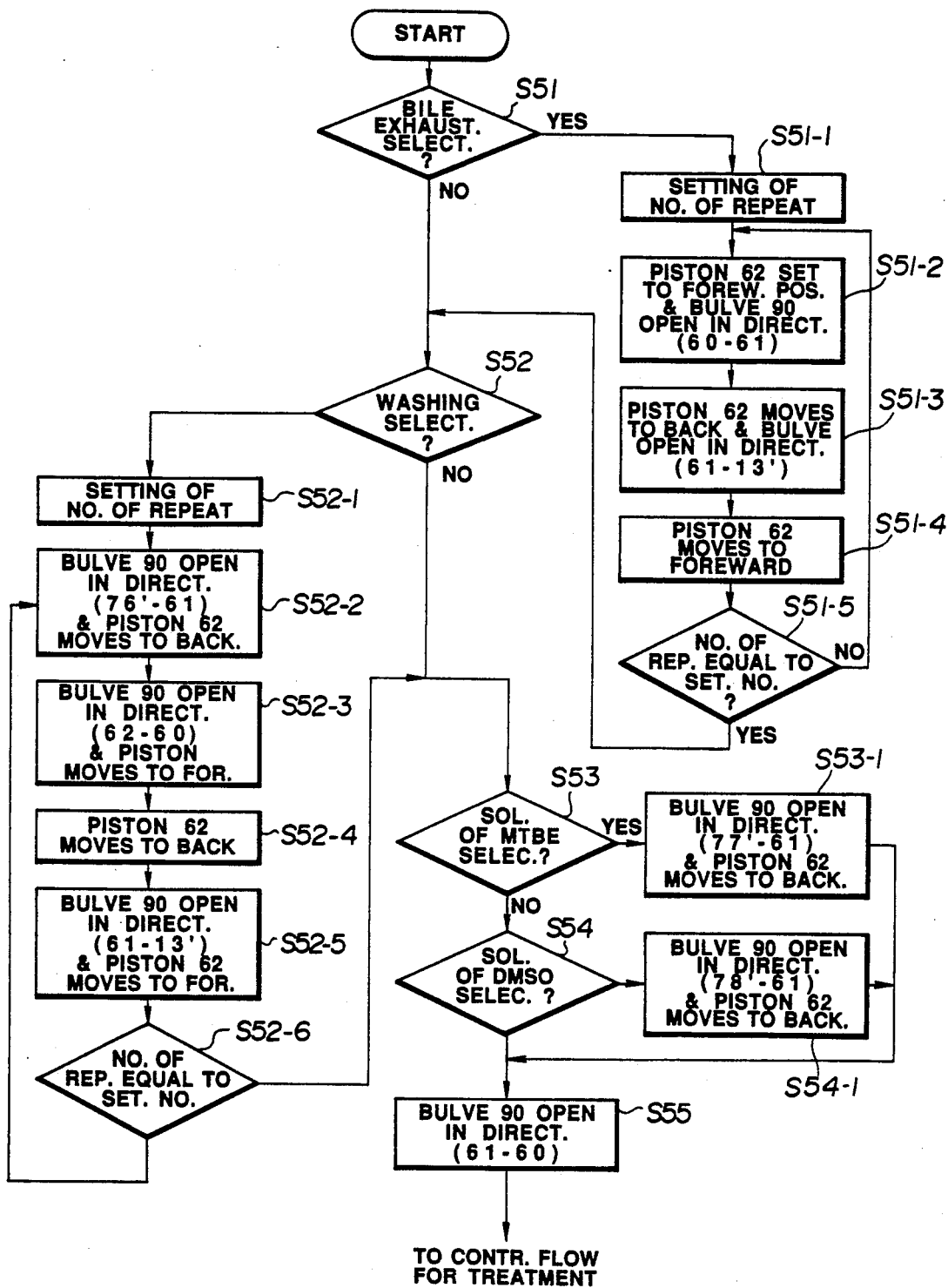

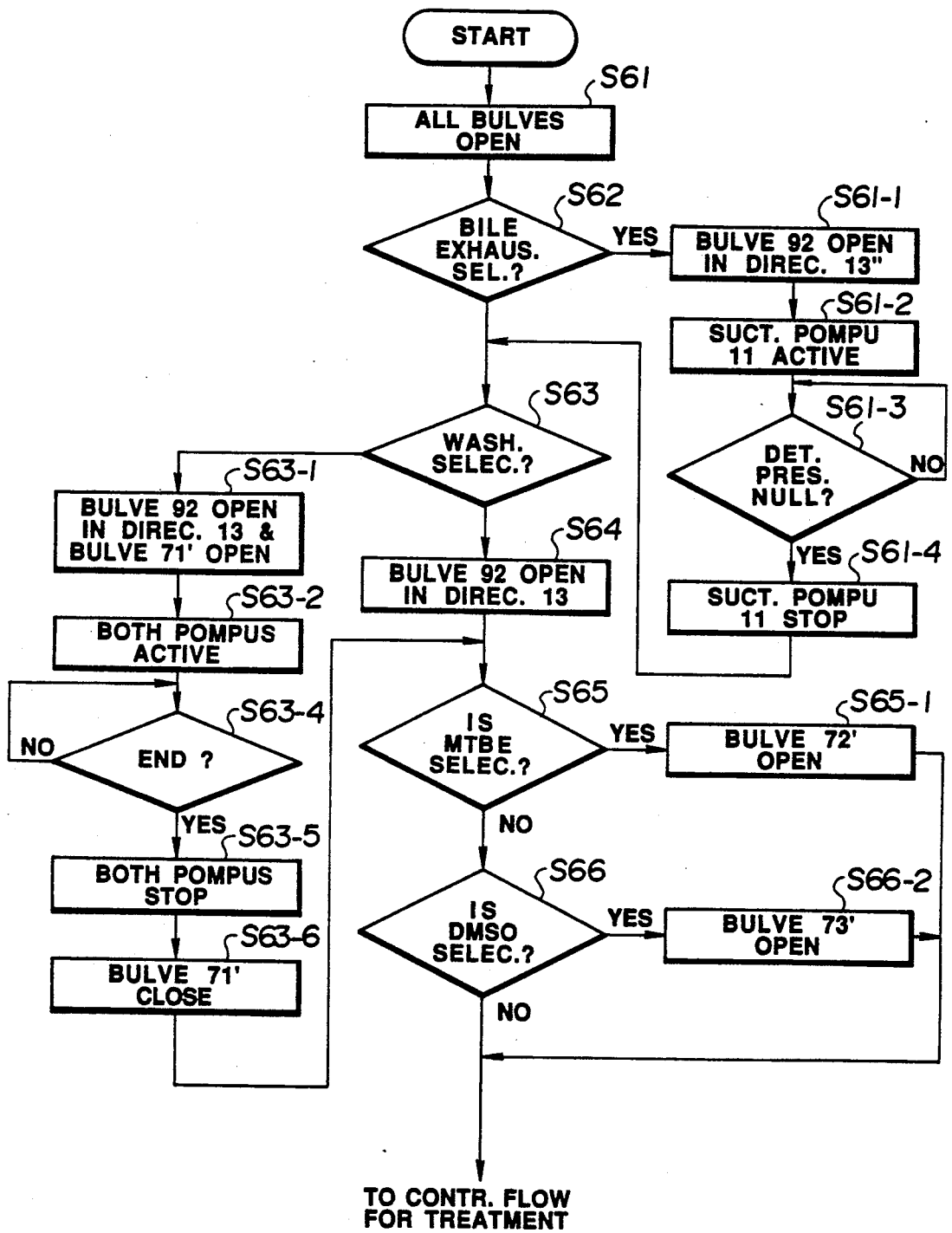

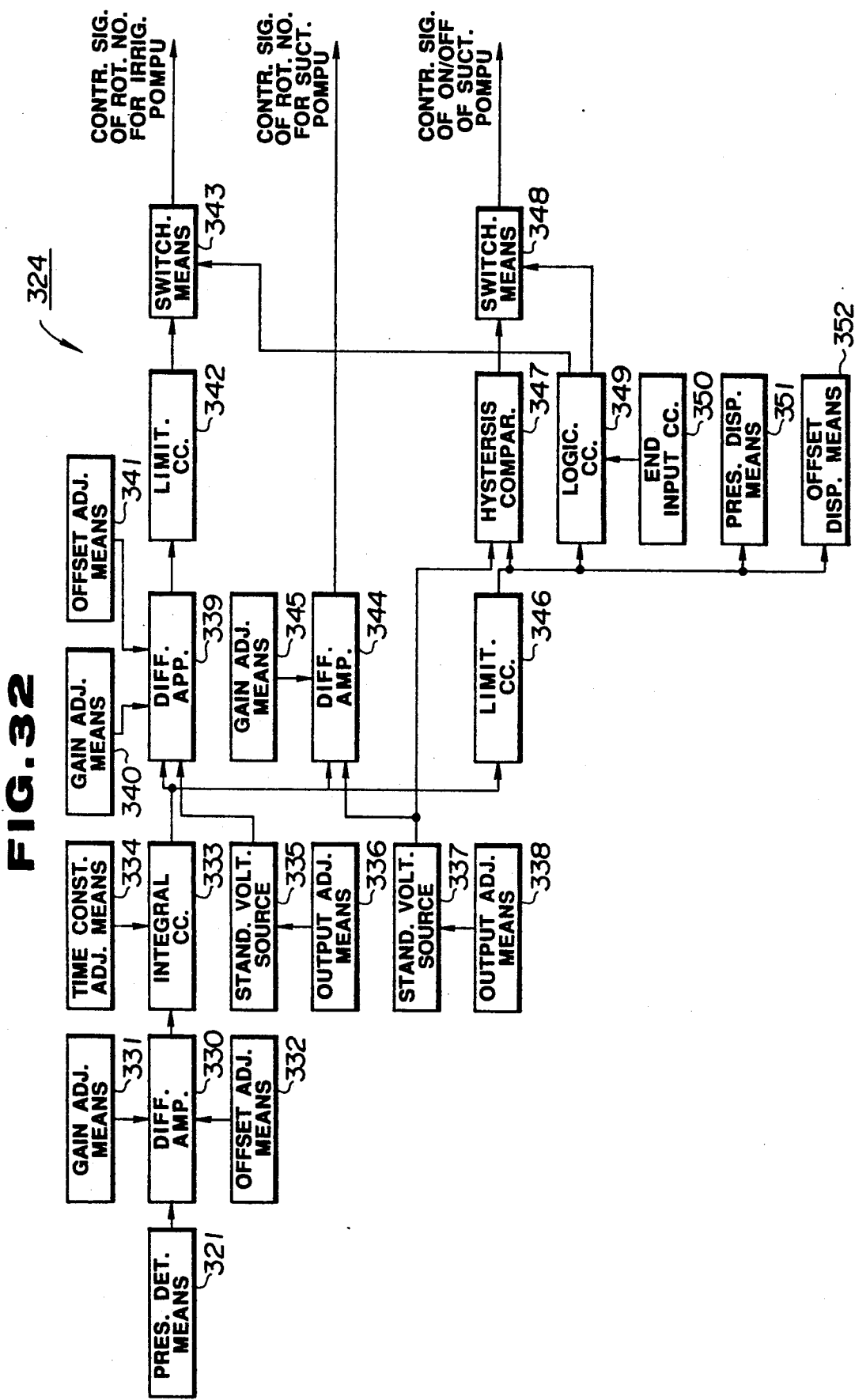

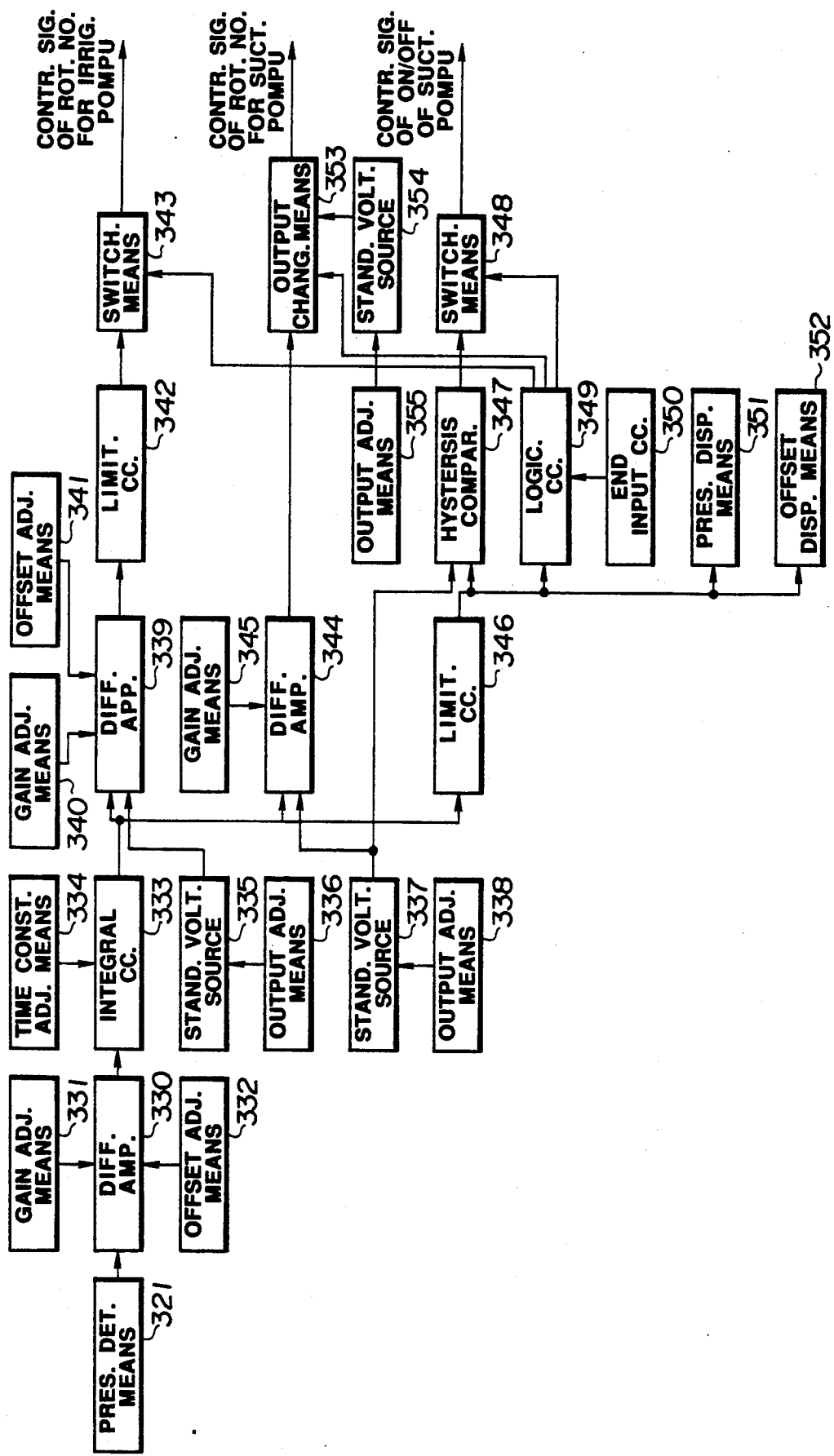

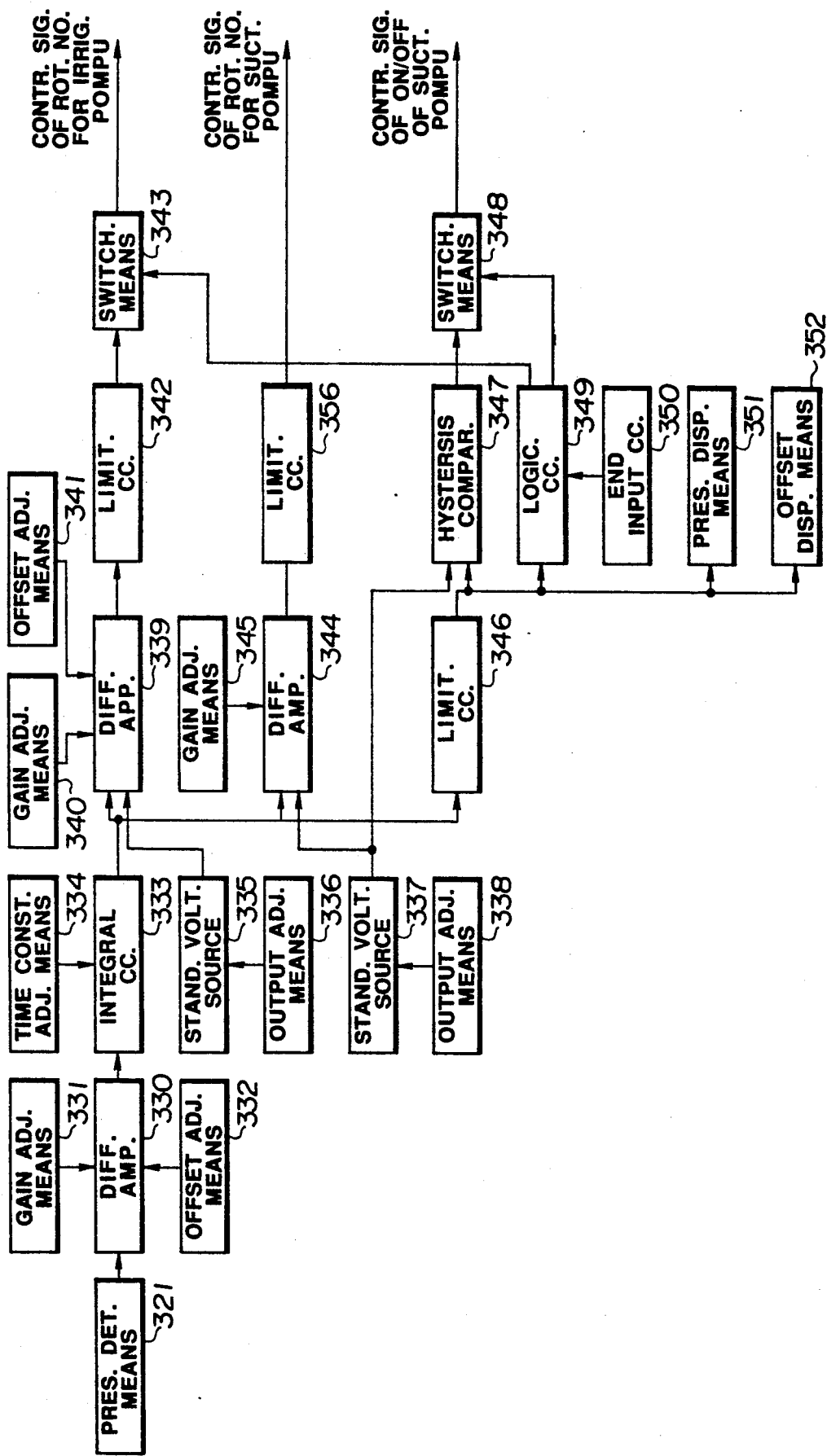

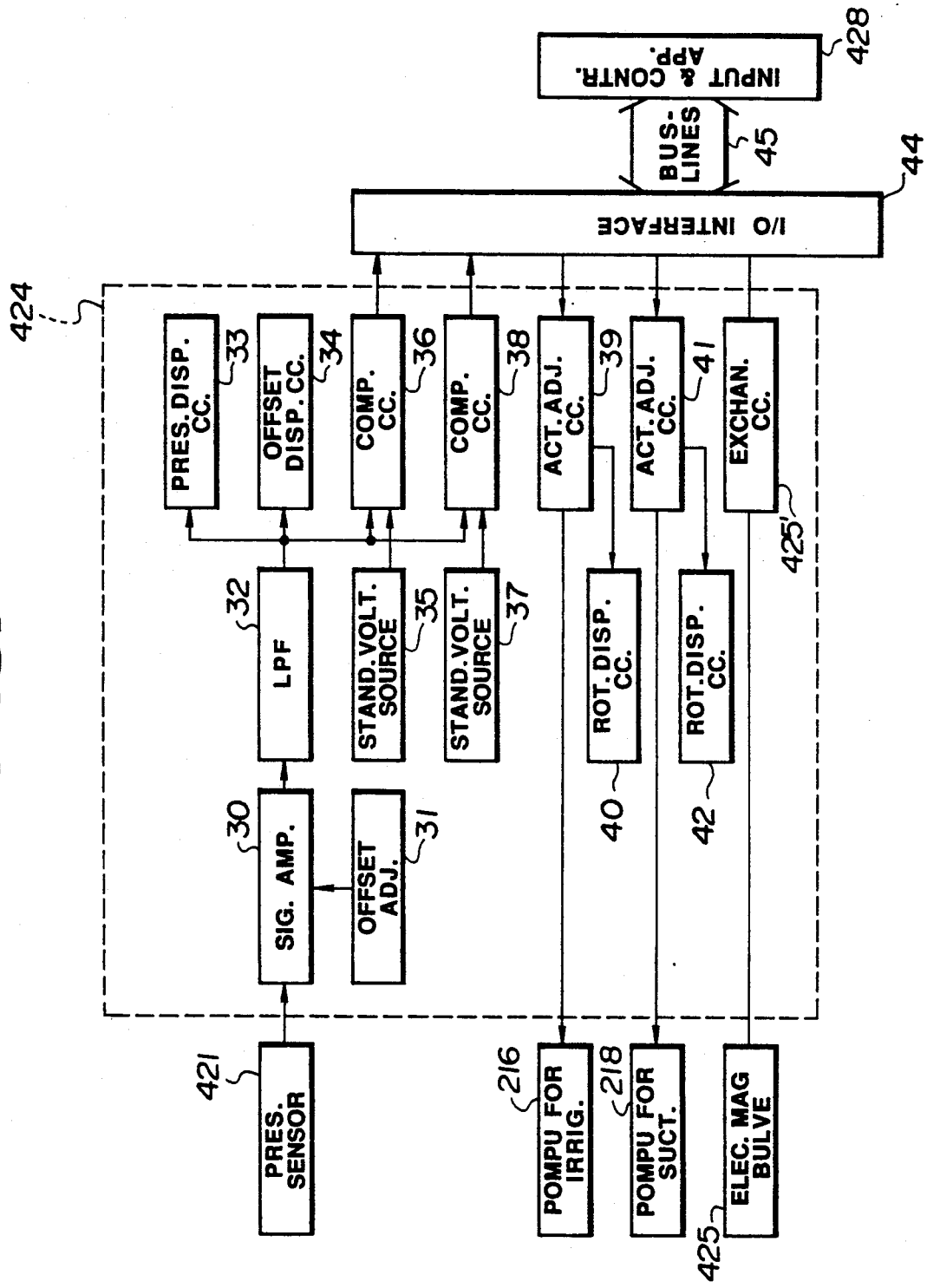

LITHOLYSIS APPARATUS PROVIDED WITH SAFE STOP FUNCTION

BACKGROUND OF THE INVENTION

The present invention relates to a litholysis apparatus for dissolving a calculus produced in an organism by using a medical fluid in which, when a stop operation is carried out, the dissolution treatment is stopped after the medical fluid, which significantly stimulates organisms, has been completely discharged.

A calculus treatment apparatus has been recently proposed for treating a coagulum such as a calculus or the like, which is produced in, for example, the cystic duct in an organism, by dissolving it in a medical fluid such as monoctanoin, octodiol, methyl t-butyl ether (MTBE) or the like, which is introduced into the organism.

For example, first and second examples of prior art are respectively disclosed in Japanese Patent Laid-Open Nos. 62-117545 (U.S. Pat. No. 4,655,744) and 63-40541 (U.S. application Ser. No. 871775).

In the first example, a predetermined quantity of medical fluid is introduced into a treatment part and sucked therefrom by using a pump in an organism so as to promote the dissolution of a calculus under agitation.

The second example is further provided with a means for detecting the pressure in the gallbladder and controlling the flow of a medical fluid so as to keep the pressure in the gallbladder within a set range.

Since a certain time is required for completing litholysis treatment, there is the possibility that the treatment must be stopped owing to a change in condition of a patient in the course of the treatment.

In such a case, in the first example, the medical fluid generally remains in the gallbladder when an apparatus is stopped (or stopped/terminated). Since this medical fluid significantly stimulates organisms, the medical fluid remaining in the gallbladder must be manually recovered.

On the other hand, the second example employs a continuous circulation method in which irrigation and suction are simultaneously made. The apparatus of the second example also has no means for detecting the quantity of the medical fluid storing in the gallbladder and no function to accurately and surely discharge the medical fluid remaining in the gallbladder to the outside of an organism when the apparatus is stopped. Since no treatment is made on the medical fluid when the curative treatment is completed or stopped, therefore, the medical fluid remains in the organism. There is thus a dangerous problem in that the residual medical fluid leaks from the gallbladder.

SUMMARY OF THE INVENTION

It is an object of the present invention to provide a litholysis apparatus which allows curative treatment to be stopped after a patient has been brought into a safe state when an operation of stopping the treatment is performed.

It is another object of the present invention to provide a therapeutic litholysis apparatus which is capable of performing litholysis treatment only by a simple operation.

To this end, the present invention provides a litholysis apparatus comprising an irrigation means for irrigating an organism by a medical fluid for dissolving a calculus therein, a suction means for discharging the medical fluid, in which the calculus dissolves, to the outside of the organism, a control means for controlling the irrigation means and the suction means so as to control the quantity of the medical fluid introduced into the organism and the quantity of the medical fluid discharged therefrom, and a stop treatment means for completely discharging the medical fluid injected by the injection means to the outside of the organism in response to a stop operation performed by a stop operation means for stopping litholysis treatment. The apparatus has the function to safely stop the treatment after stop treatment has been completed by the stop treatment means. The invention further has the function to perform pretreatment such as the discharge of the humor in a treatment portion to the outside of a human body by using the suction means before the litholysis treatment.

BRIEF DESCRIPTION OF THE DRAWINGS

FIGS. 1 to 5 relate to a first embodiment of the present invention, in which:

FIGS. 1a, and 1b are a flow chart which shows the operation of litholysis treatment including stop treatment in the first embodiment;

FIG. 2 is a general drawing of the apparatus of the first embodiment;

FIG. 3 is a schematic drawing of the circulation system in the first embodiment;

FIG. 4 is a block diagram which shows the configuration of a control unit; and

FIG. 5a–d are explanatory views of the typical operation of the first embodiment;

FIGS. 6 to 9 relate to a second embodiment, in which;

FIG. 6 is a schematic drawing of the circulation system in the second embodiment;

FIG. 8 is a flow chart which shows the contents of stop treatment; and

FIG. 9 is a flow chart which shows treatment contents different from those shown in FIG. 8;

FIGS. 10 to 13 are schematic diagrams of the circulation system in a third embodiment of the present invention, in which;

FIG. 10 is a drawing of the configuration of the system in a third

FIG. 11 is a block diagram which shows the configuration of a control unit;

FIG. 12 is a flow chart which shows the contents of stop treatment in the third embodiment; and FIG. 13 is a flow chart which shows contents of stop treatment different from those shown in FIG. 12;

FIGS. 14 to 16 relate to a fourth embodiment of the present invention, in which;

FIG. 14 is a drawing of the configuration of the circulation system in the fourth embodiment;

FIG. 15 is a block diagram which shows the configuration of a control unit; and

FIG. 16 is a flow chart which shows the contents of pretreatment;

FIGS. 17 and 18 relate to a fifth embodiment of the present invention, in which;

FIG. 17 is a drawing of the configuration of the circulation system in the fifth embodiment; and FIG. 18 is a flow chart which shows the contents of pretreatment in the fifth embodiment;

FIGS. 19 and 20 relate to a sixth embodiment of the present invention, in which;

FIG. 19 is a drawing of the configuration of the circulation system in the sixth embodiment; and FIG. 20 is a flow chart which shows the contents of pretreatment in the sixth embodiment;

FIGS. 22 to 24 relate to modification of the seventh embodiment of the present invention, in which;

FIG. 22 is a drawing of the configuration of a circulation system;

FIG. 23 is a block diagram of the configuration of a control unit; and

FIG. 24 is a flow chart which shows the treatment contents in the seventh embodiment;

FIGS. 25 and 26 relate to a eighth embodiment of the present invention, in which;

FIG. 25 is a drawing of the configuration of the eighth embodiment; and

FIG. 26 is a block diagram of the configuration of a circuit unit;

FIGS. 27 and 28 relate to a ninth embodiment of the present invention, in which;

FIG. 27 is a drawing of the configuration of the ninth embodiment; and

FIG. 28 is a block diagram of the configuration of a circuit unit;

FIGS. 29 and 30 relate to a tenth embodiment of the present invention, in which;

FIG. 29 is a drawing of the configuration of the tenth embodiment;, and

FIGS. 32 and 33 relate to an eleventh embodiment of the present invention, in which;

FIG. 32 is a block diagram of the configuration of a control means; and

FIG. 34 is a block diagram of the configuration of the control means in a twelfth embodiment of the present invention;

FIG. 35 is a block diagram of the configuration of the control means in a thirteenth embodiment of the present invention; and FIGS. 36 and 37 relate to a fourteenth embodiment of the present invention, in which;

FIG. 36 is a drawing of the configuration of the circulation system in the fourteenth embodiment; and FIG. 37 is a block diagram of the configuration of the control unit.

DETAILED DESCRIPTION OF PREFERRED EMBODIMENTS

Figure 2:
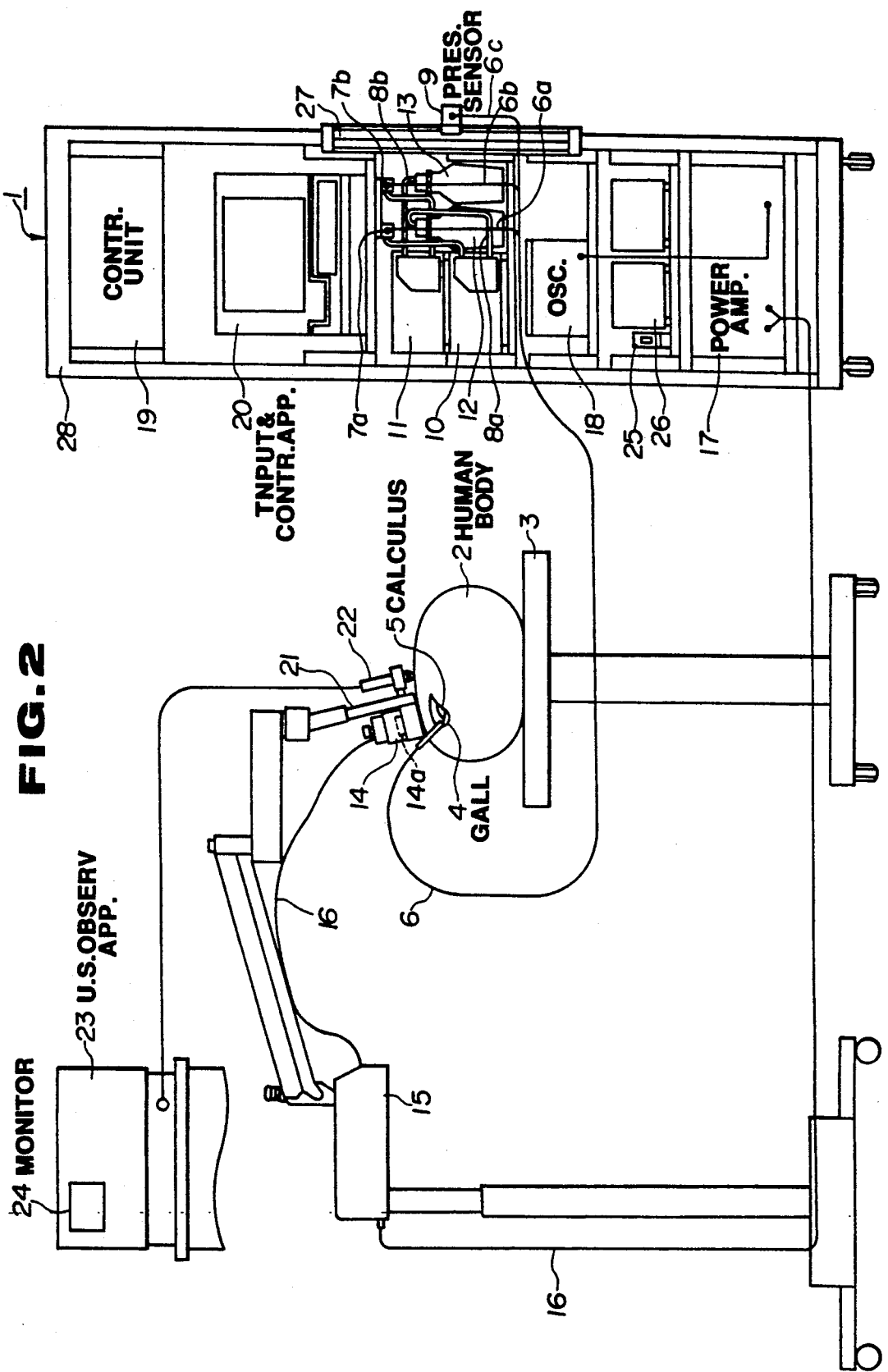
Figure 3:
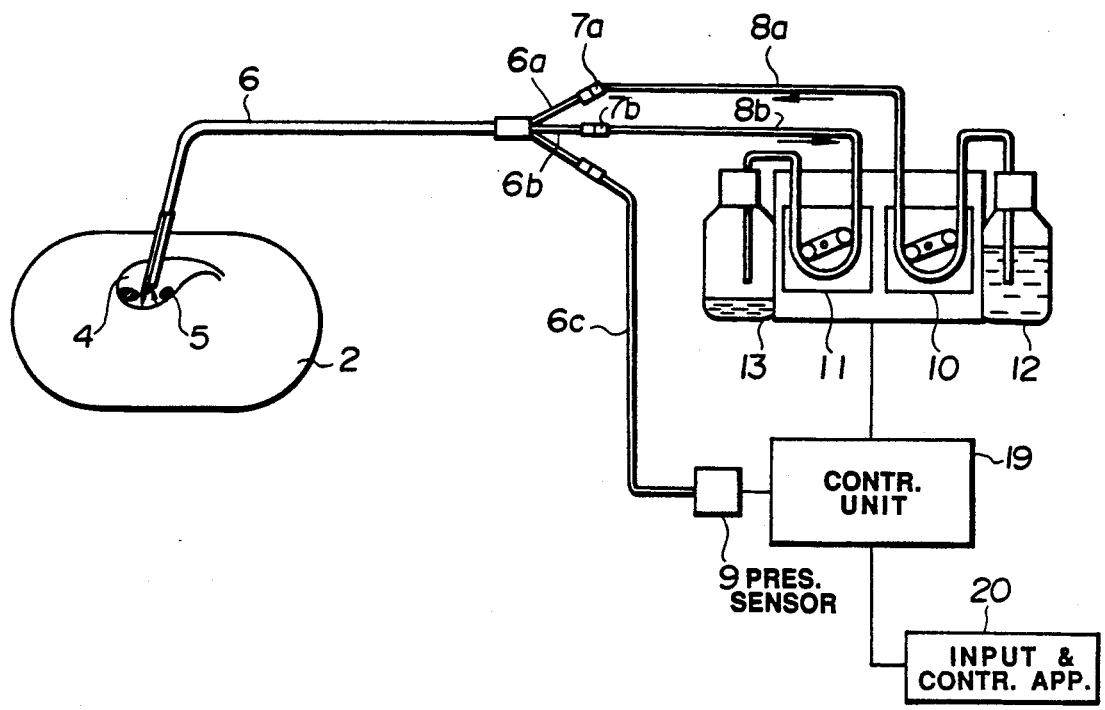

As shown in FIG. 2, a litholysis apparatus 1 has the function to dissolve the calculus produced in, for example, the gallbladder, which is a treatment part, in the human body 2 of a patient who lies down on a medical table 3. As shown in FIGS. 2 and 3, the front end of a catheter 6 is percutaneously inserted into the gallbladder 4, the catheter 6 being made of a porous tube and having three lumens, i.e., an irrigation duct 6a, a suction duct 6b and a pressure duct 6c. The three lumens of the catheter 6 are provided at the rear end of the catherter 6 so as to be branched. The irrigation duct 6a, the suction duct 6b and the pressure duct 6c are connected to an irrigation pump tube 8a through a connector 7a, a suction pump tube 8b through a connector 7b and a pressure sensor 9, respectively.

An irrigation pump 10 is provided at an intermediate position of the irrigation pump tube 8a, and the end of the pump tube 8 is connected to a liquid bottle 12 for storing a medical fluid serving as a lithotriptic such as monoctanoin, d-limonene or methyl t-butyl ether (MTBE).

A suction pump 11 is provided at an intermediate position of the suction pump tube 8b, and the end thereof is connected to an exhaust bottle 13 for storing the fluid recovered from the treatment part.

The irrigation pump 10 and the suction pump 11 are connected to an input/control apparatus 20 through a control unit 19 so that the number of revolutions of the pump can be freely determined by the control unit 19, the driving time of each of the pumps and the operation of switching the pumps can be set by the input/control apparatus 20. Each of the pumps 10, 11 is operated in accordance with the set contents.

As shown in FIG. 2, an ultrasonic applicator 14 for applying an ultrasonic wave to the gallbladder 4 contains a single or a plurality of ultrasonic piezoelectric transducers (not shown). The ultrasonic applicator 14 is supported and fixed by a support member 21 which is disposed at the end of a support arm 15 and connected to a power amplifier 17 by means of a cable 16.

The signal output from an oscillator 18 is input to the power amplifier 17.

The signal output from the control unit 19, in which the frequency, amplitude, pulse number, pulse separation and driving time are adjusted and set, is input to the oscillator 18. The signal output from the oscillator 18 is amplified by the power amplifier 17, and the amplified signal is applied to the ultrasonic piezoelectric transducer 14a in the ultrasonic applicator 14.

The ultrasonic wave excited by the ultrasonic piezoelectric transducer 14a is applied to a portion including the calculus 5, which is present in the gallbladder 4 in the human body 2.

An ultrasonic observation probe 22 is detachably supported by the support member 21 opposite to the ultrasonic applicator 14, with the central axis of the support member 21 therebetween. The ultrasonic probe 22 and the ultrasonic applicator 14 can be rotated for 180° around the center of the support member 21 so that the central axis of the observation range of the ultrasonic probe 22 agrees with the central axis of the ultrasonic irradiation region of the ultrasonic applicator 14.

The ultrasonic probe 22 is connected to an ultrasonic observation apparatus 23 so that an ultrasonic image including the gallbladder 4 in the human body 2 is displayed on a monitor 24.

The control unit 19, the input/control apparatus 20, the irrigation pump 10, the suction pump 11, the oscillator 18 and the power amplifier 17 are connected to a power source through an insulating transformer 26 and a power switch 25.

The pressure sensor 9 is movable in the longitudinal direction, i.e., the vertical direction, on a rail 27 so that it can be fixed at any desired position on the rail 27.

The control unit 19, the input/control apparatus 20, the connectors 7a, 7b and irrigation pump 10, the suction pump 11, the liquid bottle 12, the exhaust bottle 13, the oscillator 18, the power switch 25, the insulating transformer 26, the rail 27 and the power amplifier 17 are installed or fixed on a body rack 28.

Figure 4:
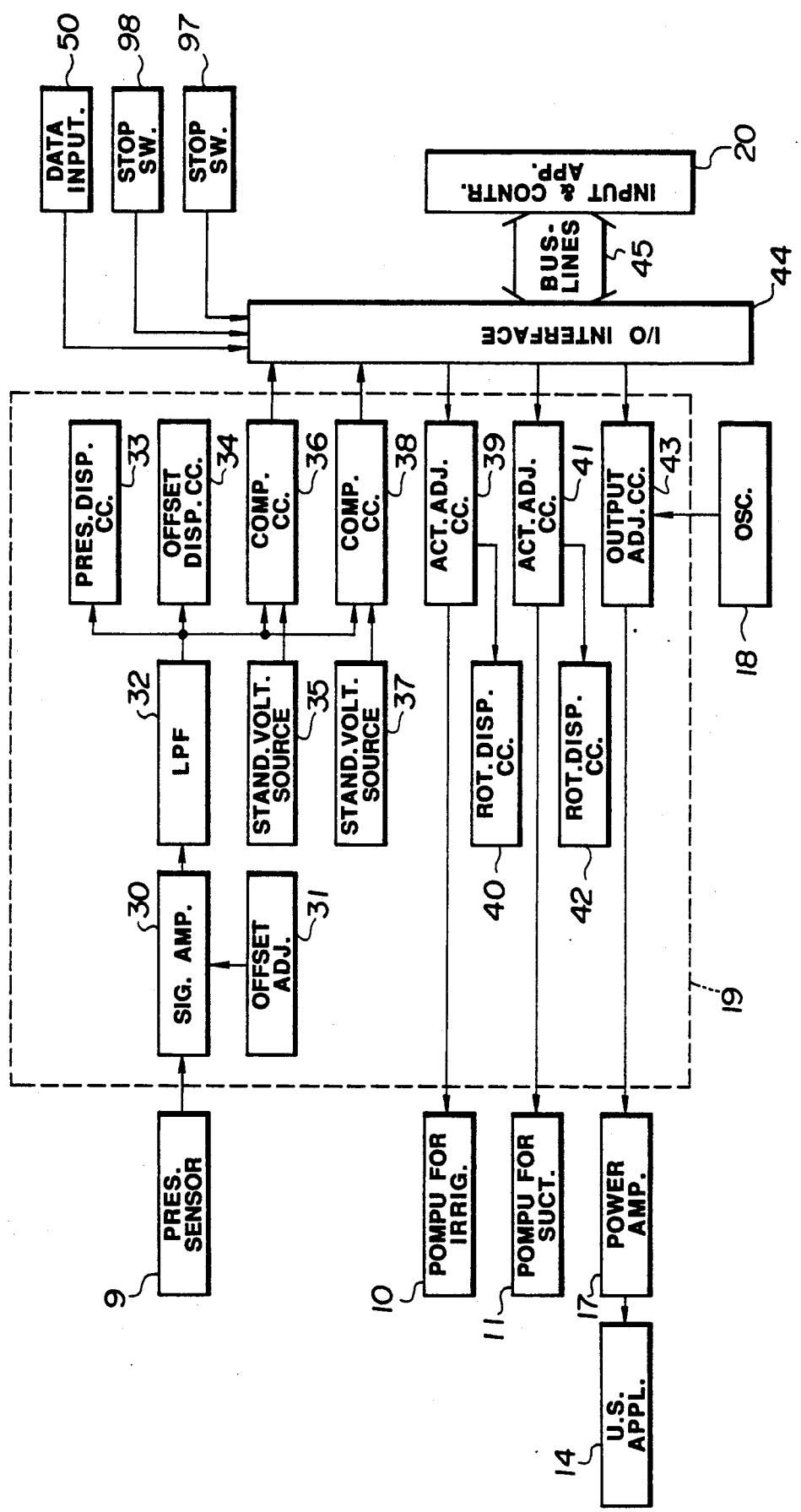

The configuration related to the control unit 19 is described below with reference to FIG. 4.

The pressure sensor 9 is connected to a signal amplifier 30, a signal amplified by the signal amplifier 30 being input to comparison circuits 36 and 38 through a low pass filter 32. To the comparison circuits 36 and 38 are respectively connected a standard voltage source 35 corresponding to the upper limit pressure and a standard voltage source 37 corresponding to the lower limit pressure during suction. A signal of comparison between a pressure signal and a standard signal is input to the input/control apparatus 20 through an I/O interface 44 and a bus 45.

An offset adjusting means 31 is connected to the signal amplifier 30 so that the offset of the pressure signal output from the signal amplifier 30 can be adjusted. The pressure signal passed through the low pass filter 32 is then input to a pressure display circuit 33 for displaying the pressure of the treatment part and to an offset pressure display circuit 34.

The irrigation pump 10 and the suction pump 11 are respectively connected to action adjusting circuits 39, 41 to which action control signals are input from the input/control apparatus 20 through the bus 45 and the I/O interface 44 and to which revolution display circuits 40, 42 are respectively connected.

The oscillation output from the oscillator 18 is applied to the input terminal of the output adjusting circuit 43 so that the output from the oscillator 18 can be adjusted by using the control signal applied to the control terminal through the I/O interface 44. The output from the oscillator 18 is adjusted, for example, with respect to its frequency, amplitude, pulse number, pulse separation and driving time, by the output adjusting circuit 43 using the control signal input from the input/control apparatus 20 through the I/O interface 44 and the bus line 45. The output is then amplified by the power amplifier 17 so as to drive the ultrasonic piezoelectric transducer 14a in the ultrasonic applicator 14.

A stop switch 97 is provided as a means for stopping the treatment. If the switch 97 is turned on, a stop signal is sent to the input/control apparatus 20 through the I/O interface 44 so that the input/control apparatus 20 controls the action of stopping the treatment on the basis of the stop signal.

A stop switch 98 for forcing the treatment to stop is also provided.

A data input means 99 such as a key board or the like for inputting treatment data to the input/control apparatus 20 is further provided.

In this first embodiment, the irrigation pump 10 and the suction pump 11 perform the actions (typical action) shown in FIG. 5 on the basis of the control by the input/control apparatus 20.

When the time read from a timer reaches an irrigation start time $t_1 1$, the irrigation of the medical fluid is started by the rotation of the irrigation pump 10, as shown in FIG. 5a. The irrigation pump 10 is stopped at an irrigation end time $t_1 2$. This time $t_1 2$ is the start time of ultrasonic irradiation at which ultrasonic irradiation is started, as shown in FIG. 5b. After the irradiation, the suction pump 11 is started so as to start suction, as shown in FIG. 5c. After the suction has been continued to a time $t_1 4$, a rest is started. After the rest time has passed, a first treatment comprising irrigation, ultrasonic irradiation and suction is finished, and second treatment is then started.

In each action, the pressure in the gallbladder is monitored by using the signal output from the pressure sensor 9 so that it is allowable pressure. For example, if the detected pressure exceeds the upper limit at a time during the ultrasonic irradiation shown in FIG. 5, therefore, the suction pump 11 is rotated so as to perform suction (referred to as "pre-suction" hereinafter), as shown in FIG. 5c. When the pressure becomes the upper limit or less, the suction is stopped. Although the suction pump 11 is then rotated so as to perform suction after the ultrasonic irradiation has been completed, the quantity of suction is reduced by the quantity of the pre-suction.

Although above-described operation is a normal operation, for example, if the stop switch 97 is operated at a time t' during the irrigation shown in FIG. 5a, the stop signal is output, as shown in FIG. 5d, and the input/control apparatus 20 controls the stop treatment when detecting the signal.

Namely, the irrigation pump 10 is immediately stopped so that the irrigation is stopped (refer to FIG. 5a), and the quantity of the medical fluid introduced up to the stop time is calculated. The suction pump 11 is immediately operated in correspondence with the irrigation quantity calculated (refer to FIG. 5c) so as to discharge the medical fluid, which is introduced in the human body, to the outside thereof. After the medical fluid has been completely discharged, the suction is stopped, and the apparatus is stopped.

If the stop switch 97 is operated during ultrasonic irradiation, the irradiation is stopped, and the suction pump 11 is immediately operated. If the stop switch 97 is operated during the operation of the suction pump 11, after the medical fluid introduced has been completely discharged to the outside of the human body by continuous suction, the suction pump 11 is stopped.

If the stop switch 98 is operated, the apparatus is immediately stopped.

The input/control apparatus 20 controls the irrigation pump 10 and the suction pump 11 in accordance with the flow chart shown in FIG. 1 so that the above-described actions are carried out.

The operation of the apparatus 1 is described in detail below with reference to FIG. 1.

When the operation of the apparatus 1 is started, treatment data required for curative treatment is input in Step S1. Namely, the operator inputs to the input/control apparatus 20 the irrigation time taken for introducing the medical fluid and the suction time for sucking the medical fluid or the irrigation quantity and suction quantity, the ultrasonic irradiation time or standing time, and, if required, the stop time and the number of repetitions.

When the data is input in Step S1, the treatment time and the start time and end time of each action are calculated and set in Step S2. Namely, the total time required for treatment is calculated on the basis of the data input in Step S1.

The start time and end time of each of the means (for example, the irrigation pump 10, the suction pump 11 and the ultrasonic applicator 14), i.e., the nth irrigation start time $t_n 1$, the nth irrigation end time and an ultrasonic irradiation (standing) start time $t_n 2$, the nth ultrasonic irradiation (standing) end time and suction start time $t_n 3$, the nth suction stop time and rest start time $t_n 4$, and the nth rest end time, i.e., (n+1)th irrigation start time $t_{n+1}1, \ldots,$ are calculated over the treatment. These times are set and stored in the input/control apparatus 20. The active state and inactive state of each of the operational means are switched on the basis of the calculated times.

When the times are calculated, the total treatment time of treatment is displayed in Step S3. Namely, the time required for treatment, which is calculated in Step S2, is displayed on the display part of the input/control apparatus 20.

After the treatment time has been displayed, the timer is started in Step S4. In order to control the time required for treatment, the timer in the input/control apparatus 20 is operated in such a manner that the time (the elapsed time from the start of treatment) can be known at any time as occasion demands. When the timer is started, the input/control apparatus 20 reads the time from the timer in Step S5 and then decides whether or not the pressure in the gallbladder exceeds the upper limit pressure in Step S6.

The pressure in the gallbladder is measured by the pressure sensor 9, and the pressure signal is input to the comparison circuit 36 in the control unit 19 in which it is compared with the standard voltage source 35 corresponding to the upper limit pressure value. Namely, a decision is made as to whether or not the detected signal is beyond the upper limit pressure value, i.e., whether the output state of the comparison circuit 36 is "H" or "L".

In a case of YES in Step S6, the processing in Step S7 is performed for deciding the action state at a time the pressure is over the upper limit pressure value and then moves to Step S8. On the other hand, in a case of NO, a decision is made in Step S7b as to whether or not the fluid is under pre-suction. Step S7a comprises Steps S7a1, S7a2 and S7a3 of making decisions as to whether or not the fluid is under irrigation, ultrasonic irradiation and pre-suction, respectively.

When the fluid is under irrigation, the irrigation stop time is set at the present time in Step S7a1-1 in order to stop the irrigation. The irrigation is thus stopped after the time the irrigation stop time is decided in the subsequent step. After Step S7a1-1, a suction stop time is newly calculated and set.

In Step S7a1-2, a new suction stop time is set so that the true irrigation time equals to the suction time on the basis of the irrigation time the medical fluid is actually introduced until irrigation is stopped by the pressure sensor 9 which detects the pressure. The processing moves to Step S8.

In the ultrasonic irradiation in Step S7a2, an ultrasonic wave is applied to the interior of the human body from the ultrasonic applicator. When no ultrasonic wave is applied, a decision is made as to whether or not the human body is left to stand. In a case of YES, pre-suction is started, i.e., the suction pump 11 is started. The processing then moves to Step S8. The pre-suction is carried out by rotating the suction pump 11 until the pressure in the gallbladder is decreased to the upper limit pressure or less for removing excessive pressure when the pressure in the gallbladder is higher than the predetermined upper limit value during the ultrasonic irradiation (or standing). After the pre-suction in Step S7a2-1, the processing moves to Step S8.

In Step S7a3, a decision is made as to whether or not the fluid is under pre-suction. In a case of YES, the pre-suction time is integrated in Step S7a3-1, and the processing then moves to Step S8. In Step S7a3-1, the operation time the suction pump for pre-suction is integrated each time the time is read from the timer in Step S5.

When the result of a decision whether or not the fluid is under pre-suction is YES in Step S7b, in Step S7b-1, the suction is stopped, and the pre-suction time is calculated. Namely, the suction pump is stopped, and the operation time of the suction pump 11 is determined. A new nth suction stop time is then calculated in Step S7b-2, and the processing moves to Step S8. In Step S7b-2, the stop time of the suction pump 11 during the suction action is determined so that the irrigation time equals to the sum of the pre-suction time and the suction time.

In Step S8, a decision is made as to whether or not the time is the start time of nth irrigation. In a case of YES, a decision is made as to whether or not the pressure in the gallbladder is beyond the upper limit in Step 9a. In a case of NO, a decision is made as to whether or not the time is the nth irrigation stop time in Step S9b.

The irrigation start in Step S8 means that the rotation of the irrigation pump 10 is started.

The result of the decision made in Step 9a is NO, the irritation pump is started in Step S9a-1, and the processing then moves to Step S12. In a case of YES, abnormal pressure is displayed in Step S9a-2, and the processing then moves to Step S12.

In a block including Steps S9a and S9a-2, the abnormal pressure is displayed because, if the pressure in the gallbladder is beyond the upper limit value during the irrigation start, the irrigation pump 10 is not rotated in correspondence with the processing and processing speed of the block.

When the result of the decision made as to whether or not the time is the nth irrigation stop time is NO in Step S9b, a decision is made as to whether or not the time is the nth suction start time in Step S10. In a reverse case of YES, in Step S9b1-1, the suction pump is stopped, and the ultrasonic irradiation (or standing) is started, and the processing then moves to Step S12.

The result of the decision made in Step S10 is NO, the processing moves to Step S11b, and when the result of the decision is YES, a decision is made as to whether or not the pre-suction is completed in Step S11a. When the result of the decision made in Step S11a is YES, in Step S11a-1, ultrasonic irradiation (or standing) is stopped, suction is started, and the processing then moves to Step S12. When the result of the decision made in Step S11a is NO, in Step S11a-2, the pre-suction is stopped, and the pre-suction time is calculated. In Step S11a-3, a new (nth) suction stop time is calculated, and the processing then moves to Step S11a-1.

In the block including Steps S11a, S11a-2 and S11a-3, when suction is started before the pre-suction is completed, the operation time of the suction pump 11 is considered as the pre-suction time, and the pre-suction is stopped in the same way as that described above.

When the result of the decision made as to whether or not the time is the nth suction stop time is NO in Step S11b, in Step S12, a decision is made as to whether or not the treatment is stopped. In a reverse case of NO, in Step S11b-1, the suction pump is stopped, and the processing moves to Step S12.

The times of Steps S8, S9b, S10, S11b correspond to the times $t_n1, t_n2, \ldots,$ respectively.

In Step S12, a decision as to whether or not the treatment is stopped is made by deciding whether or not the input/control apparatus 20 selects the treatment stop.

When the treatment is not stopped, the processing moves to Step S13. When it is decided that the treatment stop is selected, decisions are made as to whether or not the fluid is under irrigation, ultrasonic irradiation (or standing), suction and pre-suction in Steps S12-1, S12-2, S1203 and S12-4, respectively.

In Steps S12-1 to S12-4, the action state at the stop of the treatment is decided.

When it is decided in Step S12-1 that the the treatment is under irrigation, the irrigation pump is stopped in Step S12-5. When the result of the decision made in Step S12-2 is YES, the ultrasonic irradiation is stopped in Step S12-6. When the human body is allowed to stand, the standing is stopped in Step S12-6. When the result of the decision made in Step S12-3 is YES, the suction time is calculated in Step S12-7. When the result of the decision made in Step S12-4 is YES, the pre-suction time is calculated in Step S12-8. When the processing in Steps S12-5 to S12-8 is completed, the suction stop time is calculated in Step S12-9. The quantity of the medical fluid remaining in the gallbladder is determined from the difference between the operation time of the irrigation pump 10 and the operation time of the suction pump 11 (including the operation time of the suction pump 11 for pre-suction). The suction stop time is determined from the suction time required for sucking the medical fluid remaining in the gallbladder.

After the processing in Step S12-9, the suction pump is started in Step S12-10, and a decision is then made as to whether or not the present time is the suction stop time in Step S12-11. When the time is not the suction stop time, a decision is made as to whether or not the suction action is stopped in Step S12-12.

In Step S12-12, a decision is made as to whether or not the stop of suction action is further selected in a stop treatment loop. When the result of this decision is NO, the time is read from the timer in Step S12-13, and the processing returns to Step S12-11. Since the present time read out from the timer in Step S4 cannot be input in Step S12-13, in Step S12-13, the present time is read and used for deciding the action with time.

When the results of the decisions made in Steps S12-11 and S12-12 are YES, the operation of the suction pump is stopped in Step S12-14, and the processing then moves to Step S15.

When the result of the decision made in Step S13 as to whether or not the nth rest end time is NO, the processing returns to Step S5. This decision is made for deciding whether or not one sequence is completed.

When no rest time is provided, a decision is again made as to whether or not the time is the suction stop time. When the result of the decision made in Step S13 is YES, a decision is made as to whether or not the number of repetitions equals to the set number in Step S14. When the result of this decision is NO, the number of repeated treatments is counted up (n=N+1) in Step S14-1, and the processing returns to Step S5.

In Step S14, a decision is made as to whether or not the number of repeated sequences reaches the set number m. In Step S14-1, the variable, which indicates the number of actually repeated sequences, is increased by one for the purpose of performing the next sequence.

When the result of the decision made in Step S14 is YES, the treatment data is stored in Step S15, and the processing is completed.

In Step S15, the results of treatment actions such as the actual irrigation time and irrigation quantity, the actual suction time and suction quantity, the pre-suction time and quantity, the standing or ultrasonic irradiation time, the number of actually repeated sequences and so forth are stored in the input/control apparatus 20.

Figure 1B:
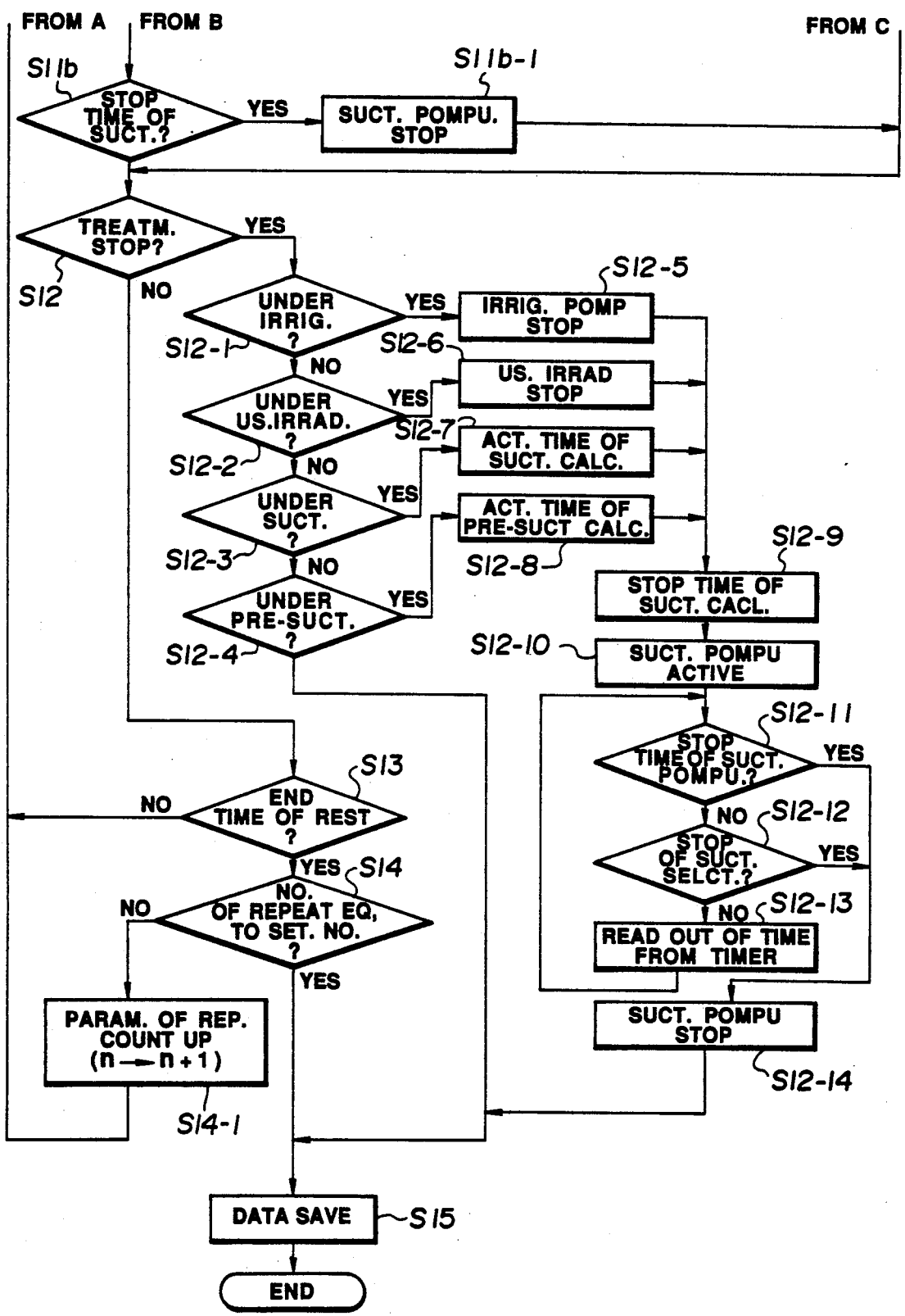

In the first embodiment, when the treatment is stopped, the input/control apparatus 20 detects the stop of the treatment in accordance with the flow chart shown in FIGS. 1a and 1b and performs the stop treatment of stopping the apparatus 1 after the medical fluid has been completely discharged from the gallbladder.

This stop treatment permits the treatment action of the apparatus to be stopped after the whole of the lithotriptic introduced has been completely discharged by suction to the outside of the human body, without the lithotriptic remaining in the human body even if the treatment is stopped at any time during the action of the apparatus. This function permits safe and sure litholysis treatment. When the treatment must be urgently stopped, since the suction discharge is stopped in the course of treatment so that the operation of the apparatus can be completely stopped, it is secured that the safe stop treatment can cope with the emergency stop of treatment.

In addition, in order to improve the rapidity of suction of the medical fluid by increasing the suction speed, the suction pump stop time may be calculated and set in each of Steps S7a1-2, S71-2, S11a-3 and S12-9 shown in FIGS. 1A and 1B, and the irrigation and suction action times may be input and set in Step S1, on the assumption of a difference between the irrigation speed and the suction speed, so that the speed of suction discharge comprising the suction and stop actions or the operational speed of the suction pump 11 during both operations is higher than the irrigation speed in this embodiment. This causes an increase in speed of the action to discharge the medical fluid to the outside of the human body, improvements in the effect of removing excess pressure by the pre-suction and in the rapidity of the stop treatment and secures safe stop treatment.

Figure 6:
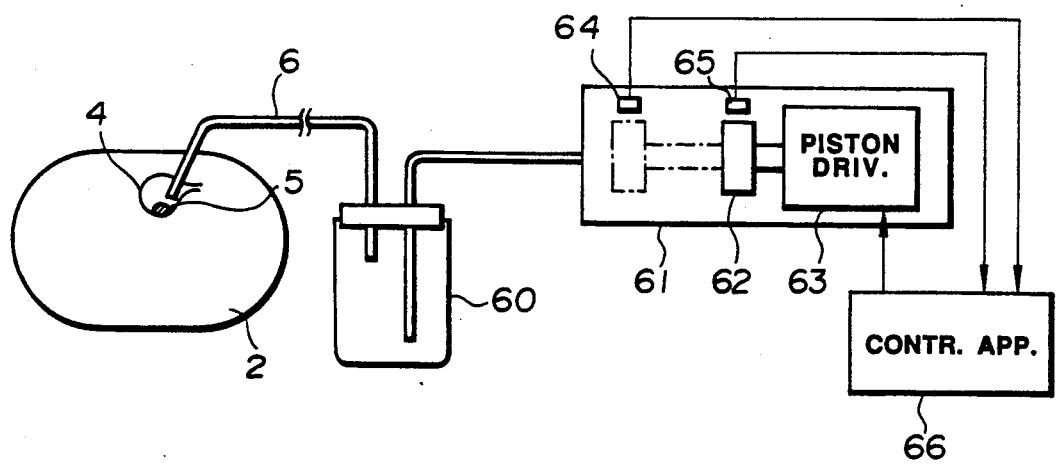

FIG. 6 is a schematic drawing of the circulation system of an apparatus in a second embodiment of the present invention.

This embodiment uses a single pump 61 for introducing and sucking a lithotriptic. In the pump 61, a piston 62 is moved by a piston driving means 63 in the longitudinal direction in a cylinder so that the lithotriptic is introduced owing to the forward movement of the piston 62 and is sucked owing to the backward movement thereof. A trap 60 is provided at an intermediate position of the tube of the catheter 6, through which the lithotriptic flows, for the purpose of separating the humor and calculus fragments from the lithotriptic by utilizing the difference in specific gravity. A forward detector 64 and a backward detector 65, either of which comprises, for example, a proximity sensor, are provided in the pump 61 in order to detect the position of the piston 62. The position of the piston 62 may be detected by, for example, providing an encoder on the piston driving means 63 or a shaft which transmits driving force to the piston 62 from the piston driving means 63. The forward detector 64 and the backward detector 65 are connected to a control apparatus 66 so that the positional detection signal from each of the detectors is input to the control apparatus 66. The control apparatus 66 outputs a control signal to the piston driving means 63 so as to control the forward and backward movements of the piston 62.

Figure 7A:
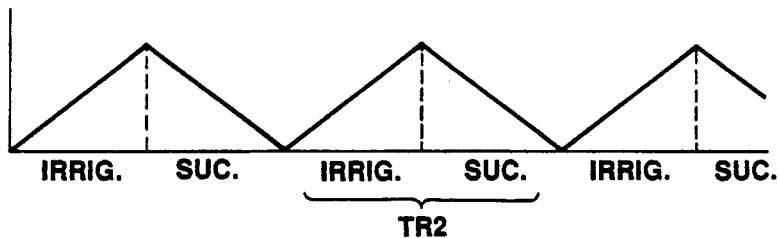
FIG. 7a–e are explanatory views of the operation of the second embodiment.
Figure 7B:
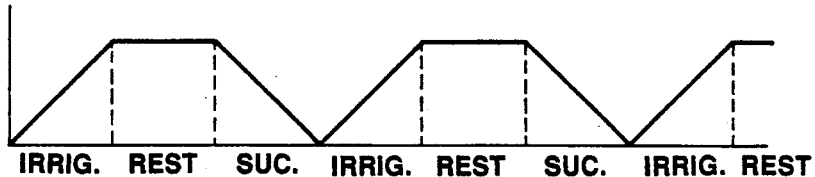

FIGS. 7a and 7b show the action states in this embodiment when a stop operation is not performed. In the drawings, irrigation and suction or irrigation, rest and suction are repeated in the same way as in the above-described embodiment.

Figure 8:
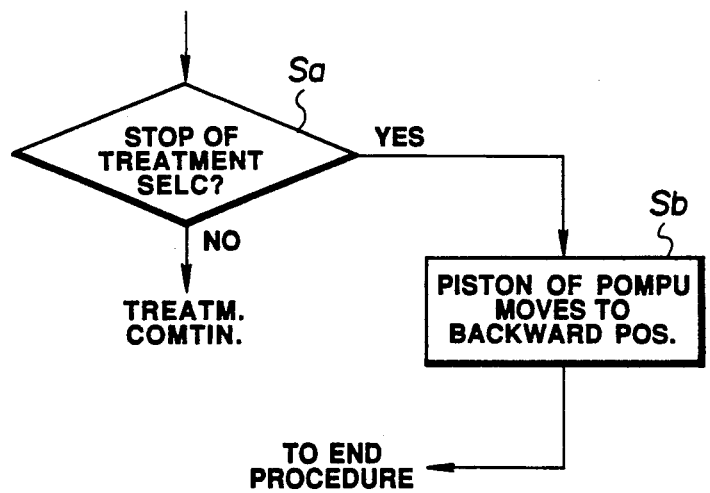

As shown by the flow chart in FIG. 8, when a treatment stop or an apparatus stop of is selected during the treatment using the litholysis apparatus in this embodiment, the control apparatus 66 decides in Step Sa that the stoppage is selected, and the piston 62 is backwardly moved until the detection signal is output from the backward detector 65 so that the whole of the lithotriptic remaining in the human body at the time the stoppage is selected is discharged by suction. The operation of the apparatus is then stopped.

Figure 7C:

For example, when a stop operation is performed in an intermediate position in the second treatment routine TR2 shown in FIG. 7a, the control apparatus 66 detects this and backwardly moves the piston 62 so as to stop the treatment when the detection signal is detected by the backward detector 65. The action in this case is shown in FIG. 7c.

Figure 9:
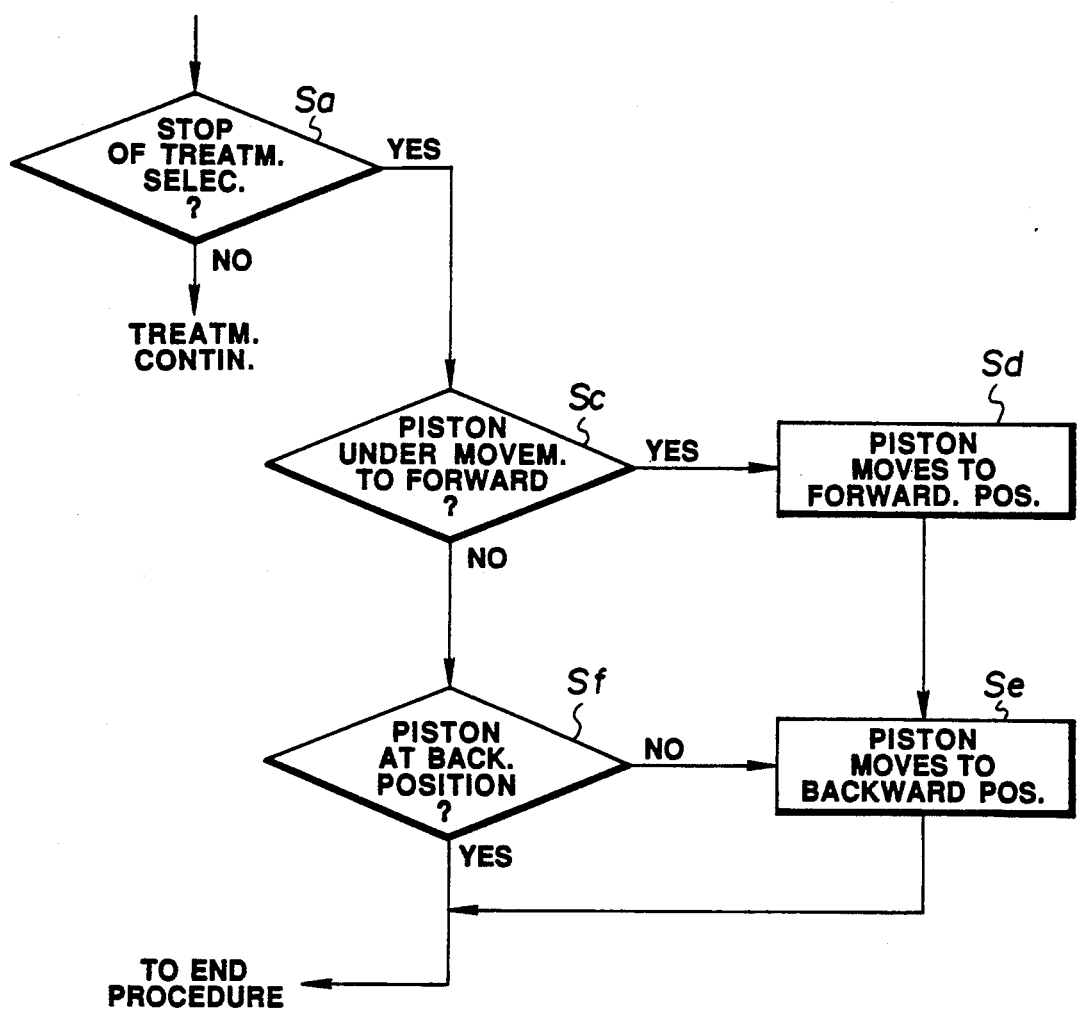

The flow chart shown in FIG. 9, which is different from the flow chart shown in FIG. 8, may be used.

Namely, when the result of the decision made in Step Sa whether or not the treatment is stopped is YES, a decision is made in Step Sc as to whether or not the piston is under forward movement. When the result of this decision is YES, the piston is moved to the forward position, as shown in Step Sd. The piston is then moved to the backward position and stopped, as shown in Step Se.

When the result of the decision made in Step Sc is NO, a decision is made as to whether or not the piston is at the backward position, as shown in Step Sf. If the piston is at the backward position, the processing is completed, and if the piston is not at the backward position, the processing in Step Se is performed, and the treatment is then stopped.

Figure 7D:

FIG. 7d shows the action when the stop treatment is performed in accordance with the flow chart shown in FIG. 9.

For example, when a treatment stop is selected in the course of the second routine TR2, if the piston 62 is under the forward movement (under irrigation), the piston 62 is continuously moved to the forward position. After a regular quantity of lithotriptic has been introduced, the piston is backwardly moved so that the lithotriptic remaining in the human body is discharged by suction by a regular suction action.

Figure 7E:
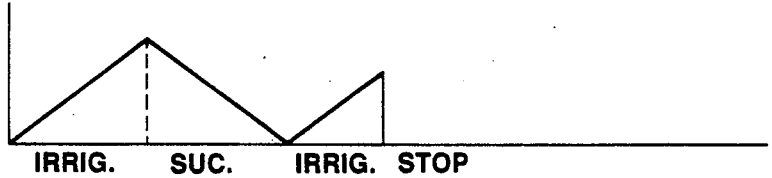

In this embodiment, when the stoppage is selected during the suction discharge of the lithotriptic, the operation of the apparatus is completely stopped in the same way as in the first embodiment. This embodiment thus can cope with the high-emergency stop of the apparatus. FIG. 7e shows the action of this embodiment.

The litholysis apparatus of this embodiment, which has the above-mentioned configuration and function, exhibits the same effect as that of the first embodiment and thus permits safe stop of the treatment action.

Figure 10:
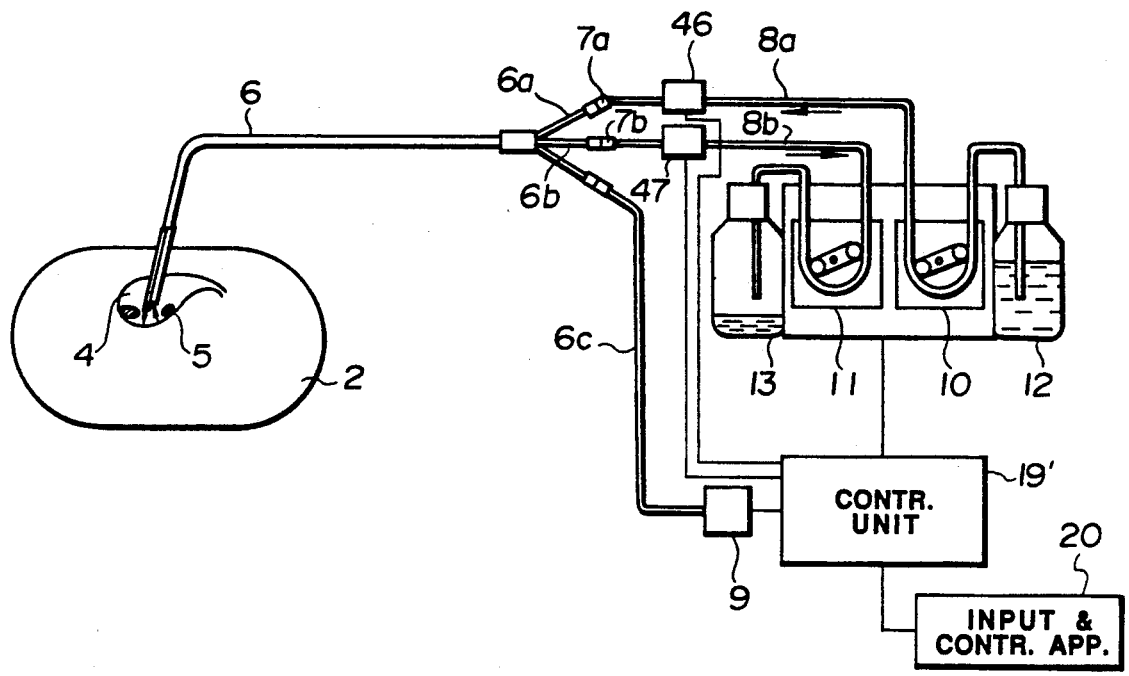
Figure 11:
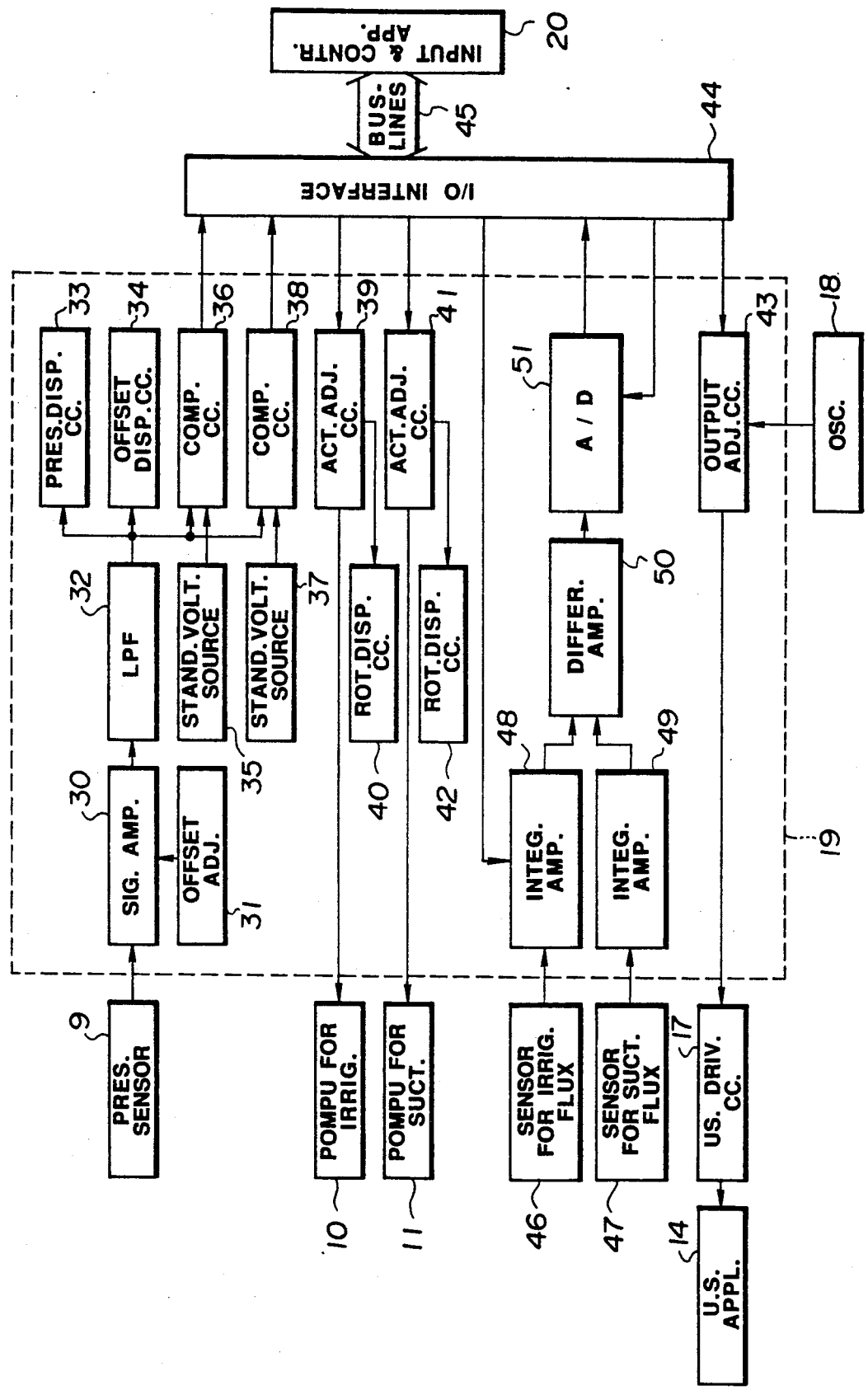

FIG. 10 is a schematic drawing of the circulation system of a litholysis apparatus in a third embodiment of the present invention. In this embodiment, the circulation action may be carried out by a method of repeating irrigation and suction or a method of simultaneously introducing and sucking the lithotriptic to continuously circulate it. In the drawing, an irrigation flux sensor 46 and a suction flux sensor 47 are respectively provided at intermediate positions of an irrigation pump tube 8a and a suction pump tube 8b for the purpose of detecting the irrigation flow and the suction flow. The sensors 46, 47 are connected to a control unit 19' so that detection signals are input thereto. FIG. 11 is a block diagram which shows the configuration of the control unit 19' of the litholysis apparatus in this embodiment. The irrigation flux sensor 46 and the suction flux sensor 47 are connected to integral amplifiers 48, 49, respectively. The integrated flow signal output from each of the amplifiers 48, 49 is converted into an integrated flow difference signal which is then input to a A/D converter 51. A control signal for resetting integration output is input to the integral amplifiers 48 and 49 from the input/control apparatus 20 through an I/O interface 44. The A/D converter 51 outputs the integrated flux difference signal, which is converted into a digital signal, to the input/control apparatus 20 on the basis of the control signal output from the input/control apparatus 20. The switches 97, 98 and the data input means 99, which are shown in FIG. 4, are not shown in FIG. 11.

Figure 12:
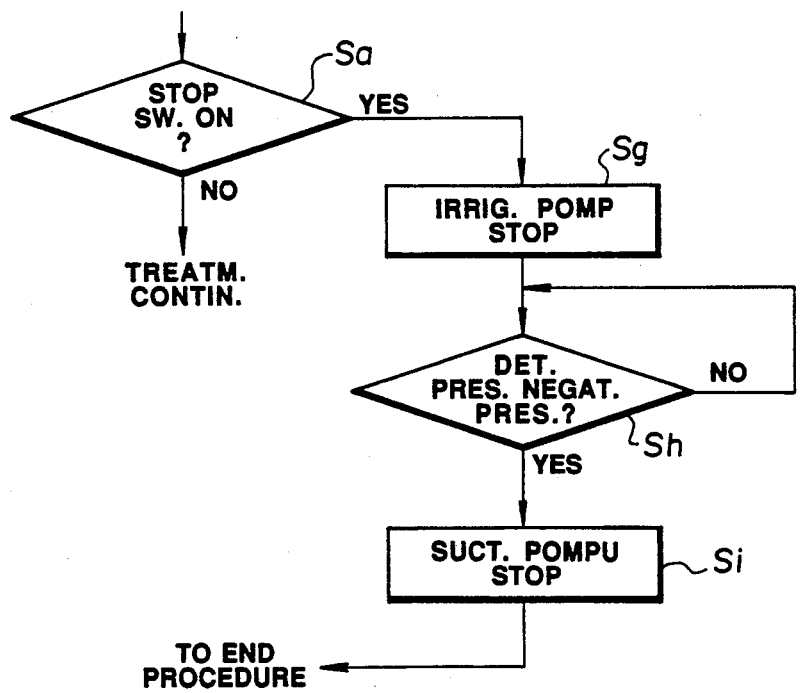

FIG. 12 shows the state of the control action of the input/control apparatus 20 which is related to the treatment stop and end in the litholysis apparatus of this embodiment. In the drawing, when the treatment stop is selected by the operator, the irrigation pump 10 is immediately stopped, as shown in Step Sg. In the next Step Sh, the pressure signal detected by the pressure duct 6c in the catheter 6, which is inserted into the gallbladder, and the pressure sensor 9, which is connected to the pressure duct 6c, is compared with the standard voltage signal, which shows atmospheric pressure, in the control unit 19'. The comparison signal is output to the input/control apparatus 20. The input/control apparatus 20 thus performs suction discharge of the lithotriptic remaining in the gallbladder on the basis of the comparison signal until the pressure in the gallbladder becomes the atmospheric pressure or less, e.g., negative. When the pressure in the gallbladder is negative, the suction pump 11 is stopped, and the operation of the apparatus moves to the end procedure (as shown in Step Si).

In this way, the remaining lithotriptic can be surely and simply discharged by suction only by a suction action under monitoring of the pressure in the gallbladder.

Figure 13:
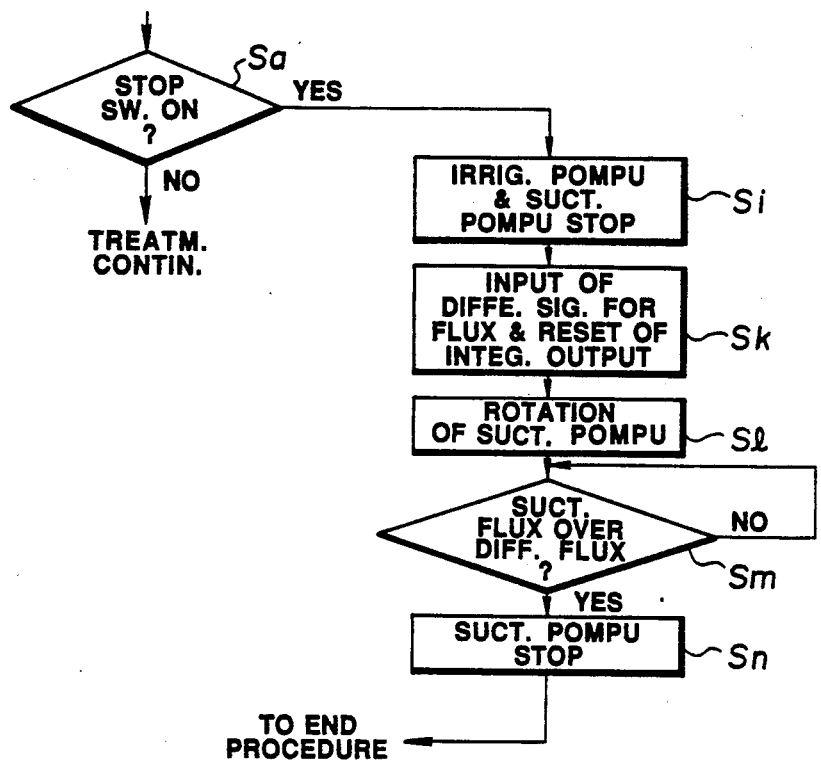

FIG. 13 is a drawing provided for explaining the state of another treatment stop and end action in this embodiment.

When treatment stop or end, i.e., the stop of the apparatus, is selected, the irrigation pump 10 and the suction pump 11 are stopped, as shown in Step Sj. As shown in Step Sk, the integrated flux difference signal between irrigation and suction at the stop time is subjected to A/D conversion and then input to the input/control apparatus 20 and stored therein, and the output from the integral amplifiers 48 and 49 is then reset. The suction discharge of the remaining lithotriptic is then started by the action of the suction pump 11, as shown in Step Sl. During the suction discharge, the accumulated quantity of the lithotriptic discharged by suction is constantly monitored by the input/control apparatus 20, as shown in Step Sm. When the accumulated quantity of suction discharge is equal to the accumulated flux difference between irrigation and suction, as shown in Step Sn, the action of the suction pump 11 is stopped, and the action of the apparatus moves to the end procedure.

In this embodiment, when the stoppage is selected during the suction discharge of the lithotriptic, the operation of the apparatus is completely stopped in the same way as in the above-described embodiments. This embodiment thus can cope with emergency stop of the apparatus.

The litholysis apparatus of this embodiment having the above-mentioned configuration and function exhibits the same effect as that obtained in the above embodiments and is capable of safely stopping the treatment action. The embodiment also has the extremely useful effect of realizing a safe stop of the apparatus in either of a sequential circulation system or a continuous circulation system.

In addition, when a power supply to the litholysis apparatus is stopped in each of the first, second and third embodiments, the power source is switched to the auxiliary small power source (not shown), which is loaded on the apparatus body, by a power monitor circuit and a power switching circuit which are not shown in the drawings so that the action of suction discharge of the lithotriptic remaining in the human body is carried out assuming that the stop of the power supply is the stop of the treatment. This causes further improvements in the action of the apparatus and the safety of treatment.

Figure 14:
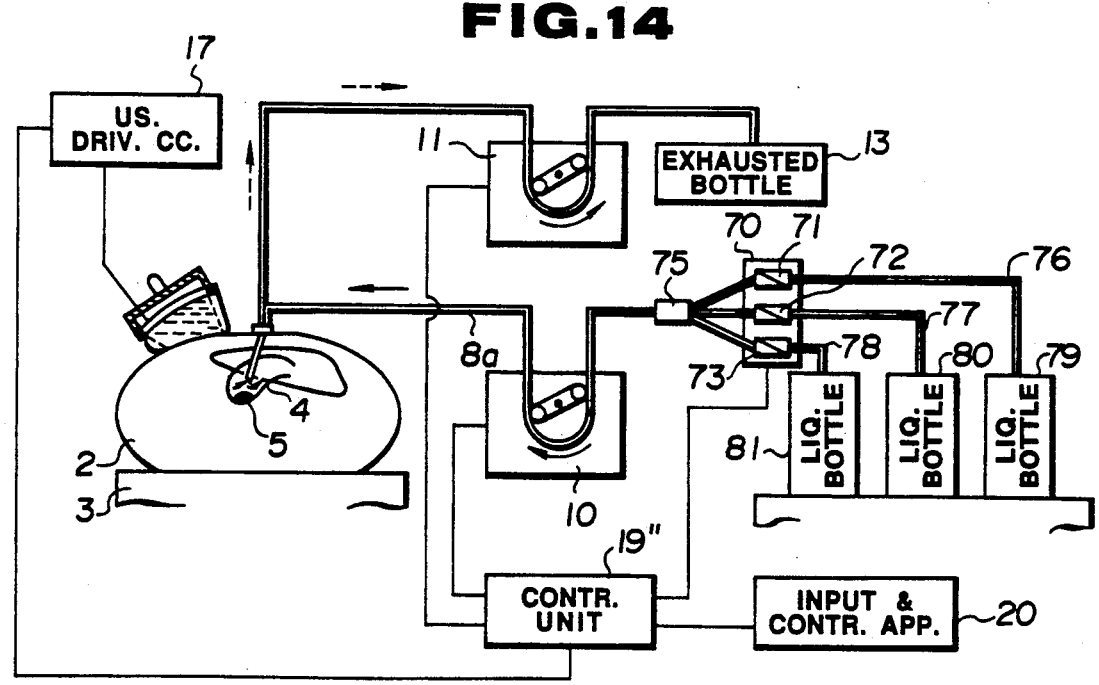

FIG. 14 shows the configuration of the circulation system in a fourth embodiment of the present invention.

Although the fourth embodiment has substantially the same configuration as that of the first embodiment, this embodiment is different from the first embodiment in a pretreatment mechanism for switching the lithotriptic and physiological saline. The same components as those in the first embodiment are denoted by the same reference numerals and are not described below.

In FIG. 14, one end of a liquid-sending tube 8a is branched into three portions through a collecting connector 75. Reference numeral 70 denotes a medical fluid switching part comprising three solenoid valves 71, 72, 73 which are connected to liquid-sending tubes 76, 77, 78, respectively, which are branches from the collecting connector 75. The liquid-sending tubes 76, 77, 78 are connected to liquid bottles 79, 80, 81, respectively. Although the liquid bottles 79, 80, 81 are capable of receiving any liquids, in this embodiment, a physiological aline (referred to as "saline" hereinafter), a cholesterol lithotriptic and a bilirubin lithotriptic are stored in the liquid bottles 79, 80, 81, respectively. The solenoid valves 71, 72, 73 are electrically connected to a control unit 19″.

Figure 15:
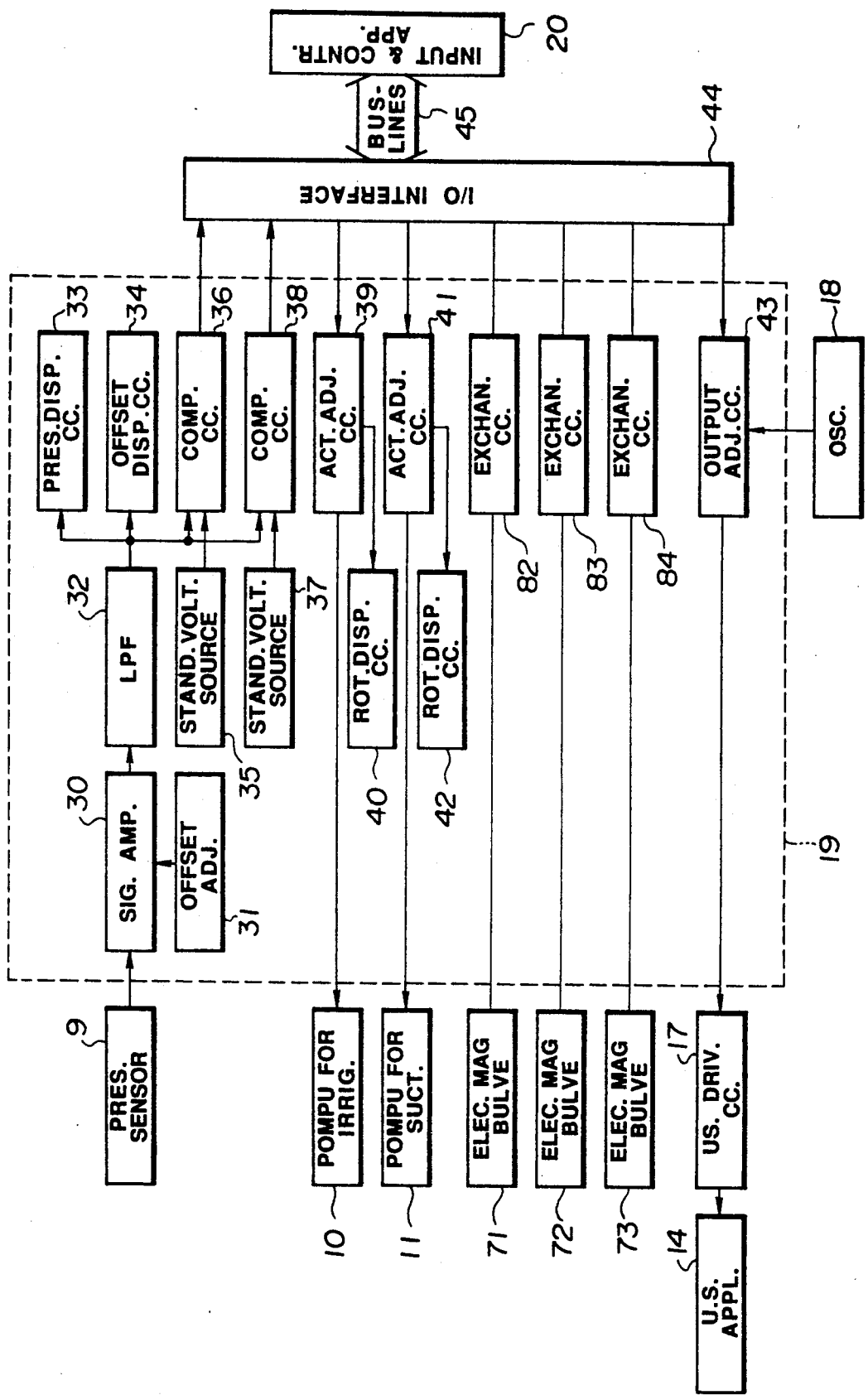

The detailed structure of the control unit 19″ shown in FIG. 14 is shown by the dotted line in FIG. 15. The input terminals of the solenoid valves 71, 72, 73 are connected to change-over circuits 82, 83, 84, respectively, for controlling the opening and closing of the valves. The input terminals of the change-over circuits 82, 83, 84 are connected to the output terminal of the I/O interface 44. The switches 97, 98 are not shown in the drawing, and the pressure sensor 9 shown in FIG. 15 is not shown in FIG. 14.

The function of the litholysis apparatus in this embodiment configured as described above is described below.

In the litholysis apparatus of the embodiment, the lithotriptic is introduced and sucked by the actions of the irrigation pump 10 and the suction pump 10, respectively, and a sequence of pre-treatment for automatically discharging the bile and washing the interior of the gallbladder by irrigation by saline is provided before a sequence of control of litholysis treatment comprising an irrigation action and a suction action, and, if required, a standing step of allowing the lithotriptic to be stored in the gallbladder therebetween.

Figure 16:
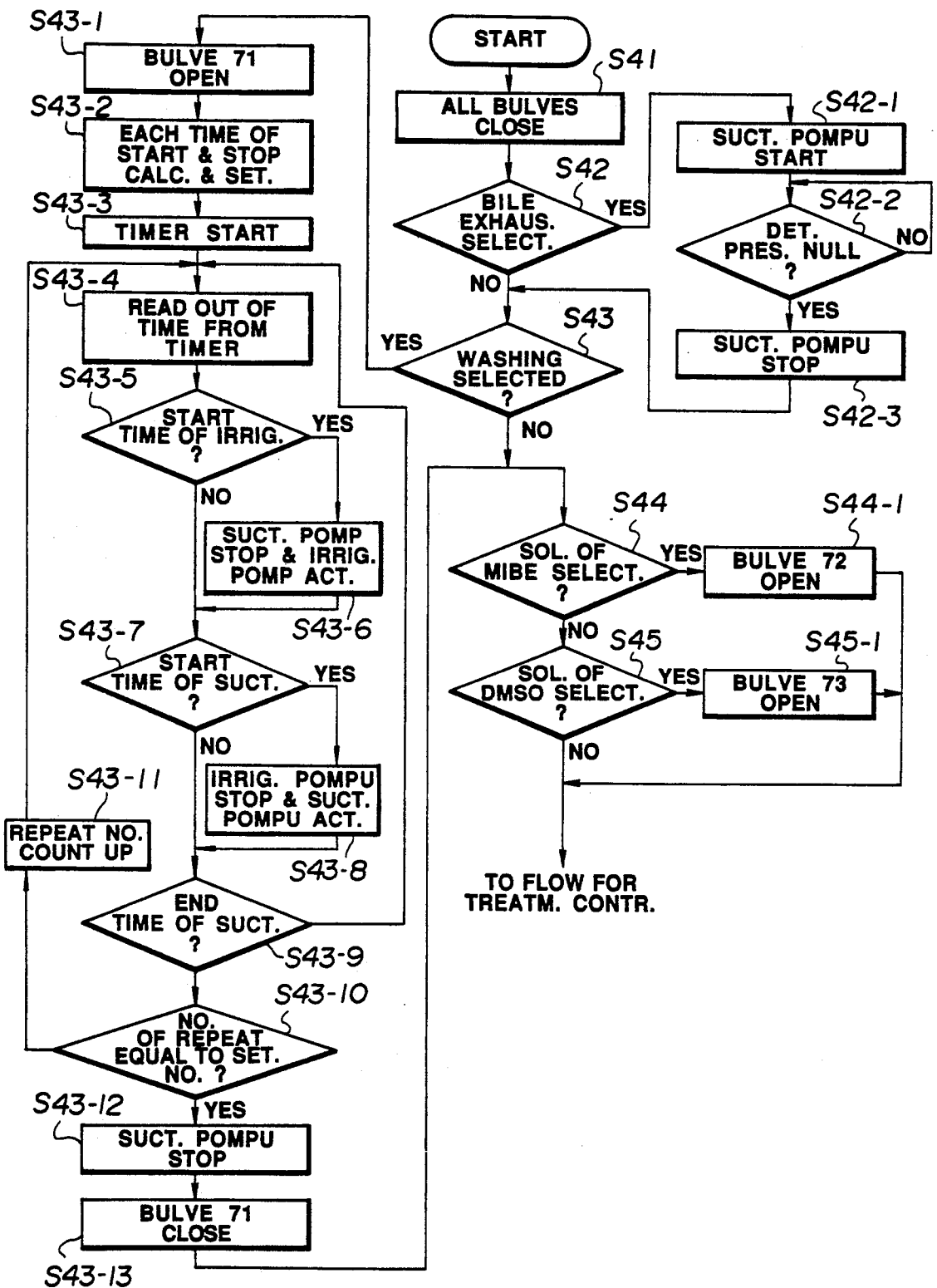

On the basis of the flow chart shown in FIG. 16, all the solenoid valves 71, 71, 73 are closed at the start of treatment, as shown in Step S41. The operator then selects the action of discharging the bile and the action of washing with the saline by using the input/control apparatus 20, as shown in Steps S42, 43. When the action of discharging the bile is selected, the suction pump 11 is started, as shown in Step S42-1, the suction pump 11 is driven until the pressure in the gallbladder is zero in Step S42-2, and the suction pump 11 is then stopped in Step S42-3.

When the action of saline washing is then selected, as shown in Step S43-1, the solenoid valve 71 is opened, the start time and end time of each of the pumps are calculated and set in the input/control apparatus 20 (Step S43-2), and the timer is started (Step S43-3). In the control apparatus 20, the time is read from the timer (Step S43-4), and a decision is made as to whether or not the read time is the irrigation start time (Step S43-5). At the irrigation start time, the suction pump 11 is stopped, and the irrigation pump 10 is started (Step S43-6).

A decision is then made as to whether or not the time is the suction start time (Step S43-7). At the suction start time, the irrigation pump 10 is stopped, and the suction pump 11 is rotated (started) (Step S43-8).

After the suction pump 11 has been started, a decision is made as to whether or not the time the suction end time (Step S43-9) and whether or not a predetermined number of pretreatments is made (Step S43-10). In a case of NO, the number of repetitions is counted up (Step S43-11), and the processing returns to Step S43-4

In a case of YES, the suction pump 11 is stopped (Step S43-12), the solenoid valve 71 is closed (Step S43-13), and the medical fluid used is selected.

The solenoid valve 72 or 73 is opened (Steps S44-1, S45-1) in correspondence with the selection of the cholesterol lithotriptic or the bilirubin lithotriptic by the input/control apparatus 20 (Steps S44, S45). The processing then moves to the next treatment control flow (for example, Step S1 shown in FIG. 1a).

A stop treatment may be made in the course of the flow shown in FIG. 16.

The treatment in accordance with the flow shown in FIG. 16 may be provided between Steps S1 and S2 shown in FIG. 1a. In this case, the data items for pretreatment selected in Steps S43, S44 and S45 are input in Step S1 so that the pretreatment and the subsequent curative treatment are automatically made in accordance with the data input.

This fourth embodiment has the same advantage as that of the first embodiment, as well as an advantage in that the trouble of the operation performed by the operator for curative treatment can be reduced, and the load on the operation can be thus reduced.

Figure 17:
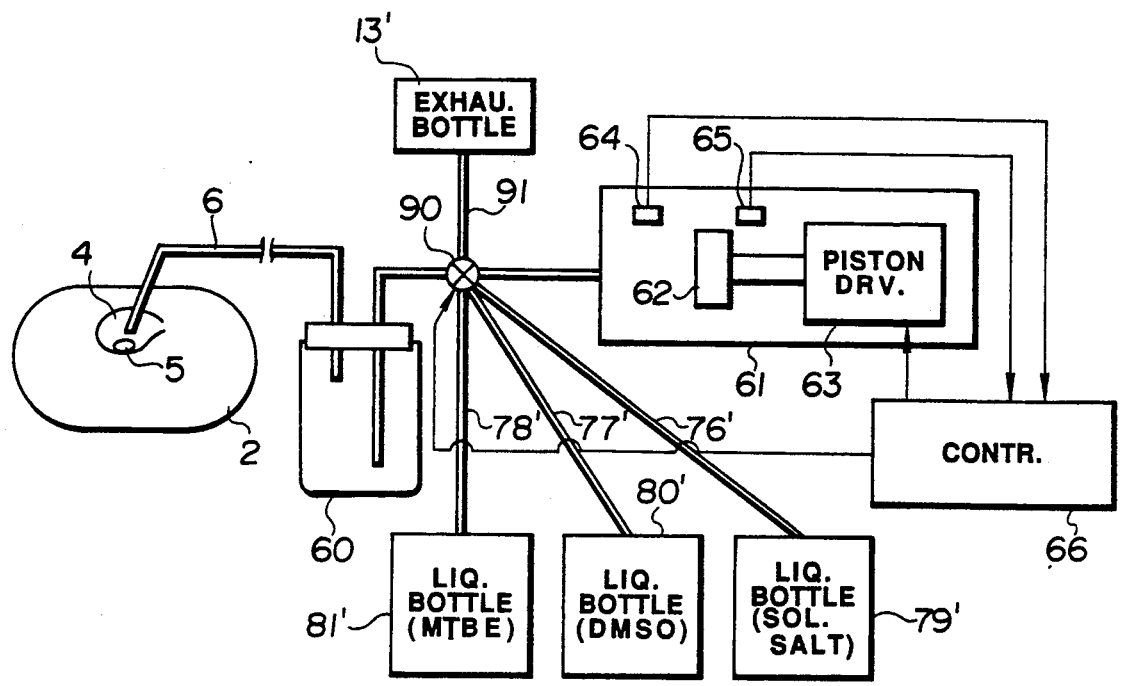

FIG. 17 shows the configuration of a circulation system in a fifth embodiment of the present invention.

This fifth embodiment comprises the step of controlling (controlling pretreatment) so as to automatically discharge the bile and wash the interior of the gallbladder by irrigation with saline before curative treatment in the same way as in the fourth embodiment. However, the fifth embodiment is different from the fourth embodiment in the configuration of the circulation system. Although the circulation system has an configuration similar to that of the second embodiment, the function to switch the lithotriptic and the saline is added thereto. Namely, a change-over valve 90 is provided at an intermediate position of the catheter connecting the pump 60 and the pump 61 in the second embodiment, and one end of each of liquid-sending tubes 76', 77', 78', which are branches from the change-over value 90, and one end of an exhaust tube 91 are connected to the change-over valve 90. The other ends of the liquid-sending tubes 76', 77', 78' are respectively connected to liquid bottles 79', 80', 81' in which saline, a cholesterol lithotriptic and a bilirubin lithotriptic are respectively stored. The other end of the exhaust tube 91 is connected to an exhaust bottle 13'.

The switching of the change-over valve 90 is controlled synchronously with the action of the pump 61 by the control apparatus 66. The contents of the action of the fifth embodiment are shown in FIG. 18.

After the operation of the apparatus has been started, if the discharge of the bile is selected in a decision as to whether or not the bile is discharged(Step S51), after the number of repetitions has been set (Step S51-1), the piston 61 is brought into a forward movement state, and the valve 90 is opened so that the trap 60 communicates with the pump 61 (Step S51-2). The piston 62 is then backwardly moved so that the bile is introduced into the pump 61 by suction, and the valve 90 is then switched so that the trap 60 communicates wit the exhaust bottle 13' (Step S51-3). The piston 62 is then forwardly moved so that the bile introduced into the pump 61 is discharged to the exhaust bottle 13' (Step S51-4). A decision is then made as to whether or not the number of repetitions reaches a set number (Step S51-5). In a case of NO, the processing returns to Step S51-2. If the number of repeated actions reaches the set number, a decision is made as to whether or not the saline washing action is made (Step S52). If the washing is selected, after a number of repetitions has been set (Step S52-1), the valve 90 is switched so that the trap 60 communicates with the liquid bottle 79'. The piston 62 is backwardly moved so that the saline is received in the pump 61 (Step S52-2).

The valve 90 is then switched so that the trap 60 communicates with the pump 61, and the piston 62 is forwardly moved so that the saline received in the liquid bottle 79' is introduced (Step S52-3). After the irrigation, the piston 62 is backwardly moved so as to effect suction (Step S52-4). The valve 90 is then switched so that the pump 61 communicates with the exhaust bottle 13', and the piston 62 is forwardly moved so that the liquid sucked in the pump 61 is discharged to the exhaust bottle 13' (Step S52-5). A decision is then made as to whether or not the number of repetitions reaches the set number (Step S52-6). In a case of NO, the processing returns to Step S52-2, and the action is repeated until the number of repetitions reaches the set number. The medical fluid used is then selected. Namely, a decision is made as to whether or not the cholesterol lithotriptic is selected (Step S53). If it is selected, the valve 90 is switched so that the pump 61 communicates with the liquid bottle 80', and the piston 62 is backwardly moved so that the lithotriptic is introduced into the pump 61 (Step S53-1). If the bilirubin lithotriptic is selected in the decision made as to whether or not the bilirubin lithotriptic is selected (Step S54), the valve 90 is switched so that the pump 61 communicates with the liquid bottle 81', and the piston 62 is backwardly moved so that the lithotriptic is introduced into the pump 61 (Step S54-1).

The valve 90 is then switched so that the trap 60 communicates with the pump 61 (Step S53), and the processing moves to the flow of treatment control.

This embodiment causes a reduction in the operation performed by the operator, as compared with the second embodiment.

Figure 19:
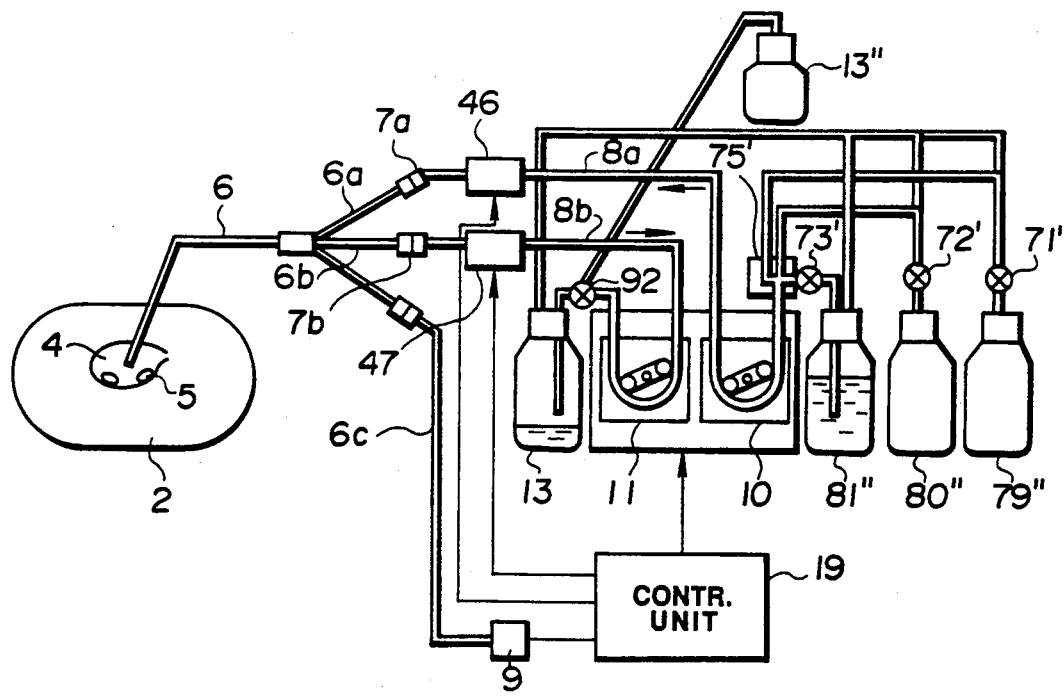

FIG. 19 schematically shows a circulation system in a sixth embodiment of the present invention.

The sixth embodiment has the control function to automatically discharge the bile and wash the interior of the gallbladder by irrigation with saline (pretreatment) before litholysis in the same way as in the fourth or fifth embodiment. However, the configuration of the circulation system in this embodiment is different from those in the fourth and fifth embodiments.

The circulation system in this embodiment is provided with the function to switch the saline and the lithotriptic, which is similar to that in the third embodiment.

Namely, liquid bottles 79", 80", 81", in which saline, a cholesterol lithotriptic and a bilirubin lithotriptic are respectively received, are provided in place of the single liquid bottle 12 of the second embodiment shown in FIG. 10.

In addition, a receiving bottle 13" for receiving the bile sucked is provided so that the exhaust bottle 13 or the receiving bottle 13" can be selected by a valve 92.

The liquid bottles 79", 80", 81" are provided with valves 71', 72', 73', respectively, and are connected to the irrigation pump 10 through the valves 71', 72', 73'. Reference numeral 75' denotes a three-way connector.

The opening and closing of the valves 92, 71', 72', 73' are controlled by the input/control apparatus 19.

The action of this embodiment is described below with reference to the control flow shown in FIG. 20.

When the action of the apparatus is started, all the solenoid valves are closed (Step S61), the bile discharge is selected (Step S62) and the washing by irrigation with the saline is selected (Step S63). The valve 92 is then opened so as to communicate with the exhaust bottle 13 (Step S64), and processing of the selection of the medical fluid is performed. Namely, a decision is made as to whether or not the cholesterol lithotriptic is selected (Step S65) or the bilirubin lithotriptic is selected (Step S66), and the processing moves to the flow of treatment control.

If the bile discharge is selected in Step S62, the valve 92 is opened so as to communicate with the receiving bottle 13" (Step S62-1), and the suction pump 11 is then operated so as to suck the bile. The bile sucked is discharged to the receiving bottle 13" (Step S62-2). During this discharge, a decision is made as to whether or not the pressure detected is zero (Step S61-3), and the suction action is continued until the pressure becomes zero. The suction pump 11 is then stopped (Step S61-4), and the processing moves to Step S63.

If the saline washing is selected, the valve 92 is opened so as to communicate with the exhaust bottle 13", and the valve 71' is also opened (Step S63-1). When both the pumps 10 an 11 are operated, the saline is introduced, and the liquid sucked is discharged to the exhaust bottle 13" (Step S63-2). The action is continued to a set time on the basis of the result of a decision is made as to whether or not the action is finished (Step S63-3). Both the pumps 10 and 11 are then stopped (Step S63-4), and the valve 71' is closed (Step S63-5). The medical fluid used is the selected.

When the cholesterol lithotriptic is selected, the valve 72' is opened (Step S65-1), and if the bilirubin lithotriptic is selected, the valve 73' is opened (Step S66-1). After the preparation for irrigation with the medical fluid has been made, the processing moves to the next step of treatment control.

The sixth embodiment also permits a reduction in the load on the operator, as compared with the third embodiment. This embodiment also has an advantage to the patient in that the treatment time is reduced owing to the smooth pretreatment.

Figure 21:
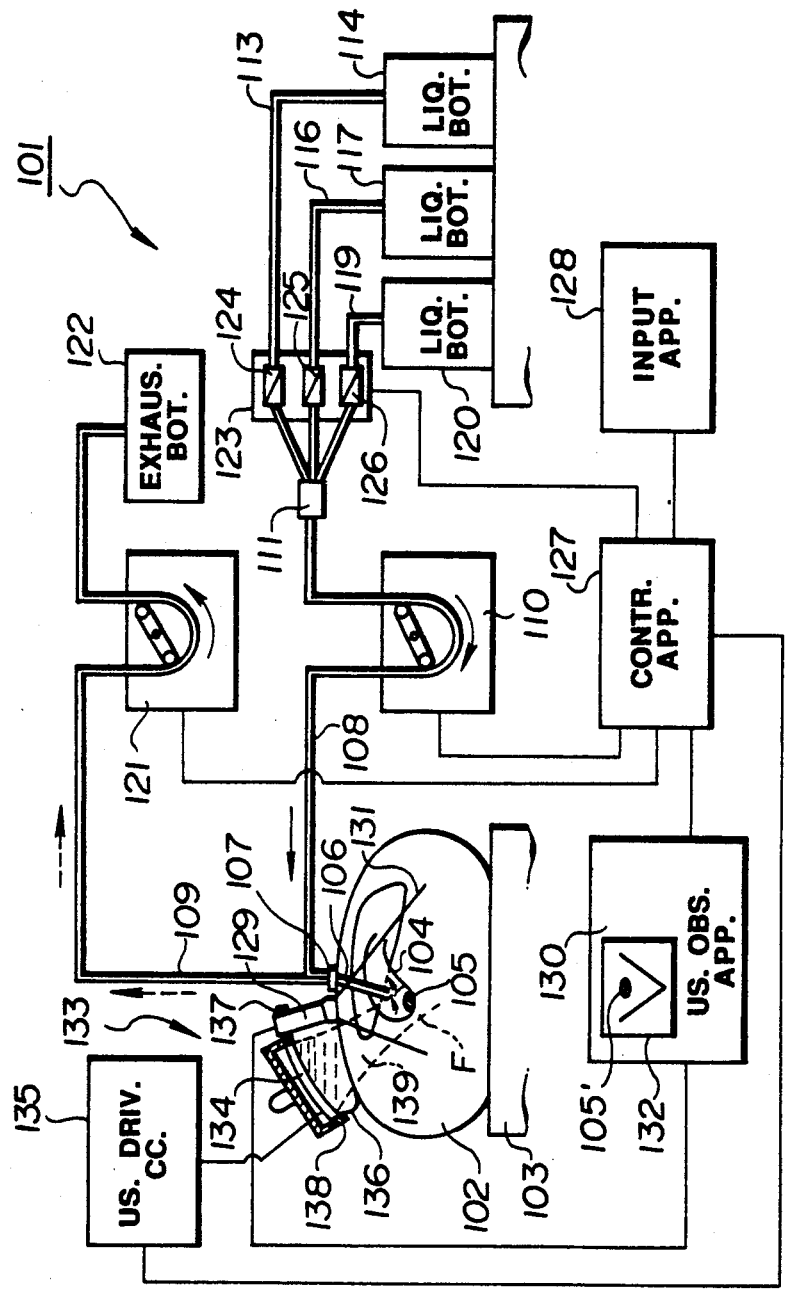
FIG. 21 is a drawing of the configuration of the circulation system in a seventh embodiment of the present invention.

FIG. 21 shows a seventh embodiment of the present invention. In FIG. 21, reference numeral 101 denotes a litholysis apparatus; reference numeral 102, a human body; reference numeral 103, a medical table; reference numeral 104, the gallbladder in the body; reference numeral 105, a calculus in the gallbladder; and reference numeral 106, tube which is buried in the human body. The tube 106 is connected to a liquid-sending tube 108 and an discharge tube 109 through a connector 107. A liquid sending pump 110 is disposed at an intermediate position of the liquid-sending tube 108, and the other end of the tube 108 is branched into three ways through a collecting connector 111. The three branches are connected to a medical fluid switching part 123 and respectively connected to liquid bottles 114, 117, 120 through liquid sending tubes 113, 116, 119 which are respectively provided with solenoid valves 124, 125, 126 in the switching part 123. The opening and closing of the valves 124, 125, 126 are controlled by a control apparatus 127. An exhaust pump 121 is disposed at an intermediate position of the exhaust tube 109, the other end being connected to an exhaust bottle 122.

Although any liquids can be received in the liquid bottles 114, 117, 120, in this embodiment, physiological saline, MTBE serving as a cholesterol lithotriptic and DMSO serving as a bilirubin lithotriptic are received in the liquid bottles, 114, 117 and 120, respectively. Further, a probe 129 may be provided on the surface of the human body near the connector 107, the probe 129 being connected to an ultrasonic observation apparatus 130. Thus, a sectoral scanning region 131 including the gallbladder 104 in the human body 102 can be observed, and the observation image can be displayed on a monitor of the ultrasonic observation apparatus 130. The ultrasonic observation apparatus 130 is electrically connected to the control apparatus 127.

As a result, an ultrasonic image of the treatment part can be obtained by the ultrasonic probe 129. An image 105' of a calculus 105 can be displayed on the monitor when the probe 129 is brought into contact with the human body. Since the image 105' depends upon the size and kind of the calculus 105, the kind of the calculus 105 is estimated on the basis of the image 105' obtained, and a menu for sending and discharging the lithotriptic suitable for the calculus 105 is input to an input apparatus 128. In addition, the necessary quantity of the lithotriptic is calculated on the basis of the size of the calculus image 105' so that the number of repetitions of sending and discharge of the liquid can be previously set. Further, the dose of the lithotriptic can be corrected on the basis of the size of the calculus image 105' during litholysis treatment, i.e., the elimination rate of the calculus by litholysis. In this way, the operator can manually input and operate the control apparatus 127. An image processing apparatus (not shown) can also be used for indicating the echo range of the calculus image 105' displayed on the monitor 132 by a light pen or the like, converting the change in size of the echo into an electrical signal and sending it to the control apparatus 127, whereby the sending and discharge of the lithotriptic can be controlled.

An external ultrasonic generator 133 is also provided for accelerating the litholysis. As is generally known, this external ultrasonic generator 133 has a single or a plurality of ultrasonic piezoelectric transducers 134 so that the ultrasonic wave generated from the ultrasonic piezoelectric transducers 134 driven by an ultrasonic driving circuit 135 is applied to a region F in the human body 102. The ultrasonic piezoelectric transducers 134 are fixed to the body of the external ultrasonic generator 133 by a ring-shaped transducer fixing member 138, and a water bag 136, which is made of a soft resin and which is filled wit an ultrasonic transfer liquid such as water or the like, is interposed between the ultrasonic piezoelectric transducer 134 and the human body 102. An ultrasonic probe holding tool 137, which outwardly projects, is formed in a portion of the body of the external ultrasonic generator 133 so that the ultrasonic probe 129 can be detachably held by the tool 137. The central axis of the sectoral observation region 131 agrees with the central axis of the ultrasonic irradiation region 139 of the external ultrasonic generator 133 in the region F in the human body 102. The ultrasonic driving circuit 135 is also connected to the control apparatus 127.

The function of the litholysis apparatus of the seventh embodiment configured as described above is the following:

The external ultrasonic generator 133 is first placed opposite to the human body 102, with the water bag 136 therebetween. The ultrasonic probe 129 is brought into contact with the human body 102 for the purpose of observing the interior of the human body 102. The external ultrasonic generator 133 is moved or fixed manually by the operator (not shown) or by a simple mounting apparatus. This operation causes the ultrasono-tomographic image of the interior of the human body 102 to be displayed on the monitor 132. The external ultrasonic generator 133 is moved to a position which allows the calculus image 105' to be displayed.

The medical fluid is then sent and discharged by operating the input apparatus 128 or on the basis of the ultrasonic observation image. As the same time, the ultrasonic driving circuit 135 is driven by the control apparatus 127 so as to apply an ultrasonic wave to a portion near the calculus 105. A given cycle of ultrasonic irradiation is repeated for making an attempt to promote dissolution. At this time, the timing of the sending and discharge of the medical fluid and ultrasonic irradiation can be previously set in the input apparatus 128 so that all the actions are automatically controlled by the control apparatus 127. As described above, since this embodiment is designed so that the ultrasonic wave is applied to the human body from the outside thereof, it is possible to further accelerate the dissolution of the calculus in the medical fluid and effect rapid and effective treatment.

Figure 22:
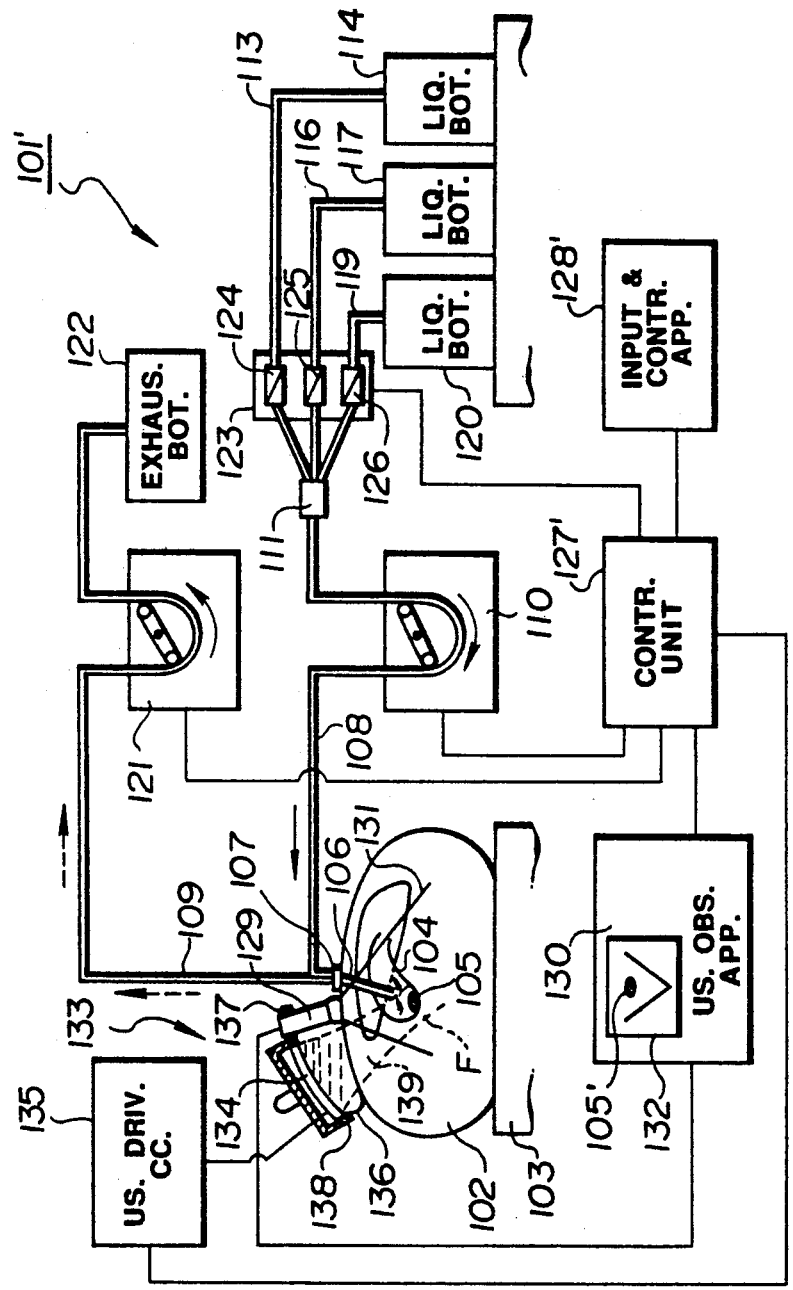

FIG. 22 shows an apparatus 101' in a modification of the seventh embodiment. In this modification, the control apparatus 127 and the input apparatus 128, which are shown in FIG. 21, are replaced by a control unit 127' and an input/control apparatus 128', the other components being the same as those in FIG. 21.

Figure 23:
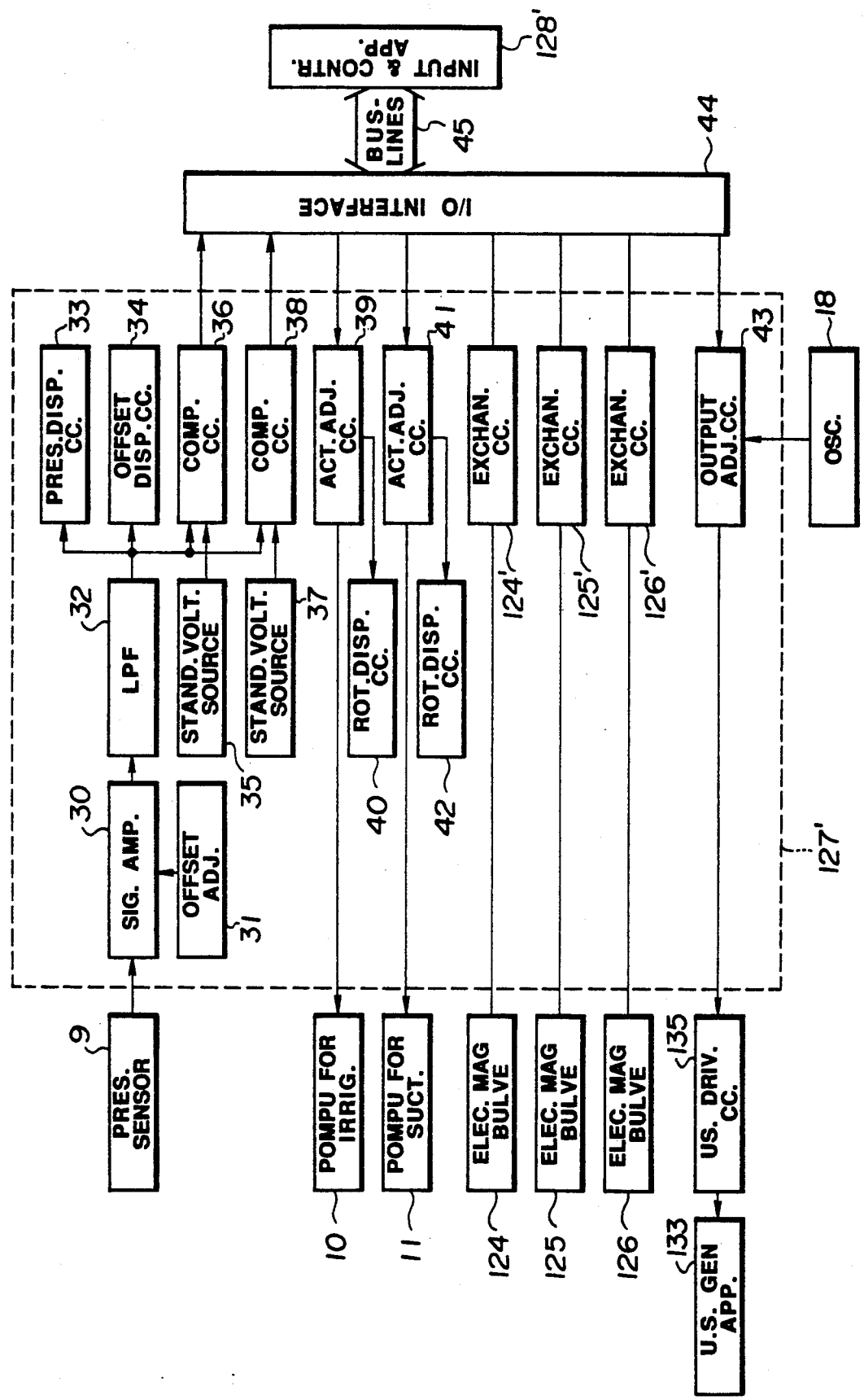

FIG. 23 shows the configuration of the control unit 127'. The control unit 127' is the same as the control unit 19 shown in FIG. 4 with the exception that change-over circuits 124', 125', 126' for controlling solenoid valves 124, 125, 126, respectively. The change-over circuits 124', 125', 126' are connected to the input/control apparatus 128' through the I/O interface and the bus line 45. Since the other components of the unit 127' are the same as those shown in FIG. 4, they are not described below. The switches 97, 98 shown in FIG. 4 are not shown in FIG. 23.

In this modification of the seventh embodiment, the medical fluid is automatically introduced and sucked under control by the input/control apparatus 128'. The control flow in this case is shown in FIG. 24.

Figure 24:
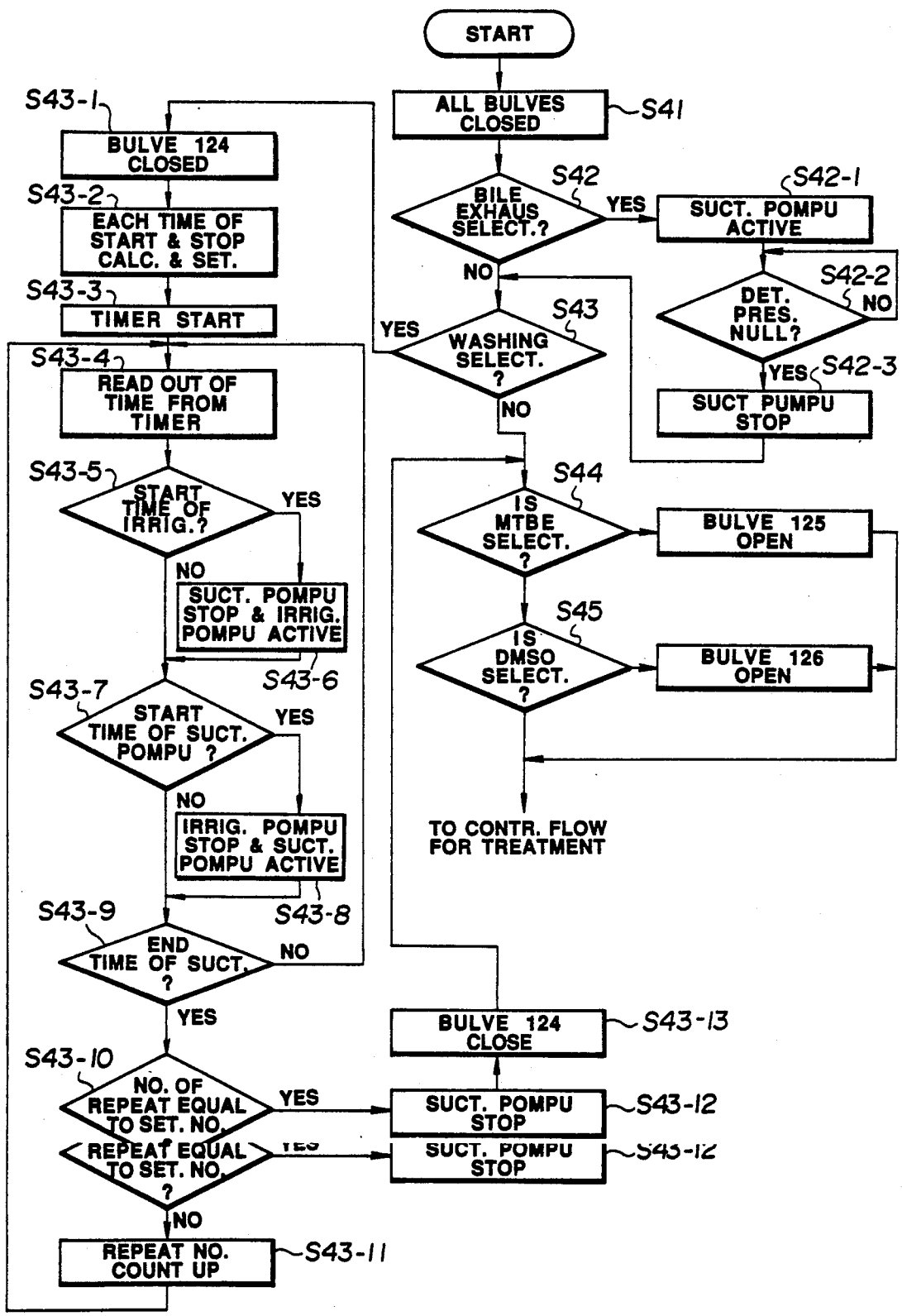

The control flow shown in FIG. 24 is substantially the same as that shown in FIG. 16 in which the same processing contents are denoted by the same reference numerals.

The operator first selects the bile discharge action or the saline washing action by using the input/control apparatus 128' (Steps S41, 42). If the bile discharge action is selected, the suction pump is started (Step S42-1) and driven until the pressure in the gallbladder becomes zero (Step S42-2). If the saline washing action is selected, the valve 124 is closed (Step S43-1), and the start and end times of each of the pumps are calculated and set in the input/control apparatus 128' (Step S43-2). The timer is then started (Step S43-3).

In the input/control apparatus 128', the time is read from the timer (Step S43-4), and a decision is made as to whether or not the read time is the start and end times of each of the irrigation pump and the suction pump so that the rotation and stop of each pump is controlled (Steps S43-5 to S43-9).

This action is repeated predetermined times and then stopped (Step S43-10). The suction pump is then stopped (Step S43-12), the valve 124 is closed (Step S43-13), and the medical fluid is then introduced. If the cholesterol lithotriptic is selected by the input/control apparatus 128', the solenoid valve 125 is automatically opened (Step S44-1), while if the bilirubin lithotriptic is selected, the solenoid valve 126 is automatically opened (Step S45-1).

The modification permits the pretreatment and the subsequent litholysis treatment to be made by a simple operation for a short time without any dead time and thus has a great advantage to the operator and the patient.

Figure 25:
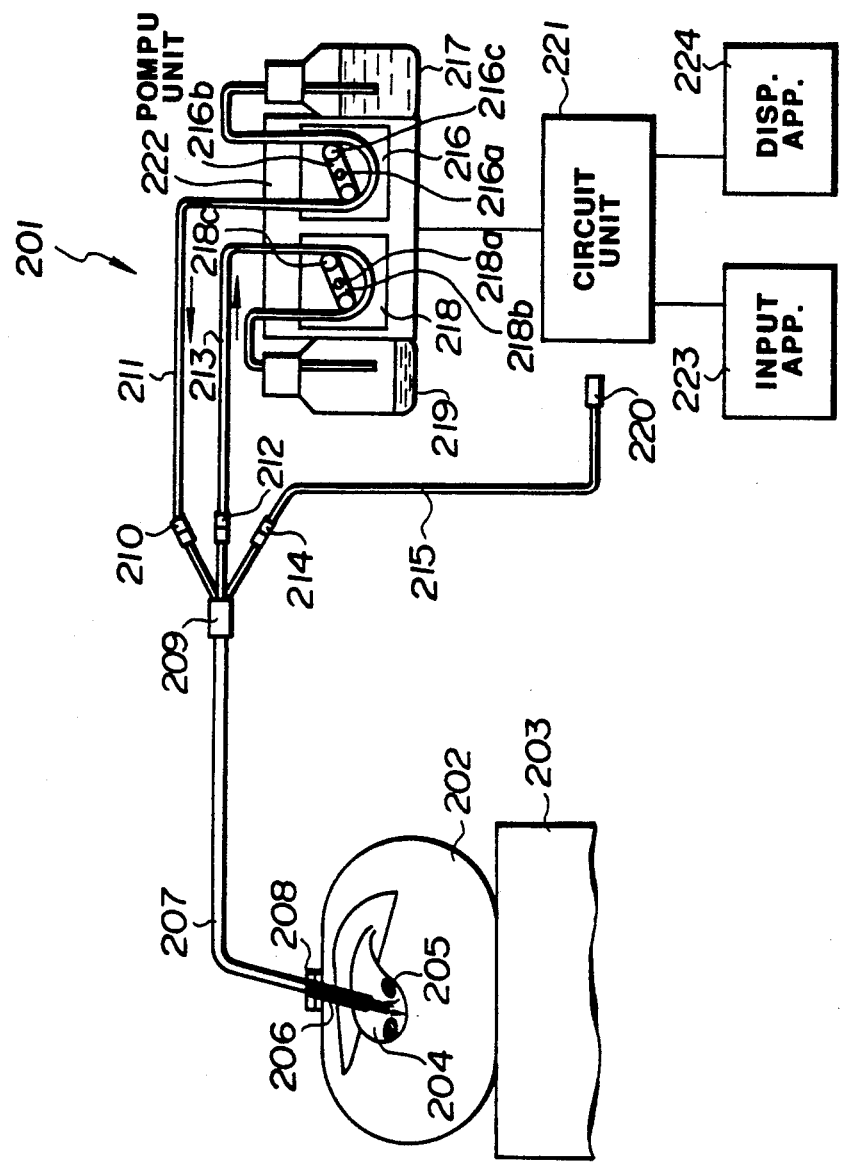

As shown in FIG. 25, the human body 202 subjected to treatment by a litholysis apparatus 210 in a eighth embodiment of the present invention lies down on a medical table 203, and a calculus 205 is produced in the gallbladder 4 in the human body 202, which is a portion subjected to treatment by the litholysis apparatus 201. An external sheath 206 is percutaneously inserted into the gallbladder 204, a catheter 207 being inserted into the inner hole of the external sheath 206. The end of the catheter 207 is placed in the gallbladder 204, and the external sheath 206 is detachably fixed to the catheter 207 through a connector 208 which is provided at the outer end of the external sheath 206. The catheter 207 has three ducts which are respectively connected to a liquid-sending tube 211, a exhaust tube 213 and a pressure duct 215 through a collecting connector 209 provided at the rear end of the catheter 207. The liquid-sending tube 211 has a cock 210 disposed near the connector, a liquid-sending (irrigation) pump head 216 disposed at an intermediate position and the other end which is connected to a liquid bottle 217 containing a lithotriptic, for example, monoctanoin, octodiol or methyl t-butyl ether (MTBE), on the side opposite to the connector 209. The exhaust tube 213 has a cock 212 disposed near the connector 209, an exhaust pump head 218 disposed at an intermediate position and the other end which is connected to a liquid bottle 219 for receiving the lithotriptic recovered from the treatment portion. The liquid-sending pump head 216 and the exhaust (suction) pump head 218 are of the same type, as shown in FIG. 25. Both the pump heads 216, 218 have rotating rollers 216c, 218c which are provided at both ends of rotors 216b, 218b fixed on output shaft 216a, 218a, respectively, of motors (not shown) so that the rollers 216c, 218c respectively press the tubes 211, 213 to constantly push a predetermined quantity of liquid. The pressure duct 215 is connected to the pressure sensor (described below) in a circuit unit 221 through a connector 220. To the circuit unit 221 are electrically connected a pump unit 222, an input apparatus 223 and a display apparatus 224.

Figure 26:
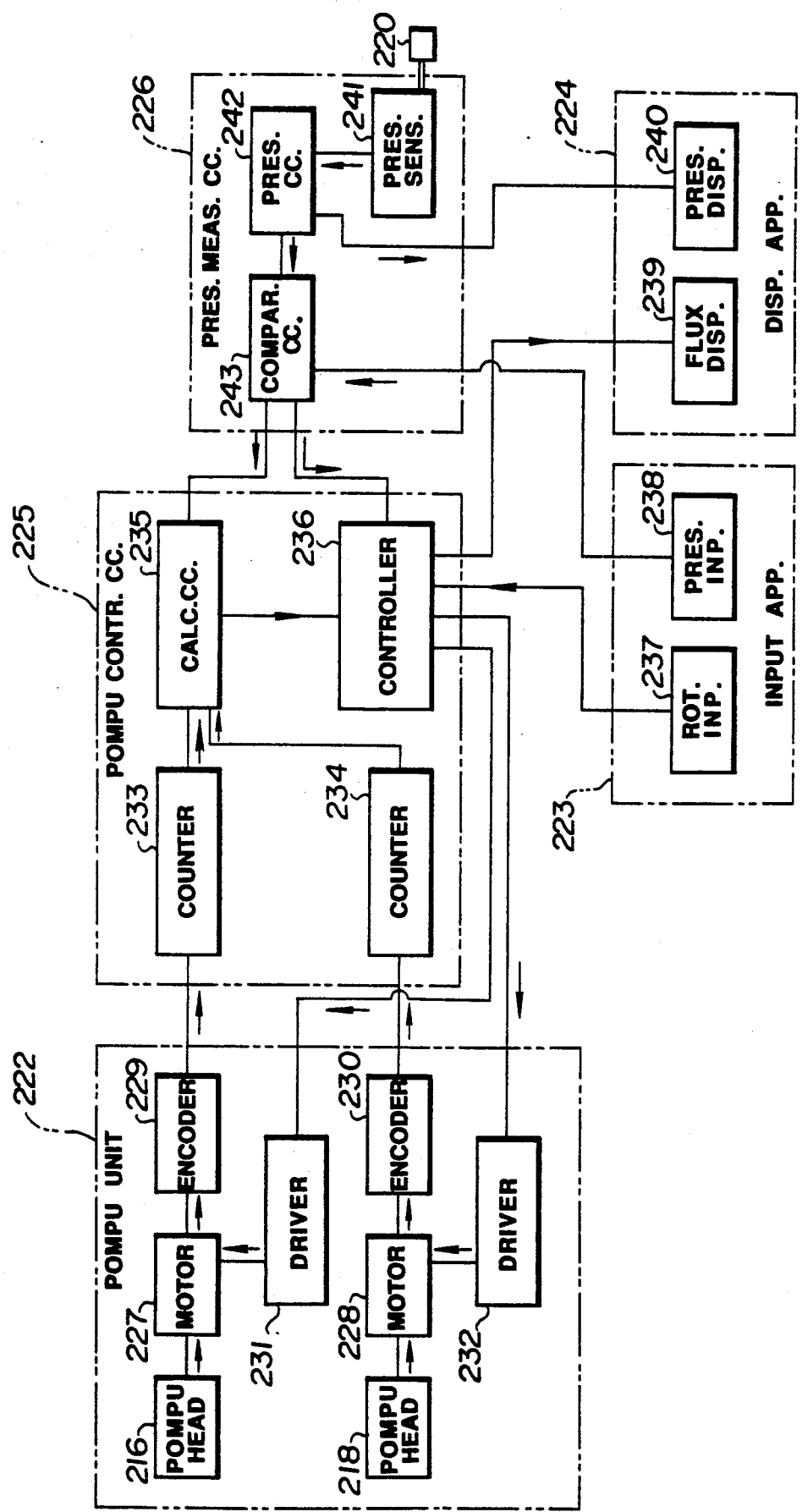

FIG. 26 shows a principal portion of the litholysis apparatus shown in FIG. 25.

The circuit unit 221 shown in FIG. 25 mainly comprises a pump control circuit 225 and a pressure measuring circuit 226. The pump unit 222 connected to the circuit unit 221 comprises sending and exhaust pump units 216, 216, electric motors 277, 288 for rotating the rotors 216b, 218b in the pump heads 216, 218, respectively, encoders 229, 230 for generating pulses used for displaying the rotation of the electric motors 227, 228, respectively, and drivers 231, 232 for supplying electric energy to the electric motors 227, 228, respectively.

The pump control circuit 225 comprises counters 233, 234 for counting the pulse signals output from the encoders 229, 230, respectively, an arithmetic circuit 235 for performing predetermined calculations on the basis of the output from the counters 233, 234, and a controller 236 for receiving a signal from the rotation input apparatus 237 in the input apparatus 223, sending a motor rotation control signal to the drivers 231, 232 and outputting a signal indicating a flux to the flux display apparatus 239 in the display apparatus 224.

The pressure measuring circuit 226 comprises the pressure sensor 241 connected to the pressure duct 215 (refer to FIG. 25) through the connector 220, a pressure circuit 242 for amplifying the output from the sensor 241 and measuring it, and a comparison circuit 243 to which a signal output from the pressure circuit 242 and a signal indicating the set pressure output from the pressure input apparatus 238 in the input apparatus 223 are input. The comparison circuit 243 performs a comparison operation between both signals and outputs a signal indicating the result of the operation to the arithmetic circuit 235 and the controller 236. The pressure display apparatus 240 is connected to the output terminal of the pressure circuit 242 so that the pressure detected by the pressure sensor 241, i.e., the pressure in a portion of litholysis treatment, for example, the gallbladder, is displayed on the display apparatus 240.

The operation of the litholysis treatment apparatus 201 configured as described above is the following:

The end of the catheter 207 is first introduced into the gallbladder 204 along the inner hole of the external sheath 206 with which the abnominal wall is punctured and which is buried in the gallbladder 204, the external sheath 206 being closely fixed to the catheter 207 by the connector 208. The three ducts, which are branches at the rest end of the catheter 207, are then connected to the liquid-sending tube 211, the exhaust tube 213 and the pressure duct 215 through the cocks 210, 212, 214, respectively. The duct of the pressure sensor 241 provided in the circuit unit 221 communicates with the pressure duct 215 through the connector 220. At this time, when the rotation input apparatus 237 is operated, the controller 236 drives the driver 232 to rotate the motor 228. As a result, the bile in the gallbladder 204 is passed through the exhaust duct of the catheter 207 and the exhaust tube 213 and discharged to the exhaust bottle 219. At this time, when the pressure circuit detects a signal of the pressure sensor 241 indicating the sate wherein the bile is completely discharged, and the pressure in the gallbladder is 1 atom (atmospheric pressure) or less, the comparison circuit 243 is operated so as to drive the controller 236 to stop the motor 228 through the driver 232. When the pressure input apparatus 238 is then operated so that the pressure in the gallbladder 204 is set to a value over 1 atom, the controller 236 drives the driver 231 to rotate the motor 227 so that the lithotriptic received in the liquid bottle 217 is introduced into the gallbladder 204 through the liquid-sending tube 211 and the liquid-sending duct of the catheter 207. When the gallbladder is filled with the lithotriptic and when the pressure in the gallbladder 204 exceeds 1 atom, the pressure is detected by the sensor 241 through the circuit 242, and the controller 236 stops the rotation of the motor 227 in response to the signal output from the comparison circuit 243. The number of revolutions of the motor 227 from the start to the stop is detected by the encoder 229 connected to the rotational shaft of the motor, counted by the counter 233 and then input to the arithmetic circuit 235. If the diameter of the liquid-sending duct is constant, the allowable maximum quantity of the lithotriptic sent to the gallbladder 204 is determined by the number of revolutions. If the circulation of the medical fluid is continued to the maximum quantity, there is a danger of creating a leak of the medical fluid to organs other than the gallbladder 204 owing to a variation in the pressure in the gallbladder 204. A number of revolutions of the pump, which produces a certain percentage, for example 80%, of the maximum quantity, is therefore determined by the arithmetic circuit 235. The controller 236 rotates the motor 228 and stops at 80% of the maximum. In this embodiment, although the standard quantity is 80% of the maximum, any percentage can be set by changing the value input to the input apparatus 223. When the standard quantity is determined, the liquid-sending motor 227 and the exhaust motor 228 are continuously rotated at the same revolution so as to continuously send and discharge the lithotriptic. Alternately, a cycle, which comprises the step of storing the lithotriptic in the gallbladder 204 for a predetermined time, introducing and sucking the standard quantity of lithotriptic and then storing the lithotriptic, may be repeated.

The pressure and the quantity of the medical fluid in the gallbladder 204 are displayed on the pressure display apparatus 240 and the flux display apparatus 239, respectively, so that the operator can recognize the conditions. There is the possibility that the bile enters the gallbladder 204 and increases the quantity of the liquid in the gallbladder 204 during the repetition of sending and suction of the lithotriptic. However, this can be avoided by repeating the operation of determining the standard quantity of the lithotriptic at certain intervals. Namely, the gallbladder is emptied by completely sucking the bile and the lithotriptic in the gallbladder, and the standard quantity is then determined by the quantity of the lithotriptic sent until the pressure in the gallbladder becomes a predetermined value, for example, 1 atom. Since the time the set quantity of lithotriptic in the liquid bottle 217 is completely sent is determined by the number of revolutions of the liquid-sending motor 227, at this time, the controller 236 stops the liquid-sending motor 227, and the exhaust motor 228 only is rotated so as to discharge the liquid in the gallbladder. At the time the liquid in the gallbladder is completely discharged, one cycle of treatment is completed.

This embodiment permits an appropriate quantity of lithotriptic to be sent and discharged by a simple operation and thus has a safe and effective treatment effect.

A ninth embodiment of the present invention is described below with reference to FIGS. 27 and 28.

Although the configuration of the ninth embodiment is substantially the same as that of the eighth embodiment, they are different from each other in the mechanism of detecting the flow rate. The same components as those in the eighth embodiment are denoted by the same reference numerals and are not described below for the sake of simplification.

Figure 27:
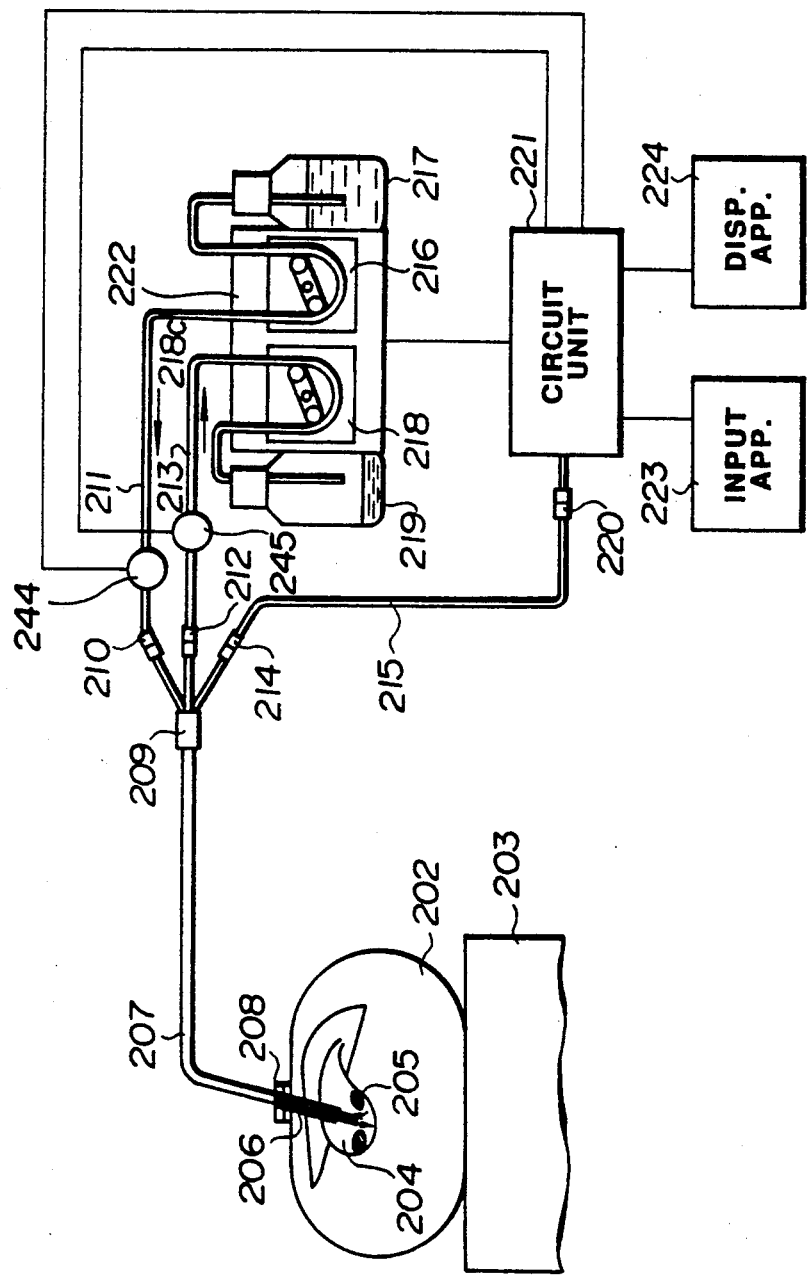

As shown in FIG. 27, a sending flow sensor 244 is provided at an intermediate position of a liquid-sending tube 211 for the purpose of measuring the flow of the lithotriptic flowing through the tube, and an exhaust flow sensor 245 is provided in an exhaust tube 213 for the purpose of measuring the flow of the discharge of the lithotriptic from the gallbladder 204.

Figure 28:
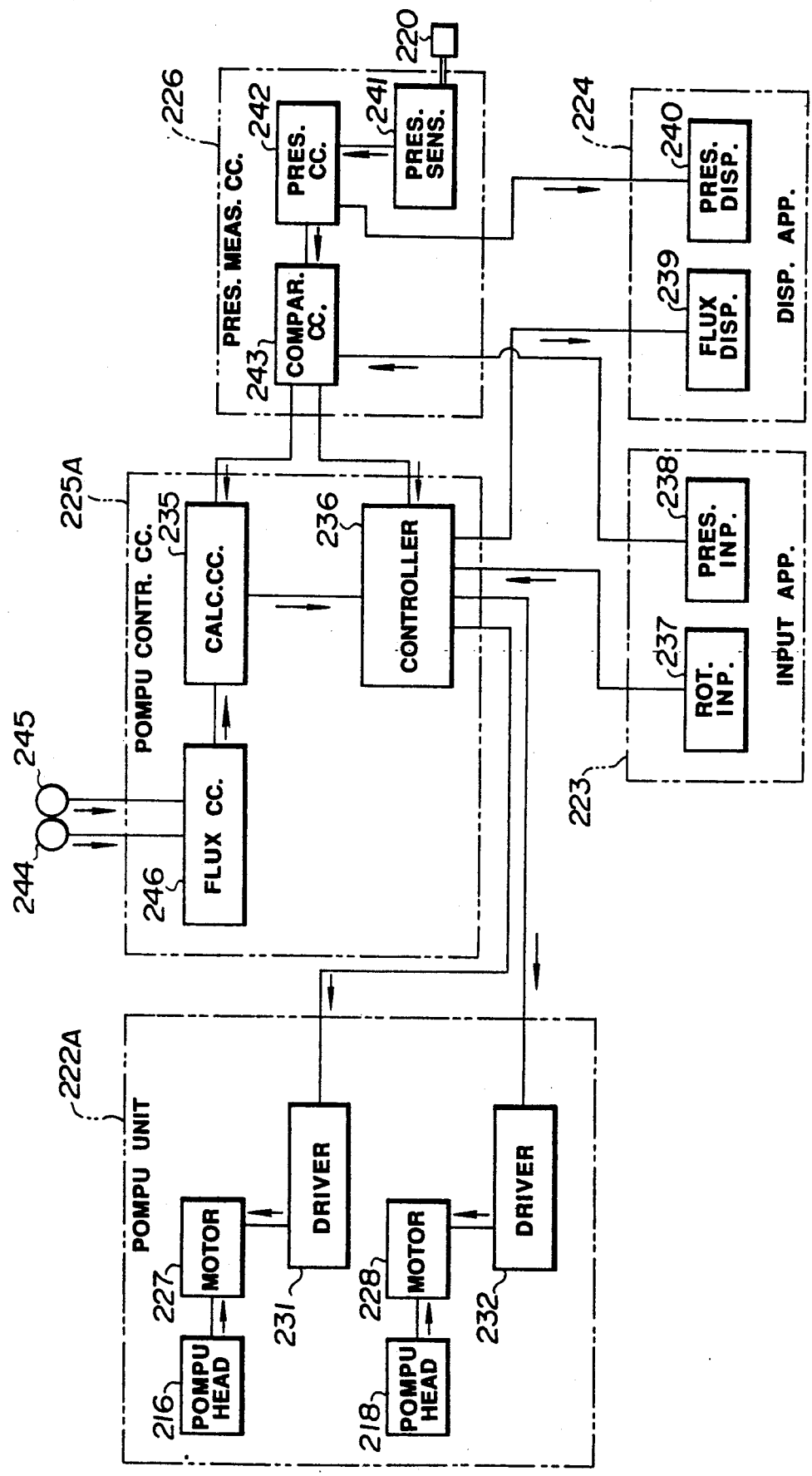

As shown in FIG. 28, the sensors 244, 245 are connected to a flow circuit 246 provided in a pump control circuit 225A so that a signal of detection by the sensors 244, 245 is electrically processed. Namely, although the flow is calculated on the basis of the number of revolutions of each motor 227, 228, which is detected by the encoders 227, 228, respectively, in the eighth embodiment, the flow through the tube is directly measured in the ninth embodiment.

The operation of the ninth embodiment configured as described above is described below. Since the mechanism of driving the motors and the mechanism of detecting the pressure in the gallbladder in the ninth embodiment are the same as those in the eighth embodiment, only the function to send and discharge the medical fluid on the basis of the flow rates of the medical fluid detected by each of the flow sensors is described below. When the bile in the gallbladder 204 is first discharged in a state arranged as shown in FIG. 27, the rotation of the motor 227 is started by the operation of the pressure input apparatus 238 so that the lithotriptic is charged in the gallbladder 204, and is then stopped when the pressure exceeds 1 atom. The flow sent from the start of the rotation of the motor 227 to the end thereof is detected by the flow sensor 244, and a signal output from the flow sensor 244 is detected by the flow circuit 246. The flux detected is input to the arithmetic circuit 235. In the arithmetic circuit 235, the maximum quantity sent into the gallbladder 204 is calculated on the basis of the detected flux. For example, 80% of the maximum quantity is considered as a standard quantity, and only the motor 228 is rotated so as to discharge the lithotriptic and then stopped when the quantity of the remaining lithotriptic in the gallbladder 204 reaches the standard quantity on the basis of the signal output from the flux sensor 245. Although the standard quantity is 80% of the maximum quantity in this embodiment, any percentage can be set as a standard quantity in correspondence with the value set in the input apparatus 228. After the quantity of the liquid in the gallbladder 204 has reached to the standard quantity, the lithotriptic may be continuously send and discharged by driving the liquid-sending motor 227 and the exhaust motor 228 at the same number of revolutions. Alternatively, a cycle comprising the steps of storing the lithotriptic sent into the gallbladder for a predetermined time, then discharging it and again sending it may be repeated. In the process of sending and discharging the lithotriptic, the sending quantity and the discharging quantity are constantly monitored by the flux sensors 244, 245 so that, when the discharging quantity is decreased owing to the clogging of the exhaust duct with the fragments of the calculus recovered, the number of revolutions of the sending motor 227 is temporarily decreased by the controller 236. Namely, the sending quantity and the exhaust quantity are constantly controlled so as to be the same, and the sending quantity is caused to follow the discharging quantity so that the sending motor 227 is stopped when the exhaust duct is completely closed. The actions carried out to the end of the treatment are the same as in the eighth embodiment.

As described above, in this embodiment, since the sending and discharging quantities are monitored by using the flux sensors, treatment can be further completely made without the lithotriptic being excessively sent owing to the clogging of a duct.

Figure 29:
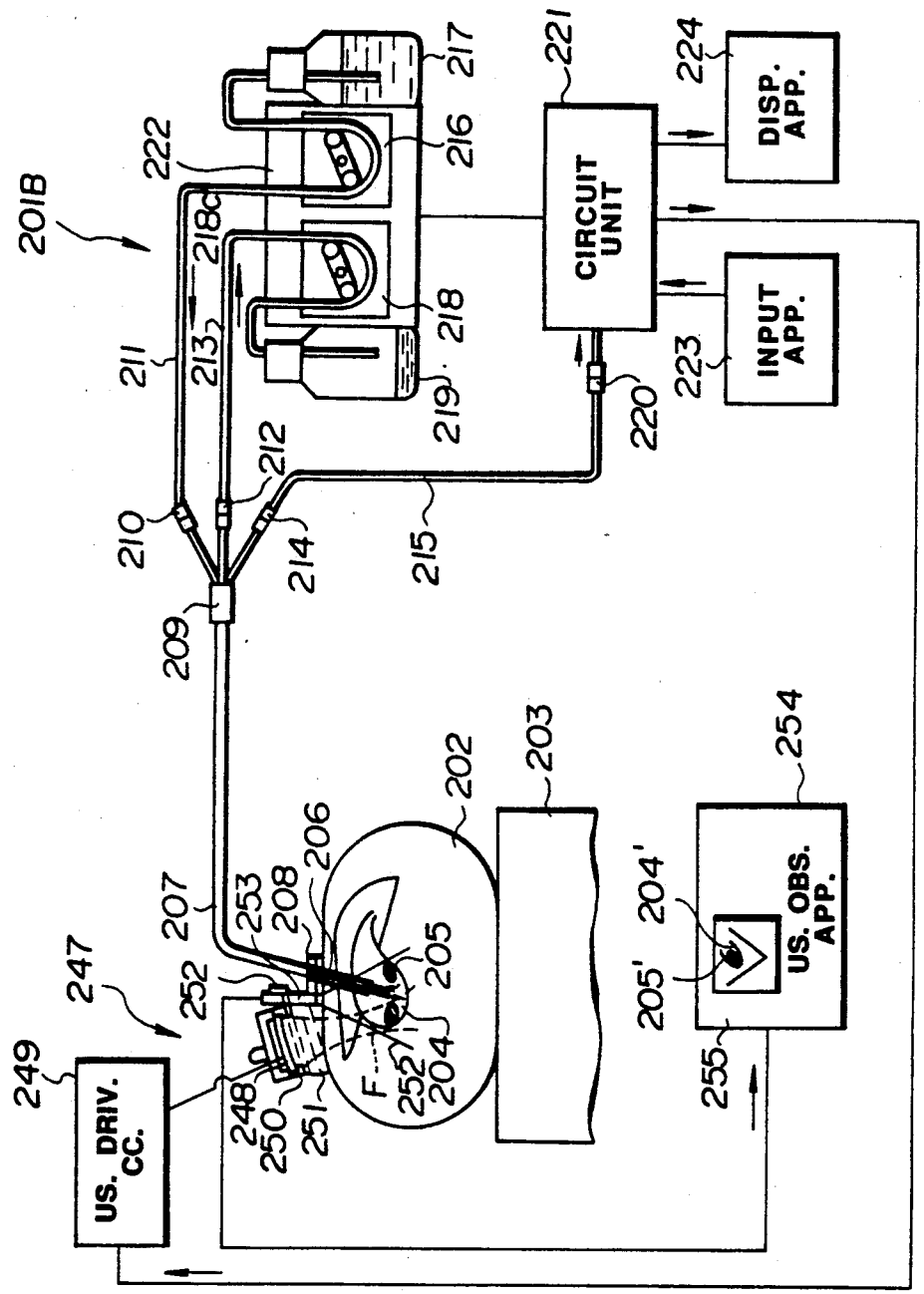

A litholysis treatment apparatus 201B of a tenth embodiment of the present invention is described below with reference to FIG. 29.

The tenth embodiment is the same as the eighth embodiment with the exception that an external ultrasonic generator 247 is provided for further promoting litholysis. As is generally known, the external ultrasonic generator 247 has a single or plurality of ultrasonic piezoelectric transducers 248 so that the ultrasonic wave generated from the ultrasonic piezoelectric transducers 248 is applied to a the region F in the human body 202 when being driven by an ultrasonic driving circuit 249. The ultrasonic piezoelectric transducers 248 are fixed on the external ultrasonic generator 247 by means of a ring-shaped transducer fixing member 250, with a water bag 251 made of a soft resin or the like between the oscillators 248 and the human body 202. The water bag 251 is filled with an ultrasonic transfer liquid such as water. An ultrasonic probe holding tool 252 is formed in a portion of the body of the external ultrasonic generator 247 so as to outwardly extrude therefrom. An ultrasonic probe 253 is detachably held by this ultrasonic probe holding tool 252 in such a manner that the axis of the sectoral observation range 252 agrees with the axis of the ultrasonic irradiation region of the external ultrasonic generator 247 in the region F in the human body 202. The ultrasonic probe 253 is connected to the ultrasonic observation apparatus 254 so that the observation image in the sectoral scanning region 252 including the gallbladder 204 in the human body 202 is displayed on the monitor 255 of the ultrasonic observation apparatus 254. The ultrasonic driving circuit 249 is also connected to the controller (not shown) in the circuit unit 221.

The operation of the litholysis treatment apparatus 201B of the tenth embodiment configured as described above is the following:

Since a single operation of sending and discharging the lithotriptic in the tenth embodiment is the same as in the eighth embodiment, the operation of the external ultrasonic generator 247 and the operation of sending and discharging the lithotriptic related thereto are described below. The external ultrasonic generator 247 is first disposed opposite to the human body 202, with the water bag 251 therebetween. The ultrasonic probe 253 is brought into contact with the human body 202 so as to observe the interior of the human body 202. During this operation, the external ultrasonic generator 247 is moved or fixed by the operator (not shown) manually or using a simple mounting apparatus. This operation causes the display of the ultrasono-tomographic image of the interior, i.e., the gallbladder 204' and the calculus 1205', of the human body 202 on the monitor 255. The external sheath 206 may be inserted into the gallbladder 204 from the abdominal wall of the human body 202 under the guide of the ultrasonic image or previously disposed. The end of the catheter 207 is then inserted along the inner hole of the external sheath 206 and is closely fixed to the external sheath 206 by the connector 208.

The input apparatus 223 is then operated in the same way as in the eighth embodiment so as to send and discharge the lithotriptic. At the same time, the controller (not shown) in the circuit unit 221 drives the ultrasonic driving circuit 249 to apply an ultrasonic wave to a portion near the calculus 205. The irradiation of an ultrasonic wave is repeated in a predetermined cycle for the purpose of promoting the litholysis. At this time, the timing of the sending and discharge of the lithotriptic and the timing of irradiation of an ultrasonic wave can be previously set in the input apparatus 223 so that they are automatically controlled by the controller (not shown).

A description will now be given of a pattern of the sending and discharge of the lithotriptic and the irradiation of an ultrasonic wave with reference to FIG. 30.

Figures 30A, 30B:
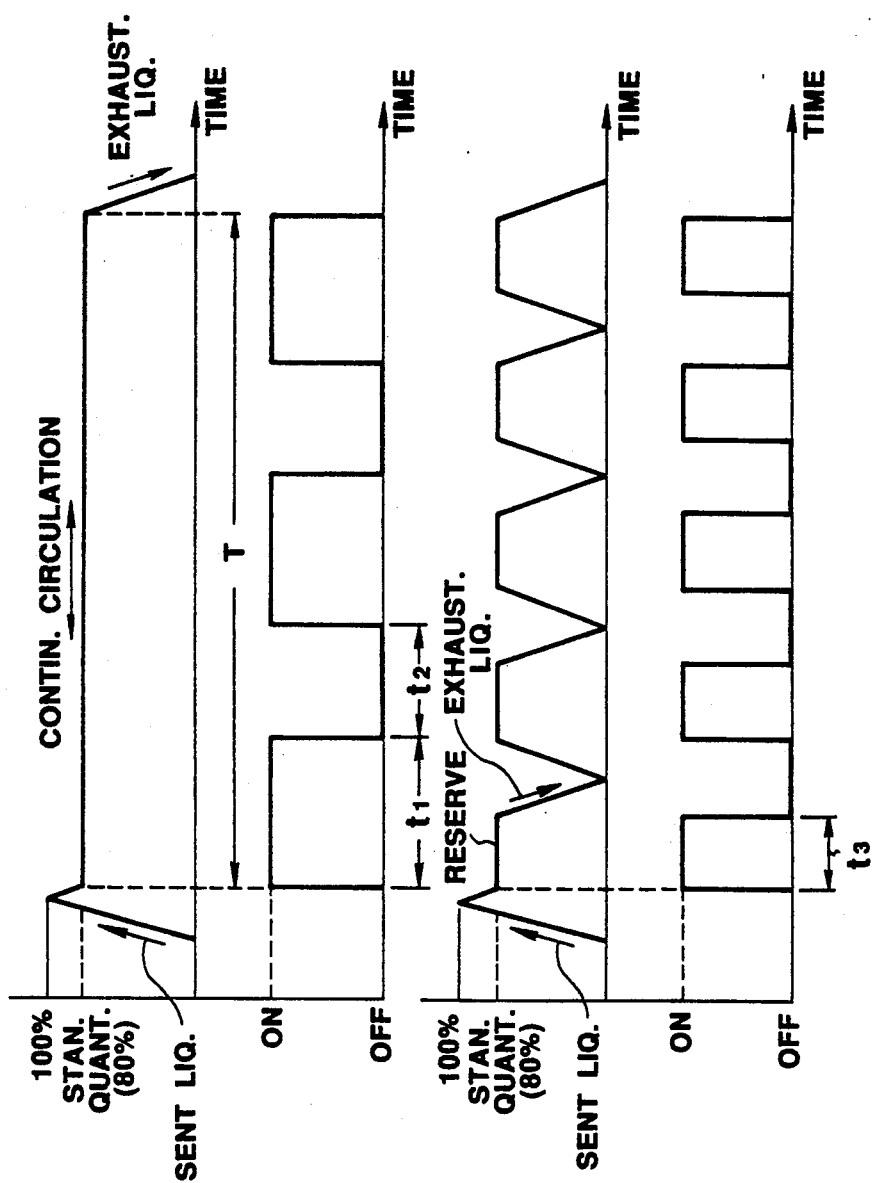
FIGS. 30a–b are explanatory views of the operation.

In both the upper and lower drawings in FIG. 30, the time is shown on the abscissa. The quantity of the lithotriptic in the gallbladder is shown on the ordinate in the upper drawing, and the ON and OFF state of ultrasonic driving is shown on the ordinate in the lower drawing. For example, in FIG. 30a, the irradiation of an ultrasonic wave is started when the quantity of the lithotriptic in the gallbladder is the standard quantity. The sending pump head 216 and the exhaust pump head 218 are driven the same times so as to be continuously and simultaneously rotated for a time T (for example, 1 hour) until the lithotriptic in the liquid bottle 217 is completely used. During this time, a cycle comprising the steps of applying an ultrasonic wave for a time $t_1$ (for example, 3 minutes) and then stopping it for a time $t_2$ (for example, 1 minute) is repeated. The times $t_1$ and $t_2$ can be previously freely set in the input apparatus 223. In FIG. 30b, an ultrasonic wave is applied only for a time $t_3$ (for example 1 minute) the standard quantity of the lithotriptic is stored in the gallbladder. In FIG. 30b, the sending and discharge of the lithotriptic are not made simultaneously, but a cycle comprising sending the liquid, storing it for a given time and discharging it is repeated. In this case, the time $t_3$ for storing the lithotriptic can be previously and freely set.

As described above, in this embodiment, since the ultrasonic wave is applied from the outside of the human body, it is possible to further promote the litholysis and rapidly and effectively make treatment.

As shown in FIG. 30, in the tenth embodiment, although the flow rate of sending (irrigation) is set to a value substantially the same as that of discharge (suction), the flow rate of sending may be higher than that of discharge, as shown in an explanatory view of the operation of a modification in FIG. 31. This modification employs the driving system shown in FIG. 26 so that the irrigation speed is controlled to be higher than the suction speed.

Figures 31A, 31B, 31C:
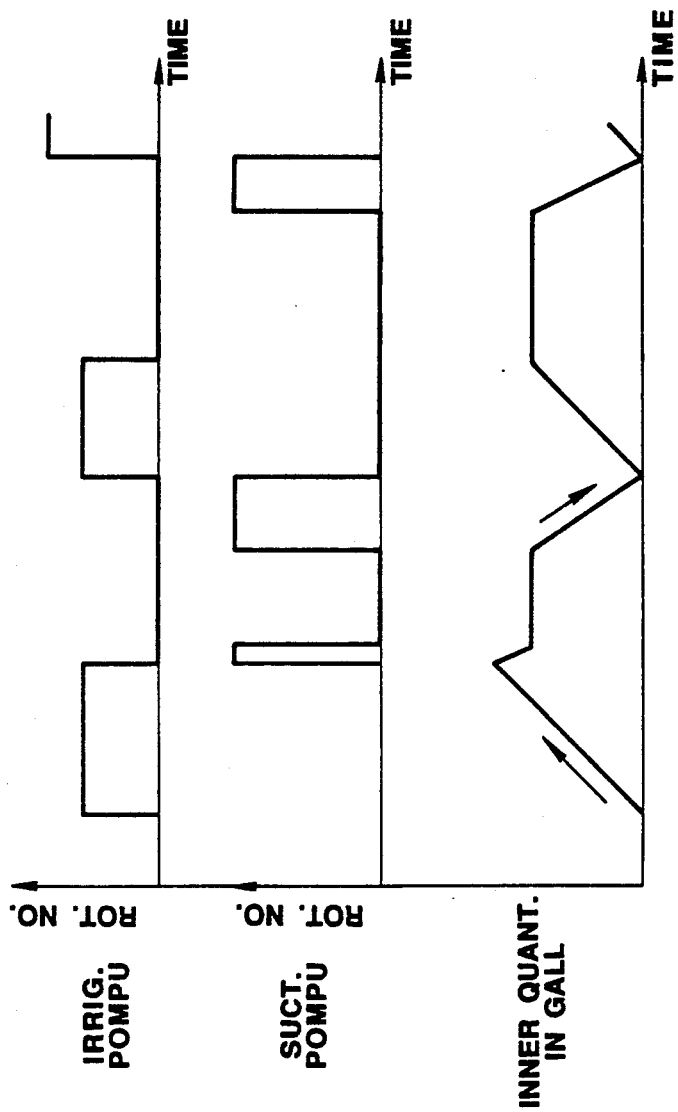
FIGS. 31a–c are explanatory views of the operation of a modification of the eighth embodiment.

In FIGS. 31a, 31b, the number of revolutions of each of the pumps is shown on the ordinate, and, in FIG. 31c, the quantity of the lithotriptic in the gallbladder is shown on the ordinate.

The number of revolutions of the irrigation pump 216 is input to a rotation input apparatus 237 before the start of treatment, and the number of revolutions of the suction pump 218, which is certain times (2 times) that of the irrigation pump 216, is then input. When the treatment is started, the irrigation pump 216 is first driven with the set number of revolutions and then stopped when the quantity of the lithotriptic reaches the maximum quantity. The suction pump 218 is then rotated and stopped when the quantity of the lithotriptic becomes the standard quantity (for example, 80% of the maximum quantity). The lithotriptic is then stored in the gallbladder for a predetermined time (in which an ultrasonic wave may be applied), and the suction pump 218 is again rotated and stopped when the quantity of the liquid in the gallbladder becomes zero. The irrigation time taken until the quantity of the liquid reaches the standard quantity and the time taken to complete the suction are calculated by the arithmetic circuit 235 on the basis of the output from the encoder 229. The repetition times of irrigation and suction are controlled on the basis of the numbers of revolutions and the times calculated so that irrigation and suction are repeated predetermined times and then stopped.

In this modification, since the suction speed of the lithotriptic is automatically set to a value higher than the irrigation speed, the lithotriptic does not leak, and the pressure in the gallbladder can be rapidly reduced even if it is increased. In addition, since the suction speed is higher than the irrigation speed, treatment can be safely made, without producing clogging the suction duct with fragments of the calculus, as compared with conventional apparatuses.

An eleventh embodiment of the present invention is described below.

The overall configuration of this embodiment is the same as that of the apparatus 201 shown in FIG. 25 with the exception that a control apparatus 324 is used in place of the circuit unit 221, the input apparatus 223 and the display apparatus 224. In addition, an irrigation pump 322 and a suction pump 323, which are separate units, are used as the pump 222 shown in FIG. 25, and a pressure detecting means 321 is connected to the connector 220, the output from the detecting means 321 being input to a control means 324.

The control means 324 shown in FIG. 32 comprises a differential amplifier 330 for differentially amplifying the pressure signal output from the pressure detecting means 321, a gain adjusting means 331 for adjusting the amplification factor of the differential amplifier 330, an offset adjusting means 332 for setting the pressure offset value for the pressure detecting means 321 in the differential amplifier 330, an integrator 333 for removing any influence on the subsequent step even when the signal output from the differential amplifier 330 varies for a predetermined short time (momentarily), a time constant adjusting means 334 for setting a predetermined time for the integrator 333, a standard voltage source 335 for generating a voltage serving as an upper limit standard value of the pressure detected by the pressure detecting means 321, an output adjusting means 336 for setting the voltage value of the standard voltage source 335, a standard voltage source 337 for generating a voltage serving as a standard value of a suction start pressure, an output adjusting means 338 for setting the voltage value of the standard voltage source 337, a differential amplifier 339 for differentially amplifying the signal output from the integrator 333 and the signal (standard voltage) output from the standard voltage source 335, a gain adjusting means 340 for adjusting the amplification factor of the differential amplifier 339, an offset adjusting means 341 for setting an outset value of the signal output from the differential amplifier 339, a limiter circuit 342 for limiting the signal output from the differential amplifier 339 so that the signal does not exceed a predetermined voltage value, a switch means 343 for deciding whether or not the signal output from the limiter circuit 342 is output to the irrigation pump 322, a differential amplifier 344 for differentially amplifying the signals output from the standard voltage sources 335, 337 and outputting a signal used for controlling the number of revolutions of the suction pump 323, a gain adjusting means 345 for adjusting the amplification factor of the differential amplifier 344, a limiter circuit 346 for limiting the signal output from the integrator 333 to a voltage value lower than a predetermined value, a hysteresis comparator 347 for comparing the signal output from the standard voltage source 337 with the signal output from the integrator 333 through the limiter circuit 346 on the basis of the predetermined hysteresis characteristics and controlling the switch control means 348 described below, the switch control means for controlling the start and stop of the suction pump 323, a logical circuit 349 controlling the switch means 343 and 348 on the basis of the signals from the limiter circuit 346 and the end input circuit 350 described below, the end input means 349 for controlling so as to end treatment, a pressure display means 351 for displaying the pressure detected by the pressure detecting means 321 and an offset display means 352 serving as a display means for adjusting the offset adjusting means 332.

In the differential amplifier 330, the input terminal is connected to the output terminal of the pressure adjusting means 321, the offset adjusting terminal is connected to the offset adjusting means, and the amplification factor adjusting terminal is connected to the gain adjusting means 331.

In the integrator 33, the input terminal is connected to the output terminal of the differential amplifier 330, and the time constant adjusting terminal is connected to the time constant adjusting means 334.

The output adjusting means 336 is connected to the input terminal of the standard voltage source 335, and the output adjusting means 338 is connected to the input terminal of the standard voltage source 337.

In the differential amplifier 339, the first input terminal is connected to the output terminal of the integrator 333, the second input terminal is connected to the output terminal of the standard voltage source 335, the amplification factor adjusting terminal is connected to the gain adjusting means 340, and the offset adjusting terminal is connected to the offset adjusting means 341.

The input terminal of the limiter circuit 342 is connected to the output terminal of the differential amplifier 339.

In the switch means 343, the input terminal is connected to the output terminal of the limiter circuit 342, the control terminal is connected to the first output terminal of the logical circuit 349, and the output terminal is connected to the revolution control terminal of the irrigation pump 322.

In the differential amplifier 344, the first input terminal is connected to the output terminal of the standard voltage source 335, the second input terminal is connected to the output terminal of the standard voltage source 337, and the output terminal is connected to the revolution control terminal of the suction pump 323.

The input terminal of the limiter circuit 346 is connected to the output terminal of the integrator 333.

In the hysteresis comparator 347, the first input terminal is connected to the output terminal of the standard voltage source 337, and the second input terminal is connected to the input terminal of the limiter circuit 346.

In the switch means 348, the input terminal is connected to the output terminal of the hysteresis comparator 347, the control terminal is connected to the second output terminal of the logical circuit 349, and the output terminal is connected to the on/off control terminal of the suction pump 323.

In the logical circuit 349, the first input terminal is connected to the output terminal of the limiter circuit 346, and the second input terminal is connected to the end input means 350.

The input terminals of the pressure display means 351 and of the offset display means 352 are connected to the output terminal of the limiter circuit 346.

The differential amplifier 330 performs offset adjustment of the pressure signal from the pressure detecting means 321 using the offset signal output from the offset adjusting means 332 so as to remove the error components which are contained in the pressure signal owing to the positional relation between the pressure detecting means 321 and the gallbladder and atmospheric pressure. The differential amplifier 330 also performs differential amplification with the amplification factor which is set by the gain adjusting means 331 so as to remove noise components which are contained in the pressure signal. The offset adjustment is effected by the offset adjusting means 332, for example, while the operating observing the display on the offset display means 352.

The integrator 333 integrates the signal output from the differential amplifier 330 with the time constant set by the time constant adjusting means 334 so as to prevent any momentary variation in the signal level which is generated, for example, due to a slight shock of the human body 202, from being transmitted to the subsequent stage.

The differential amplifier 339 performs offset adjustment of the deviation in zero potential, which is caused by the differential amplification, on the basis of the offset signal output from the offset adjusting means 341 and differential amplification of the signal output from the integrator 333 and the voltage output from the standard voltage source 335 with the amplification factor which is set by the gain adjusting means 340. The voltage output from the standard voltage source 335 is controlled by the output adjusting means 336 and serves as a signal indicating the upper limit pressure.

The limiter circuit 342 limits the signal output from the differential amplifier 339 to a value which is smaller than the predetermined upper limit.

The switch means 343 decides whether or not the signal output from the limiter circuit 342 is output as the revolution control signal to the irrigation pump 322, on the basis of the control signal output from the logical circuit 349.

The differential amplifier 344 performs differential amplification of the voltage output from the standard voltage source 335 and the voltage output from the standard source 337 with the amplification factor which is set by the gain adjusting means 345. The voltage output from the standard voltage source 337 is controlled by the output adjusting means 338 and serves as a signal indicating the suction start pressure. The signal output from the differential amplifier 344 is output as the revolution control signal for the suction pump 323.

The limiter circuit 346 limits the the signal output from the integrator 333 to a signal within a range which causes no wrong operation of the circuit (means) in the subsequent stage.

The hysteresis comparator 347 compares the voltage output from the standard voltage source 337 with the signal output from the limiter circuit 346 and outputs the results of the comparison on the basis of the predetermined hysteresis characteristics.

The switch means 348 decides whether or not the signal output from the hysteresis comparator 347 is output as the on/off control signal for the suction pump 323 on the basis of the control signal output from the logical circuit 349.

The logical circuit 349 controls the switch means 348 on the basis of the signal output from the limiter circuit 346 so that the switch means 348 outputs the signal output from the hysteresis comparator 347 as the operational signal to the suction pump 323 when the pressure in the gallbladder 204 reaches the suction start pressure (target pressure). When the pressure in the gallbladder reaches the suction stop pressure, the switch means 348 is controlled so as not to output the signal output from the hysteresis comparator 347 as the operational signal for the suction pump 323. When the pressure in the gallbladder 204 abnormally increases, the switch means 343 is controlled so as not to output the signal output from the limiter circuit 342 as the revolution control signal for the suction pump 322, as well as being controlled so as not to output the signal output from the limiter circuit 342 as the revolution control signal for the irrigation pump 322 on the basis of the end signal input from the end input means 350.

The end input means comprises, for example, a switch, which, when it is operated by the operator, outputs an end signal for operating each of the units in the litholysis treatment apparatus 1 so as to end the treatment.

The pressure display means 351 displays the pressure in the gallbladder 204, which is detected by the pressure detecting means 321 on the basis of the signal output from the limiter circuit 346.

The offset display means 352 displays the pressure in the gallbladder 204, which is detected by the pressure detecting means 321, on the basis of the signal output from the limiter circuit 346 so that the pressure can be easily adjusted by the operator using the offset adjusting means 332.

The function of the litholysis treatment apparatus configured as described above is described below.

The pressure of the medical fluid 217a and the like in the gallbladder 204 is transmitted to the pressure detecting means 321 through the catheter 207, the connector 209, the cock 214, the pressure duct 215 and the connector 220, converted into an electrical signal by the pressure detecting means and then input as a pressure signal to the control means 324.

As shown in FIG. 32, the control means 324 performs offset adjustment of the pressure signal, which is the small signal output from the pressure detecting means 321, by the differential amplifier 330, as well as differential amplification for removing noise components and the like by the differential amplifier 330 so that the pressure signal is a signal in a predetermined level.

The signal output from the differential amplifier 330 is input to the first input terminal of the differential amplifier 339 after momentary variation in the signal level has been absorbed by the integrator 333.

The standard voltage, which indicates the upper limit pressure and which is output from the standard voltage source 335, is input to the second input terminal of the differential amplifier 339. The differential amplifier 339 outputs a signal corresponding to a difference between the pressure signal, which is input to the first input terminal and which is subjected to treatment in the differential amplifier 330 and the integrator 333, and the standard voltage input to the second input terminal.

In this way, the signal output from the differential amplifier 339 is limited in its upper limit by the limiter circuit 342 and output to the irrigation pump 322 through the switch means 343. The limiter circuit 342 limits the upper limit of the irrigation speed (pressure) of the medical fluid 217a by the irrigation pump 322 so that the irritation speed (pressure) of the medical fluid 217a does no damage the gallbladder 204 and that the liquid 219a does not leak to portions other than the gallbladder.

In the differential amplifier 344, the standard voltage which is output from the standard voltage source 335 and which indicates the upper limit pressure, is input to the first input terminal, and the standard voltage, which is output from the standard voltage source 337 and which indicates the suction start pressure, is input to the second input terminal. The standard voltages input to the first and second input terminals are differentially amplified and output as the revolution control signal for the suction pump 323.

The hysteresis comparator 347 compares the signal in the signal level within the range which is limited by the limiter circuit 346 with the standard voltage which is output from the standard voltage source 337 and which indicates the suction start pressure, as well as outputting the result of the comparison as the on/off control signal provided with the predetermined hysteresis characteristics.

The suction stop pressure is set by the hysteresis characteristics.

The on/off control signal is output to the suction pump 348 through the switch means 323.

The pressure detected by the pressure detecting means 321 is displayed by the pressure display means. The pressure detected by the pressure detecting means 321 is also displayed by the offset display means 352 for the purpose of offset adjustment performed by the offset adjusting means 332 for the differential amplifier 330.

Figure 33A:
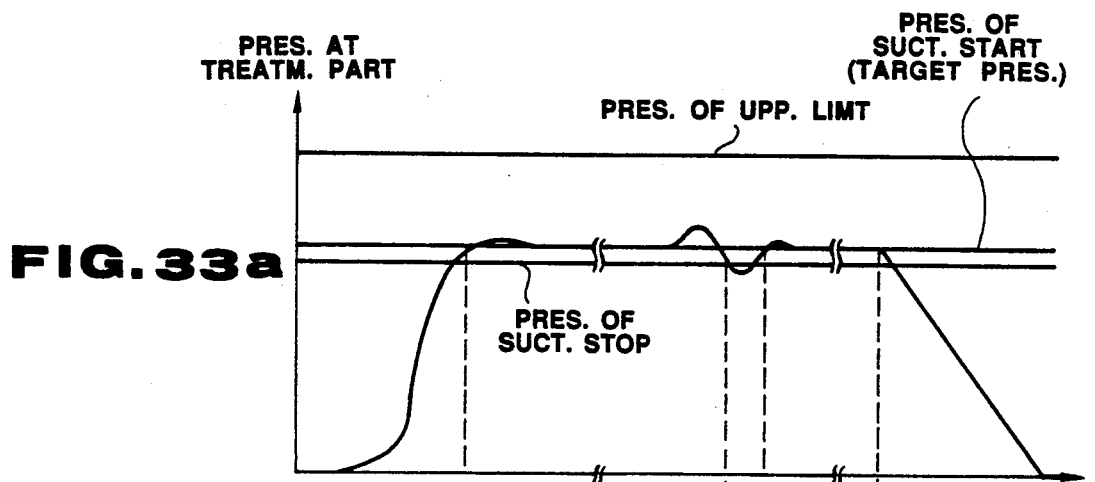
FIGS. 33a–c are timing charts provided for explaining the operation.
Figure 33B:
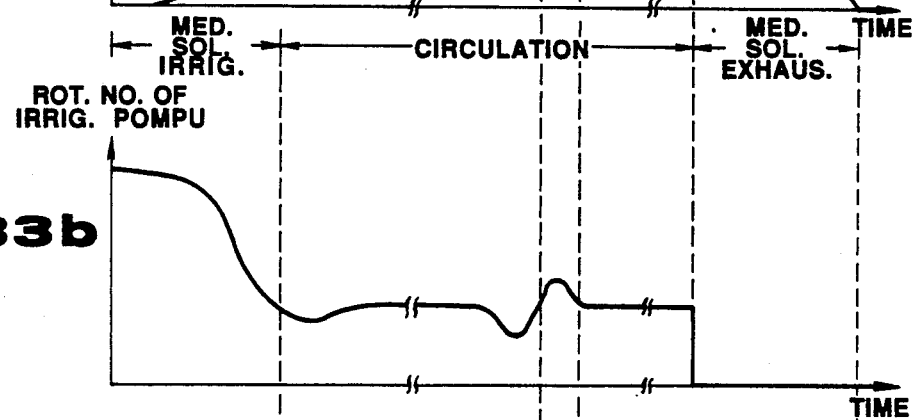
Figure 33C:
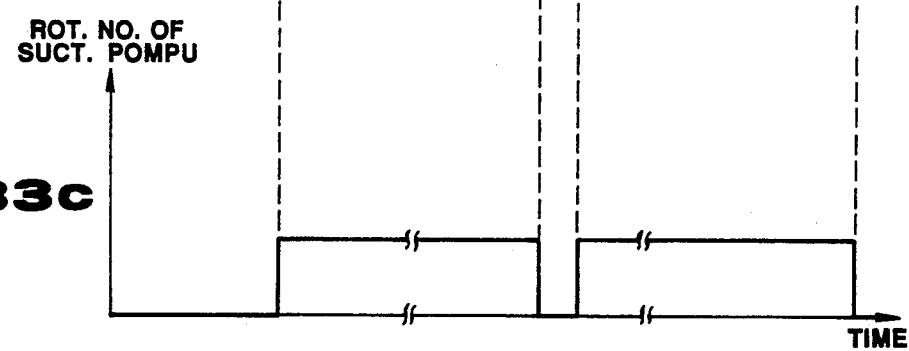

The above-described function is described below with reference to FIG. 33. FIG. 33a shows the pressure in the gallbladder 204, which is a treatment part, FIG. 33b shows the number of revolutions of the irrigation pump 322 and FIG. 33c shows the number of revolutions of the suction pump 323, in a time series.

When the cure (treatment) is started, the irrigation pump 322 is rotated at a high speed because of a great difference between the pressure in the gallbladder 204 and the upper limit pressure. The medical fluid 217a is therefore introduced in the gallbladder 204 at the upper limit pressure which produces no damage to the gallbladder 204. At this time, since the pressure in the gallbladder 204 does not reach the suction start pressure (target pressure), the suction pump 323 is not started.

When the pressure in the gallbladder 204 is gradually increased with the progress of the irrigation with the medical fluid 217a, the number of revolutions of the irrigation pump 322 is gradually decreased. The irrigation pressure is thus gradually decreased.

When the pressure in the gallbladder 204 reaches the suction start pressure (target pressure), the rotation of the suction pump 323 is started with the predetermined number of revolutions, as described above. Although the liquid 219a containing the medical fluid 217a is sucked at predetermined pressure, the medical fluid 217a is introduced at the same pressure so as to be circulated in the gallbladder 204, thereby promoting the dissolution of the calculus 205.

In order to prevent the pressure in the gallbladder 204 from reaching the upper limit pressure when the pressure in the gallbladder 204 is increased owing to a movement of the human body 202, the number of revolutions of the irrigation pump 322 is controlled so as to be further decreased.

When this causes a decrease in the pressure in the gallbladder 204, the number of revolutions of the irrigation pump 322 is increased. However, when the pressure in the gallbladder 204 is decreased to the suction stop pressure even by an increase in the number of revolutions of the irritation pump 322, the suction pump 323 is stopped, and only the irrigation pump 322 is operated. When this causes an increase in the pressure in the gallbladder 204 to the suction start pressure (target pressure), the suction pump 323 is again started.

For example, even when the suction tube 213 is clogged or when the suction pump is stopped, the number of revolutions of the irrigation pump 322 is further decrease so as to prevent the pressure in the gallbladder 205 from reaching the upper limit pressure when the pressure in the gallbladder 204 is increased. When the pressure in the gallbladder 204 is increased even by a decrease in the number of revolutions, the number of revolutions of the irrigation pump 322 becomes zero, i.e., the irrigation pump 322 is stopped.

When the end of the curing (treatment) is directed from the end input means 350, the irrigation pump 322 is stopped, the suction pump 323 is operated until the pressure in the gallbladder 204 becomes the pressure at the start of cure (treatment) and then stopped at the start pressure. The liquid 219a containing the medical fluid 219a is discharged from the gallbladder 204.

Namely, in this embodiment, the irrigation speed and the suction speed of the medical fluid can be controlled in correspondence with the pressure in a treatment part, for example, in the gallbladder 204, by a simple structure.

FIG. 34 is a block diagram which shows the configuration of a control means in a twelfth embodiment of the present invention. The configuration of a litholysis treatment apparatus in this embodiment is the same as that of the eleventh embodiment. In the drawing, the same units as those in the above embodiments are denoted by the same reference numerals and are not described below.

The control means of the embodiment is the same as the control means of the eleventh embodiment with the exception that an output switching means 323 for switching revolution control signals, a standard voltage source 354 for generating a second revolution control signal of the suction pump 323 and an output adjusting means 355 for adjusting the signal level of the standard voltage source 354 are provided.

In the output switching means 353, the first input terminal is connected to the output terminal of the differential amplifier 344 in the above-described eleventh embodiment, and the second input terminal is connected to the output terminal of the standard voltage source 354.

The output adjusting means 355 is connected to the input terminal of the standard voltage source 354.

The third output terminal of the logical circuit 349 in the above-described eleventh embodiment is connected to the control terminal of the output switching means 353.

The logical circuit 349 controls the output switching means 353 when the signal, which indicates the pressure in the gallbladder 204 and which is output from the limiter circuit 346, exceeds a predetermined value.

The output switching means 353 switches the signal output from the differential amplifier 344 to the signal output from the standard voltage source 354 on the basis of the control signal output from the logical circuit 354 and outputs the revolution control signal to the suction pump 323.

The signal output from the standard voltage source 354 is adjusted by the output adjusting means 355 so as to become a signal which increases the number of revolutions of the suction pump 323, as compared with the signal output from the differential amplifier 344.

The function of the control means configured as described above is described below.

When the comparator provided in the logical circuit 349 detects that the pressure in the gallbladder 204 is rapidly increased, the logical circuit 349 controls the output switching means 353 so that the switching means 353 outputs the signal output from the standard voltage source 354 as the revolution control signal for the suction pump 323.

This permits the suction pump 323 to be rotated at a speed which is set by the signal output from the standard voltage source 354 and which is higher than the normal speed and thus the pressure in the gallbladder 204 to be rapidly decreased.

Namely, the control means therefore has the effect of preventing the pressure of the liquid 219a from increasing to pressure which causes damage to a treatment part, for example, the gallbladder 204, and permitting a safe cure (treatment).

The other configuration and function are the same as those of the above-described embodiments.

FIG. 35 is a block diagram which shows the configuration of a control means in a thirteenth embodiment of the present invention. The configuration of a litholysis treatment apparatus is the same as that of the eleventh embodiment. The same units as those in the above embodiments are denoted by the same reference numerals and are not described below.

The control means of this embodiment is provided with a limiter circuit 356 in order to prevent the number of revolutions of the suction pump 323 from deviating from a predetermined range.

The input terminal of the integrator 333 is connected to the first input terminal of the differential amplifier 344 of the above-described eleventh embodiment, the input terminal of the limiter circuit 356 is connected to the output terminal of the differential amplifier 344, and the output terminal of the limiter circuit 356 is connected to the revolution control terminal of the suction pump 323.

The differential amplifier 344 outputs a signal corresponding to a difference between the signal, which is input to the first input terminal from the integrator 333, and the signal, which is input to the second input terminal from the standard voltage source 337.

The limiter circuit 356 limits the signal output from the differential amplifier 344 so that the number of revolutions of the suction pump 323 does not deviate from a predetermined range.

A description will now be given of the function of the control means configured as described above.

The standard voltage which indicates the suction start pressure is input to the second input terminal of the differential amplifier 344 from the standard voltage source 337. The differential amplifier 344 outputs a signal corresponding to a difference between the pressure signal which is input to the first input terminal and which is subjected to treatment in the differential amplifier 330 and the integrator 333, and the standard voltage which is input to the second input terminal.

The signal output from the differential amplifier 344 is limited by the limiter circuit 356 so that it does not deviate from a predetermined range and is then output as the revolution control signal for the suction pump 323.

In other words, the number of revolutions of the suction pump 323 is also changed in correspondence with the pressure in a treatment part, for example, in the gallbladder 204. The control means therefore has the effect of preventing a rapid change in the pressure in the gallbladder 204 and thus permits a cure (treatment) to be made, without producing any load on the gallbladder 204.

The other configuration, function and effect are the same as those in the above embodiments.

Figure 36:
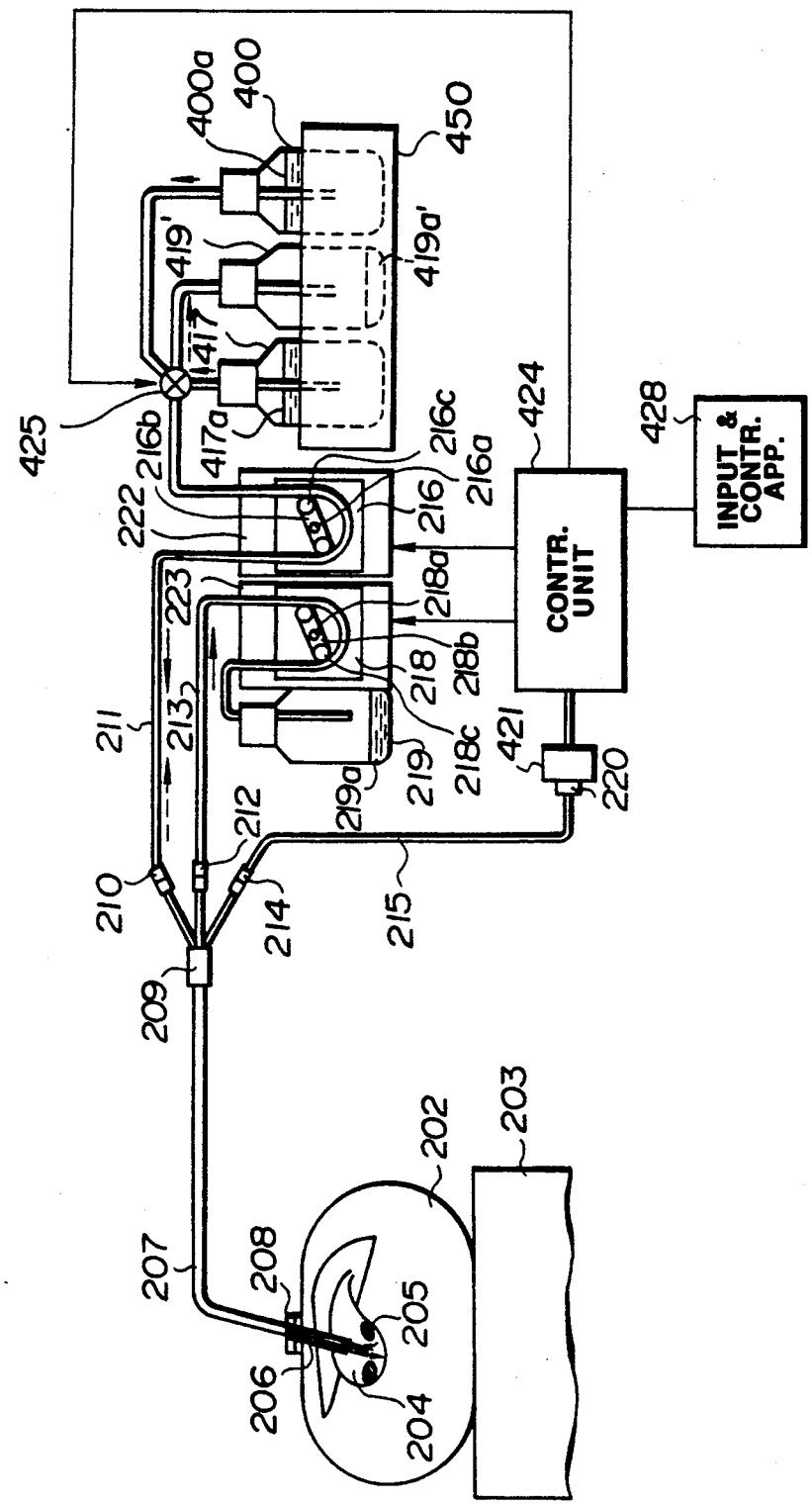

FIG. 36 shows the configuration of a circulation system in a fourteenth embodiment of the present invention.

In the apparatus in this embodiment, a pressure sensor 421 is connected to the connector 220 in the apparatus 201 shown in FIG. 25, and the output from the pressure sensor 421 is input to a control unit 424 provided in place of the circuit unit 221 in the apparatus 201, the control unit 422 being connected to an input/control apparatus 428.

As shown in FIG. 36, the control unit 424 controls the actions of the suction pump 218 and the irrigation pump 216. The irrigation pump 216 is a pump which preforms not only the irrigation action when being rotated in the normal direction but also the suction action when being rotated in the reverse direction.

The rear end (base end) of the irrigation tube 211, which is passed through the irrigation pump 216, is connected to an electromagnetic switching valve 425, branched through the valve 425 and connected to a liquid bottle 417 which contains a medical fluid 417a, a exhaust bottle 419 which contains a fluid 419a' such as the bile and the like sucked from the human body 202, and a liquid bottle 400 which contains a physiological saline 400a.

A suction tube 213 is connected to an exhaust bottle 219 for storing a medical fluid 219a which is sucked through the pump 218.

The switching of the valve 425 is controlled by the control unit 424. The configuration of the control unit 424 is shown in FIG. 37.

The configuration of the control unit 424 is the same as that shown in FIG. 15 with the exception that a change-over circuit 425' for switching only one valve 425 is provided. The change-over circuit 425' is connected to the input/control apparatus 428 through the I/O interface 44 and the bus 45.

As shown in FIG. 36, the three liquid bottles 417, 419', 400 are received in a thermostat 450 so as to be held at a given temperature, for example, a temperature substantially the same as the body temperature. The thermostat 450 has a heating means and a temperature control means (which are not shown in the drawing).

The temperature holing means can prevent a decrease in the litholysis ability due to the precipitation of cholesterol components dissolved in the lithotriptic, which is caused by cooling of the lithotriptic sucked from the organism passing through the tube during circulation of the lithotriptic. This means can also prevent the clogging of the suction duct or the like.

The function of this embodiment is described below.

The operator first makes a decision by using the input/control apparatus 428 as to whether or not bile discharge and saline washing are effected. If the bile discharge action is selected, the control unit 424 switches the electromagnetic change-over valve 425 in the direction shown by a dotted line arrow so that the valve 425 communicates with the exhaust bottle 419'. At the same time, the control unit 424 controls the irrigation pump 216 so that the rotor 216b is rotated in the discharge direction shown by a dotted line arrow, as well as rotating the suction pump 218 so as to suck the humor in the gallbladder. When the pressure in the gallbladder is zero, both pumps are stopped.

When the saline washing action is then selected, the electromagnetic change-over valve 425 is switched so that the irrigation tube 211 communicates with the liquid bottle 400 in which the saline is stored, and, at the same time, the start and end times of each of the pumps are calculated and set in the input/control apparatus 428, and the timer is then started. In the input/control apparatus 428, a decision is made as to whether or not the time read from the timer is the start of the irrigation pump 216 and the suction pump 218 so that the start and the stop of the rotation of each pump are controlled. The irrigation action and suction action are repeated predetermined times and then stopped. When the litholysis action is then selected, the electromagnetic change-over valve 425 is switched so as to communicate with the liquid bottle 417 containing the lithotriptic, and the irrigation and suction of the lithotriptic are controlled. During this operation, the liquid sucked is stored in the exhaust bottle 219.

When the lithotriptic in the human body 202 is completely discharged after the litholysis treatment, the valve 425 is switched so as to communicate with the exhaust bottle 419', and the irrigation pump 216 is rotated in the reverse direction so that the bile 419a' is returned to the gallbladder 204. In this case, since the bile is heated to the body temperature, there is an advantage in that the patient has no unpleasant feeling when the bile is returned to the human body.

Partial combination of the embodiments and the modification is also involved in the present invention.

What is claimed is:

1. A dissolution treatment apparatus comprising:
   irrigation means for irrigating the interior of a human body with a medical fluid which allow a coagulum produced to dissolve therein;
   discharge means for discharging said medical fluid containing said coagulum to the outside of said human body; and
   control means for controlling said irrigation means and said discharge means so as to adjust the quantity of said medical fluid introduced into said human body; and
   stop operation means for stopping dissolution treatment,
   wherein said control means controls said discharge means for discharging said medical fluid from said human body to the outside thereof before said treatment is stopped without immediately stopping said treatment in response to the operation of said stop operation means, said stop operation means immediately stopping said dissolution treatment after said medical fluid has been substantially discharged in response to said top operation means.

2. A dissolution treatment apparatus according to claim 1, further comprising second stop operation means for forcing, immediately after said medical fluid has been substantially discharged, said discharge means to stop during said discharge action in response to the operation of said stop operation means.

3. A litholysis treatment apparatus according to claim 1, wherein said control means controls the repetition of at least three steps including an irrigation step by said irrigation means, a rest step for allowing said medical fluid introduced to stand in said human body and a discharge step by said discharge means.

4. A dissolution treatment apparatus according to claim 3, wherein, when said control means performs said irrigation step, said control means controls said discharge means by stopping the action of said irrigation means and then operating said discharge means in response to the operation of said stop operation means.

5. A dissolution treatment apparatus according to claim 3, wherein, when said control means performs said rest step, said control means controls said discharge means by immediately operating said discharge means in response to the operation of said stop operation means.

6. A dissolution treatment apparatus according to claim 3, wherein, when said control means performs said discharge step, said control means controls said discharge means by continuing the operation of said discharge means in response to the operation of said stop operation means.

7. A dissolution treatment apparatus according to claim 1, wherein said control means continuously and alternatively drives said irrigation means and said discharge means.

8. A dissolution treatment apparatus according to claim 7, wherein said irrigation means and said discharge means comprise a single pump and a single tube which connects said pump and the interior of said human body so as to perform irrigation when said pump is rotated in one direction and suction when said pump is rotated in the other direction, said irrigation and said suction being repeated.

9. A dissolution treatment apparatus according to claim 8, wherein said control means controls said discharge means in response to the operation of said stop operation means by rotating said pump in said other direction.

10. A dissolution treatment apparatus according to claim 9, wherein said control means controls said discharge means by rotating pump in said other direction immediately in response to the operation of said stop operation means.

11. A dissolution treatment apparatus according to claim 8, wherein, when said stop operation means is operated, said control means causes said pump to be normally rotated until the movement in the other direction is completed in a reciprocating motion, wherein said control means controls said discharge means by the last movement of said pump in the other direction.

12. A dissolution treatment apparatus according to claim 1, wherein said control means simultaneously drives said irrigation means and said discharge means so as to constantly circulate an appropriate quantity of medical fluid in said organism.

13. A dissolution treatment apparatus according to claim 12, wherein said control means controls said discharge means, in response to the operation of said stop operation means, by stopping said irrigation means while operating said discharge means.

14. A dissolution treatment apparatus according to claim 13, further comprising pressure detecting means for detecting the pressure in a portion of said human body being treated and being irrigated with said medical fluid so that the discharge action taken in response to the operation of said stop operation means is completed in response to the detection of the substantially negative pressure by said detecting means.

15. A dissolution treatment apparatus according to claim 12, wherein said control means has arithmetic means for monitoring an irrigation quantity and a discharge quantity and calculating the quantity of the medical fluid presently remaining in said human body, and wherein said suction means discharges said calculated quantity of medical fluid from said human body.

16. A dissolution treatment apparatus according to claim 15, wherein said control means controls said discharge means by first stopping said irrigation means and said discharge means, starting said arithmetic means and then operating said discharge means in response to the operation of said stop operation means.

17. A litholysis apparatus comprising:
a control switch for controlling a litholysis control action of introducing a lithotriptic into the gallbladder and discharging from said gallbladder to the outside of a human body during an on-operation of the control switch and stopped with the off-operation of said control switch; and
a stop preparation means which is started with the off-operation of said control switch to discharge the lithotriptic in said gallbladder, said apparatus being stopped in response to an end of the discharge action.

18. A litholysis apparatus according to claim 17, wherein said stop preparation means has means for calculating a difference between the quantity of said lithotriptic introduced and the quantity of said lithotriptic discharged from the start of said litholysis control action to the off-operation of said control switch so as to determine the quantity of said lithotriptic discharged during the stop preparation action in response to the output from said calculating means.

19. A litholysis apparatus according to claim 17, wherein the discharge speed of said lithotriptic of said stop preparation means is higher than that in said litholysis control action.

20. A dissolution treatment apparatus comprising:
irrigation means for irrigating the interior of an organism with a medical fluid for dissolving a coagulum produced in said organism;
discharge means for discharging said medical fluid containing said coagulum dissolved therein to the outside of said organism; and
control means for alternately or simultaneously operating said irrigation mans and said discharge means so as to bring said medical fluid introduced into said organism into contact with said coagulum for dissolving it; and
start operation means for starting said dissolution treatment,
wherein said control means further performs pretreatment for discharging a humor in said organism and/or washing the interior of said organism before said dissolution treatment in response to the operation of said start operation means.

21. A dissolution treatment apparatus according to claim 20, wherein said control means performs said pretreatment so as to start said discharge means.

22. A litholysis apparatus for dissolving a calculus by circulating a lithotriptic in the gallbladder, said apparatus comprising:
a lithotriptic storing bottle for storing said lithotriptic;
a fluid path for connecting said storing bottle and an interior portion of said gallbladder;
pump means provided at an intermediate position of said fluid path for controlling the irrigation of said gallbladder with said fluid and the suction thereof;
control means for controlling said pump means; and
a means, connected to said control means, for starting and stopping said apparatus,
said control means performing a treatment mode for circulating said lithotriptic in said gallbladder by alternate or simultaneous irrigation and suction by using said pump means so as to perform a pretreatment mode before said treatment mode in response to a starting operation of said starting/stopping means and/or after treatment after said treatment mode in response to a stopping operation of said starting/stopping means.

23. A litholysis apparatus according to claim 22, wherein said control means performs said pretreatment mode for discharging under suction said bile in said gallbladder to the outside of an organism by operating said pump means.

24. A litholysis apparatus according to claim 22, further comprising a liquid bottle for storing a gallbladder washing fluid and selection means for selectively connecting said storing bottle and said liquid bottle to said pump means, said control means performs said pretreatment mode by causing said selection means to connect said pump means and said liquid bottle in place of said bottle for storing said lithotriptic so as to circulate said gallbladder washing fluid in said gallbladder.

25. A litholysis apparatus according to claim 22, wherein said control means performs said after treatment mode so as to operate said pump means and discharge under suction the medical fluid remaining in said gallbladder to the outside of said organism.

* * * * *